US008586600B2

(12) United States Patent
Singh et al.

(10) Patent No.: US 8,586,600 B2
(45) Date of Patent: Nov. 19, 2013

(54) HETEROCYCLIC COMPOUNDS AND USES THEREOF

(75) Inventors: Juswinder Singh, Ashland, MA (US); Shomir Ghosh, Brookline, MA (US); Arthur F. Kluge, Lincoln, MA (US); Russell C. Petter, Stow, MA (US)

(73) Assignee: Celgene Avilomics Research, Inc., Bedford, MA (US)

( * ) Notice: Subject to any disclaimer, the term of this patent is extended or adjusted under 35 U.S.C. 154(b) by 0 days.

(21) Appl. No.: 13/485,037

(22) Filed: May 31, 2012

(65) Prior Publication Data

US 2012/0238593 A1 Sep. 20, 2012

Related U.S. Application Data

(62) Division of application No. 12/132,537, filed on Jun. 3, 2008, now Pat. No. 8,242,271.

(60) Provisional application No. 60/941,873, filed on Jun. 4, 2007, provisional application No. 60/972,048, filed on Sep. 13, 2007.

(51) Int. Cl.
| | | |
|---|---|---|
| C07D 403/12 | (2006.01) | |
| C07D 403/14 | (2006.01) | |
| C07D 401/12 | (2006.01) | |
| C07D 401/14 | (2006.01) | |
| A61K 31/506 | (2006.01) | |
| A61P 35/00 | (2006.01) | |
| A61P 19/02 | (2006.01) | |

(52) U.S. Cl.
USPC .......................................... 514/275; 544/317

(58) Field of Classification Search
USPC .......................................... 544/317; 514/275
See application file for complete search history.

(56) References Cited

U.S. PATENT DOCUMENTS

| 5,521,184 | A | 5/1996 | Zimmermann |
|---|---|---|---|
| 6,878,697 | B2 | 4/2005 | Metcalf et al. |
| 7,081,532 | B2 | 7/2006 | Buerger et al. |
| 7,169,791 | B2 | 1/2007 | Breitenstein et al. |
| 8,242,271 | B2 * | 8/2012 | Singh et al. .................. 544/317 |
| 2004/0077661 | A1 | 4/2004 | Arbiser |
| 2004/0157855 | A1 | 8/2004 | Heinrich et al. |
| 2004/0180914 | A1 | 9/2004 | Batchelor et al. |
| 2005/0004125 | A1 | 1/2005 | Freyne et al. |
| 2005/0209452 | A1 | 9/2005 | Bornsen et al. |
| 2006/0009453 | A1 | 1/2006 | Geuns-Meyer et al. |
| 2006/0063789 | A1 | 3/2006 | Freyne et al. |
| 2006/0105445 | A1 | 5/2006 | Godl et al. |
| 2006/0142577 | A1 | 6/2006 | Manley et al. |
| 2006/0142580 | A1 | 6/2006 | Loiseleur et al. |
| 2006/0217404 | A1 | 9/2006 | Stein-Gerlach et al. |
| 2007/0129389 | A1 | 6/2007 | Bilbe |

FOREIGN PATENT DOCUMENTS

| EP | 1 702 917 A1 | 9/2006 |
|---|---|---|
| WO | WO 2004/029038 A1 | 4/2004 |
| WO | WO-2004/60305 | 7/2004 |
| WO | WO 2004/060305 A2 | 7/2004 |
| WO | WO-2005/049021 | 6/2005 |
| WO | WO-2005/63720 | 7/2005 |
| WO | WO-2005/065074 | 7/2005 |
| WO | WO-2005/072826 | 8/2005 |
| WO | WO-2005/115385 | 12/2005 |
| WO | WO-2006/017353 | 2/2006 |
| WO | WO-2006/21458 | 3/2006 |
| WO | WO-2006/79539 | 8/2006 |
| WO | WO-2006/89781 | 8/2006 |
| WO | WO-2006/119154 | 11/2006 |
| WO | WO-2006/135641 | 12/2006 |
| WO | WO-2007/10013 | 1/2007 |
| WO | WO-2007/18325 | 2/2007 |
| WO | WO-2007/65898 | 6/2007 |

OTHER PUBLICATIONS

Cecil Textbook of Medicine, edited by Bennet, J.C., and Plum F., 20th edition,vol. 1, 1004-1010, 1996.*
Freshney et al.,Culture of Animal Cells, A Manual of Basic Technique, Alan R. Liss, Inc., 1983, New York, p. 4.*
Dermer et al., Bio/Technology, 1994, 12:320.*
Cohen et al., Current Opinion in Chemical Biology, 3,459-465, 1999.*
Golub et al., Science, 286, 531-537, 1999.*
Mass, R. D., Int. J. Radiation Oncology Bio. Phys. vol. 58(3): 932-940, 2004.*
Fabbro et al. Pharmacology & therapeutics 93, 79-98, 2002.*
European Search Report, EP 08 77 0044, date of mailing Feb. 4, 2011.
International Search Report, PCT/US2008/65646, date of mailing Sep. 26, 2008.
Written Opinion, PCT/US2008/65646, date of mailing Sep. 26, 2008.
Kwak et al., "Irreversible inhibitors of the EGF receptor may circumvent acquired resistance to gefitinib," *Proc. Natl. Acad. Sci. USA* 102:7665-7670 (2005).
Zhang et al., "Targeting cancer with small molecule kinase inhibitors," *Nature Rev. Cancer* 9:28-39 (2009).
Akiyama et al., "Intraocular injection of an aptamer that binds PDGF-B: a potential treatment for proliferative retinopathies," J Cellular Physiology 2006, 207(2), 407-412.
Angelo et al., "Vascular Endothelial Growth Factor and its Relationship to Inflammatory Mediators," Clinical Cancer Research 2007, 13, 2825-2830.
Arceci et al., "Atypical Cellular Disorders" Hematology 2002, 1, 297-314.
Aubert et al., "Platelet-derived growth factor and its receptor in lungs from patients with asthma and chronic airflow obstruction," Am J Physiol Lung Cell Mol Physiol 1994, 266:L655-L663.
Baran et al., Am. J. Respir. Crit. Care Med. 2007, 176, 78-89.
Bilder et al., "Restenosis Following Angioplasty in the Swine Coronary Artery is Inhibited by an Orally Active PDGF-Receptor Tyrosine Kinase Inhibitor, RPR101511A," Circulation 1999, 99, 3292-3299.
Bonner, "Regulation of PDGF and its receptors in fibrotic diseases," Cytokine & Growth Factor Reviews 2004, 15, 255-273.
Carmeliet, "Angiogenesis in life, disease and medicine," Nature 2005, 438, 932-936.

(Continued)

*Primary Examiner* — Venkataraman Balasubramanian
(74) *Attorney, Agent, or Firm* — Choate Hall & Stewart LLP; Andrea L. C. Robidoux; Kristen C. Buteau

(57) ABSTRACT

The present invention provides compounds, pharmaceutically acceptable compositions thereof, and methods of using the same.

12 Claims, 3 Drawing Sheets

(56) References Cited

OTHER PUBLICATIONS

Chaudhary et al., "Inhibition of PDGF, VEGF and FGF signalling attenuates fibrosis," Eur Respir J 2007, 29, 976-985.
Choi et al., "Upregulation of Vascular Endothelial Growth Factor Receptors Flt-1 and Flk-1 Following Acute Spinal Cord Contusion in Rats," Journal of Histochemistry & Cytochemistry Mar. 2007, 55(8), 821-830.
Chu et al., "Growth inhibition of head and neck squamous cell carcinoma by imatinib mesylate (Gleevec)," Cancer Therapy 2005, 3, 515-524.
Conway et al., "Inhibition of colony-stimulating-factor-1 signaling in vivo with the orally bioavailable cFMS kinase inhibitor GW2580," PNAS 2005, 102(44), 16078-16083.
Ferguson et al., "Scar-free healing: from embryonic mechanisms to adult therapeutic intervention," Philosophical Transactions of the Royal Society of London, Series B: Biological Sciences 2004, 359(1445), 839-850.
Ferrante et al., "The Role of Vascular Endothelial Growth Factor (VEGF)in Inflammatory Bowel Disease," Inflamm Bowel Dis 2006,12(9),870-878.
Ferrara et al., "Angiogenesis as a therapeutic target," Nature 2005, 438, 967-974.
Giulian et al., "The Impact of Microglia-Derived Cytokines upon Gliosis in the CNS," Developmental Neuroscience 1994, 16, 128-136.
Guo et al., "Platelet-Derived Growth Factor-B Enhances Glioma Angiogenesis by Stimulating Vascular Endothelial Growth Factor Expression in Tumor Endothelia and by Promoting Pericyte Recruitment," Am. J. Pathology 2003, 162 (4), 1083-1093.
Heldin et al., "Mechanism of Action and In Vivo Role of Platelet-Derived Growth Factor," Physiological Reviews 1999, 79, 1283-1316.
Hoffman et al., "Molecular characterization of uterine fibroids and its implication for underlying mechanisms of pathogenesis," Fertility and Sterility 2004, 82(3), 639-649.
Holtkamp et al., "Mutation and expression of PDGFRA and KIT in malignant peripheral nerve sheath tumors, and its implications for imatinib sensitivity," Carcinogenesis 2006, 27(3), 664-671.
Jackson et al., "Vascular Endothelial Growth Factor (VEGF) Expression in Prostate Cancer and Benign Prostatic Hyperplasia," The Journal of Urology 1997, 157(6), 2323-2328.
Jain et al., "Targeting PDGF Signaling in Carcinoma-Associated Fibroblasts Controls Cervical Cancer in Mouse Model," PLoS Med. 2008, 5(1), e24.
Juurikivi et al., "Inhibition of c-kit tyrosine kinase by imatinib mesylate induces apoptosis in mast cells in rheumatoid synovia: a potential approach to the treatment of arthritis," Ann. Rheum. Dis. 2005;64:1126-1131.
Kalaria et al., "Vascular endothelial growth factor in Alzheimer's disease and experimental cerebral ischemia," Molecular Brain Research 1998, 62(1), 101-105.
Kang et al., "Post-cyclosporine-mediated hypertension and nephropathy: amelioration by vascular endothelial growth factor," Am J Physiol Renal Physiol 2001, 280, F727-F736.
Karayiannakis et al., "Circulating VEGF Levels in the Serum of Gastric Cancer Patients," Annals of Surgery 2002, 236(1), 37-24.
Kirk et al., "VEGF and vascular changes in chronic neuroinflammation," J Autoimmunity 2003, 21(4), 353-363.
Kunstfeld et al., Induction of cutaneous delayed-type hypersensitivity reactions in VEGF-A transgenic mice results in chronic skin inflammation associated with persistent lymphatic hyperplasia, Blood 2004, 104(4), 1048-1057.
Lee et al., "Vascular endothelial growth factor (VEGF) induces remodeling and enhances TH2-mediated sensitization and inflammation in the lung," Nat. Med. 2004, 10(10), 1095-1103.
Lefevre et al., "Role of Stem Cell Factor/c-Kit and Effects of Glivec®/STI571 in Human Uveal Melanoma Cell Tumorigenesis," J. Biol. Chem., 2004, 279(30), 31769-31779.
Liang et al., "Expression and Functional Analysis of Platelet-Derived Growth Factor in Uterine Leiomyomata," Cancer Biology & Therapy 5:1, Jan. 28-33, 2006.
Liekens et al., "Angiogenesis: regulators and clinical applications," Biochemical Pharmacology 2001, 61, 253-270.
Miettinen et al., "Kit Expression in Angiosarcomas and Fetal Endothelial Cells: Lack of Mutations of Exon 11 and Exon 17 of C-kit," Modern Pathology 2000, 13(5), 536-541.
Okazaki et al., International Immunology 2005, 18(1), 1-9.
Ongkeko et al., "Expression of Protein Tyrosine Kinases in Head and Neck Squamous Cell Carcinomas," Am. J. Clin. Pathol. 2005, 124, 71-76.
Pandiella et al., "Imatinib mesylate (STI571) inhibits multiple myeloma cell proliferation and potentiates the effect of common antimyeloma agents," British J Hematology 2003, 123, 858-868.
Penner et al., "C-kit Expression Distinguishes Salivary Gland Adenoid Cystic Carcinoma from Polymorphous Low-Grade Adenocarcinoma," Modern Pathology 2002, 15(7), 687-691.
Ponten et al., "Transgenic Overexpression of Platelet-Derived Growth Factor-C in the Mouse Heart Induces Cardiac Fibrosis, Hypertrophy, and Dilated Cardiomyopathy," Am. J. Pathology 2003, 163(2), 673-682.
Pufe et al., "The role of vascular endothelial growth factor in glucocorticoid-induced bone loss: evaluation in a minipig model," Bone, 33, 869-876, 2003.
Ravasco et al., "How Relevant are Cytokines in Colorectal Cancer Wasting?" Cancer Journal 2007, 13(6), 392-398.
Reber et al., Eur. J. Pharmacol. 2006, 533(1-3), 327-340.
Rice et al., "Specific Inhibitors of Platelet-Derived Growth Factor or Epidermal Growth Factor Receptor Tyrosine Kinase Reduce Pulmonary Fibrosis in Rats," Am. J. Pathol. 1999, 155(1), 213-221.
Roberts et al., "Antiangiogenic and Antitumor Activity of a Selective PDGFR Tyrosine Kinase Inhibitor, CP-673,451," Cancer Res. 2005;65:957-966.
Rönnstrand et al., Cell. Col. Life Sci. 2004, 61, 2535-2548.
Roskoski, "Sunitinib: A VEGF and PDGF receptor protein kinase and angiogenesis inhibitor," Biochemical and Biophysical Research Communications 2007, 356, 323-328.
Sadanaga et al., "Amelioration of Autoimmune Nephritis by Imatinib in MRL/lpr Mice," Arthritis & Rheumatism 2005, 52(12), 3987-3996.
Schermuly et al., "Reversal of experimental pulmonary hypertension by PDGF inhibition," J Clin Invest. 2005; 115(10):2811-2821.
Schneider et al., "Granulocyte-Macrophage Colony-Stimulating Factor-Induced Vessel Growth Restores Cerebral Blood Supply After Bilateral Carotid Artery Occlusion," Stroke 2007, 38, 1320-1328.
Seo et al., "Influence of VEGF gene polymorphisms on the severity of ankylosing spondylitis," Rheumatology 2005, 44, 1299-1303.
Shiojima et al., "The Role of Vascular Endothelial Growth Factor in Restenosis : The Controversy Continues," Circulation 2004, 110, 2289-2286.
Slomovitz et al., "Expression of imatinib mesylate-targeted kinases in endometrial carcinoma," Gynecologic Oncology 2004, 95, 32-36.
Sperling et al., "Expression of the Stem Cell Factor Receptor or c-KIT (CD117) in Acute Leukemias," Haematologica 1997, 82, 617-621.
Stadler et al., "Angiogenesis inhibitors in genitourinary cancers," Critical Reviews in Oncology/Hematology 2003, 46, S41-S47.
Stockhammer et al., "Vascular endothelial growth factor (VEGF) is elevated in brain tumor cysts and correlates with tumor progression," Acta Neuropathol 2000, 100(1), 101-105.
Thickett et al., "Vascular Endothelial Growth Factor May Contribute to Increased Vascular Permeability in Acute Respiratory Distress Syndrome," Am. J. Respir. Crit. Care Med. 2001, 164(9), 1601-1605.
Thomas, "Vascular Endothelial Growth Factor, a Potent and Selective Angiogenic Agent," The Journal of Biological Chemistry 1996, 271(2), 603-606.
Thornton et al., "Fibroblast growth factors in connective tissue disease associated interstitial lung disease," Clin. Exp. Immunol. 1992, 90, 447-452.
Tobler et al., "Tumor and lymph node lymphangiogenesis—impact on cancer metastasis," Journal of Leukocyte Biology 2006, 80(4), 691-696.

(56) References Cited

OTHER PUBLICATIONS

Tsuneyama et al., "Aberrant expression of stem cell factor on biliary epithelial cells and peribiliary infiltration of c-kit-expressing mast cells in hepatolithiasis and primary sclerosing cholangitis: a possible contribution to bile duct fibrosis," J Pathol. Dec. 1999; 189(4):609-614.

Uren et al., "Beta-platelet-derived growth factor receptor mediates motility and growth of Ewing's sarcoms cells," Oncogene 2003, 22, 2334-2342.

Viera et al., "Expression of vascular endothelial growth factor (VEGF) and its receptors in thyroid carcinomas of follicular origin: a potential autocrine loop," European Journal of Endocrinology (2005) 153 701-709.

Watanabe, "Erythropoietin as a Retinal Angiogenic Factor in Proliferative Diabetic Retinopathy," NEJM 2005, 353,782-792.

Werner et al., "Regulation of Wound Healing by Growth Factors and Cytokines," Physiol. Rev. 2002, 83, 835-870.

Wiedmann et al., "Imatinib mesylate (STI571; Glivec)—a new approach in the treatment of biliary tract cancer?," Anticancer Drugs 2003, 14(9), 751-760.

Yared et al., "Expression of c-kit Proto-Oncogene Product in Breast Tissue," The Breast Journal 2004, 10(4), 323-327.

Yu et al., "Platelet-derived Growth Factor Signaling and Human Cancer," J. Biochemistry and Molecular Biology 2003, 36(1), 49-59.

\* cited by examiner

HETEROCYCLIC COMPOUNDS AND USES THEREOF

CROSS-REFERENCE TO RELATED APPLICATIONS

The present application is a divisional application of U.S. patent application Ser. No. 12/132,537, filed Jun. 3, 2008 and issued as U.S. Pat. No. 8,242,271 on Aug. 14, 2012, which claims priority to U.S. provisional patent application Ser 60/941,873, filed Jun. 4, 2007, and U.S. provisional patent application Ser. No. 60/972,048, filed Sep. 13, 2007, the entirety of each of which is hereby incorporated herein by reference.

TECHNICAL FIELD OF THE INVENTION

The present invention relates to compounds useful as inhibitors of protein kinases. The invention also provides pharmaceutically acceptable compositions comprising compounds of the present invention and methods of using said compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

SUMMARY OF THE INVENTION

It has now been found that compounds of this invention, and pharmaceutically acceptable compositions thereof, are effective as inhibitors of one or more protein kinases. Such compounds have the general formula I:

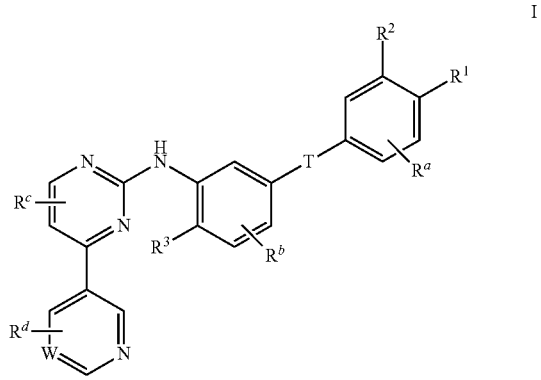

or a pharmaceutically acceptable salt thereof, wherein T, W, $R^a$, $R^b$, $R^c$, $R^d$, $R^1$, $R^2$, and $R^3$ are as defined herein.

Compounds of the present invention, and pharmaceutically acceptable compositions thereof, are useful for treating a variety of diseases, disorders or conditions, associated with abnormal cellular responses triggered by protein kinase-mediated events. Such diseases, disorders, or conditions include those described herein.

Compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF CERTAIN EMBODIMENTS

Figure 1:
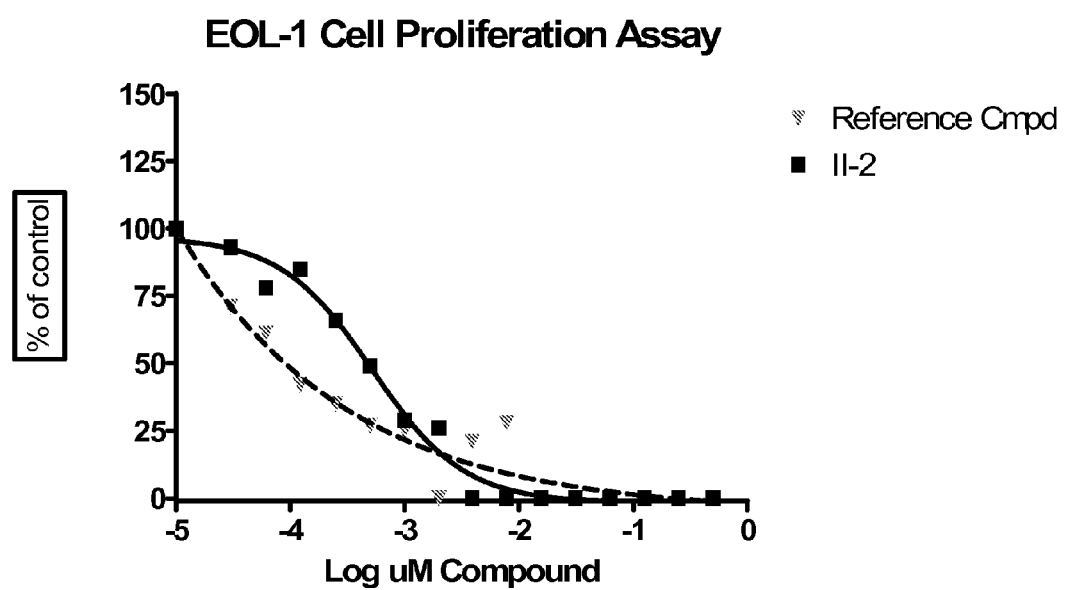
FIG. 1 depicts the dose response inhibition of cell proliferation of EOL-1 cells with reference compound and compound II-2.

1. General Description of Compounds of the Invention

In certain embodiments, the present invention provides a compound of formula I:

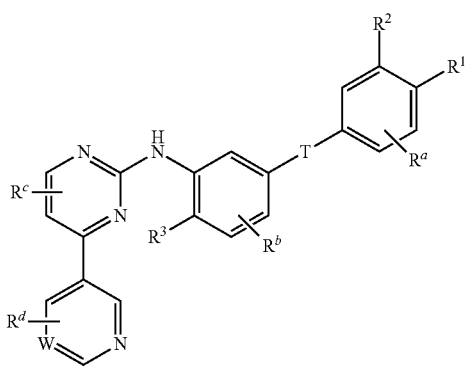

I or a pharmaceutically acceptable salt thereof, wherein:

T is —NHC(O)— or —C(O)NH—;

W is CH or N;

each of $R^a$, $R^b$, $R^c$, and $R^d$ is independently selected from R, OR, or halogen;

each R is independently hydrogen, lower alkyl, or lower haloalkyl;

$R^1$ is a warhead group;

$R^2$ is selected from R, halogen, —N(R)C(O)OR, or 1-imidazoyl substituted with R, or:

$R^1$ and $R^2$ are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group and 0-3 groups independently selected from oxo, halogen, CN, or $C_{1-6}$ aliphatic; and $R^3$ is selected from hydrogen, lower alkyl, or halogen.

In certain embodiments, the present invention provides a compound of formula II or III:

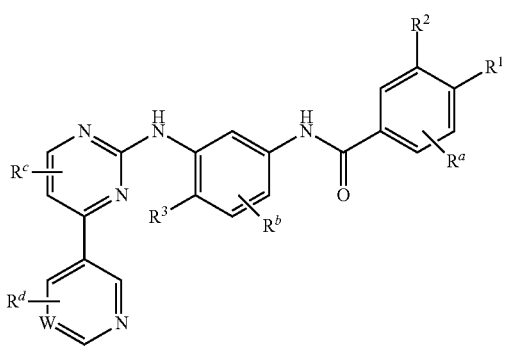

II

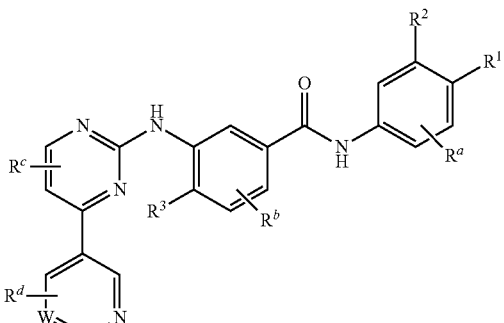

III or a pharmaceutically acceptable salt thereof, wherein:

each W is independently CH or N;

each of $R^a$, $R^b$, $R^c$, and $R^d$ is independently selected from R, OR, or halogen;

each R is independently hydrogen, lower alkyl, or lower haloalkyl;

each $R^1$ is independently a warhead group;

each $R^2$ is independently selected from R, halogen, —N(R)C(O)OR, or 1-imidazoyl substituted with R, or:

$R^1$ and $R^2$ are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group and 0-3 groups independently selected from oxo, halogen, CN, or $C_{1-6}$ aliphatic; and $R^3$ is selected from hydrogen, lower alkyl, or halogen.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments aliphatic groups contain 1-2 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{10}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

As used herein, the term "bivalent $C_{1-8}$ [or $C_{1-6}$] saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

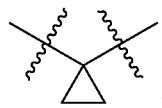

The term "halogen" means F, Cl, Br, or I.

The term "aryl" used alone or as part of a larger moiety as in "aralkyl", "aralkoxy", or "aryloxyalkyl", refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring".

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention. In some embodiments, the $R^1$ group of formula I comprises one or more deuterium atoms.

As used herein, the term "irreversible" or "irreversible inhibitor" refers to an inhibitor (i.e. a compound) that is able to be covalently bonded to a target protein kinase in a substantially non-reversible manner. That is, whereas a reversible inhibitor is able to bind to (but is generally unable to form a covalent bond) the target protein kinase, and therefore can become dissociated from the target protein kinase, an irreversible inhibitor will remain substantially bound to the target protein kinase once covalent bond formation has occurred. Irreversible inhibitors usually display time dependency, whereby the degree of inhibition increases with the time with which the inhibitor is in contact with the enzyme. Methods for identifying if a compound is acting as an irreversible inhibitor are known to one of ordinary skill in the art. Such methods include, but are not limited to, enzyme kinetic analysis of the inhibition profile of the compound with the protein kinase target, the use of mass spectrometry of the protein drug target modified in the presence of the inhibitor compound, discontinuous exposure, also known as "washout," experiments, and the use of labeling, such as radiolabelled inhibitor, to show covalent modification of the enzyme, as well as other methods known to one of skill in the art.

One of ordinary skill in the art will recognize that certain reactive functional groups can act as "warheads." As used herein, the term "warhead" or "warhead group" refers to a functional group present on a compound of the present invention wherein that functional group is capable of covalently binding to an amino acid residue (such as cysteine, lysine, histidine, or other residues capable of being covalently modified) present in the binding pocket of certain protein kinases, thereby irreversibly inhibiting the protein kinase. Exemplary reactive chemical functionalities useful as warheads include, but are not limited to, acrylamides, α-,β-, and N-substituted acrylamides, vinylsulfonamides, vinylsulfones, epoxysulphones, allyl sulphones, epoxides, aza peptide epoxides, α,β-unsaturated carbonyl derivatives, α,β unsaturated alcohols, Michael acceptors with acyl lactam, acyl oxazolidinone, and acyl urea functionalities, ester-derived Michael acceptors with substituted alcohol groups, cis-α,β-unsaturated esters or trans-α,β-unsaturated esters substituted at the α-position, amide-containing Michael acceptors, coumarins, cinnamates, and chalcones.

As used herein, the term "inhibitor" is defined as a compound that binds to and/or inhibits the target protein kinase with measurable affinity. In certain embodiments, an inhibitor has an $IC_{50}$ and/or binding constant of less about 50 μM, less than about 1 μM, less than about 500 nM, less than about 100 nM, or less than about 10 nM.

The terms "measurable affinity" and "measurably inhibit," as used herein, means a measurable change in PDGFR (alpha or beta), cKit, KDR, or cFMS, activity between a sample comprising a compound of the present invention, or composition thereof, and a PDGFR (alpha or beta), cKit, KDR, or cFMS, and an equivalent sample comprising PDGFR (alpha or beta), cKit, KDR, or cFMS, in the absence of said compound, or composition thereof.

3. Description of Exemplary Compounds

According to one aspect, the present invention provides a compound of formula II-a:

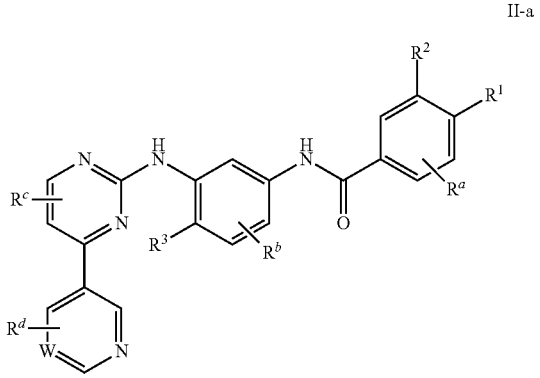

II-a or a pharmaceutically acceptable salt thereof, wherein:
W is CH or N;
each of $R^a$, $R^b$, $R^c$, and $R^d$ is independently selected from R, OR, or halogen;
each R is independently hydrogen, lower alkyl, or lower haloalkyl;
$R^1$ is -L-Y, wherein:
  L is a covalent bond or a bivalent $C_{1-8}$ saturated or unsaturated, straight or branched, hydrocarbon chain, wherein one, two, or three methylene units of L are optionally and independently replaced by —NR—, —N(R)C(O)—, —C(O)N(R)—, —O—, —C(O)—, —OC(O)—, —C(O)O—, —S—, —SO—, —SO$_2$—, —C(=S)—, —C(=NR)—, or —C(=N$_2$)—;
Y is hydrogen, $C_{1-6}$ aliphatic optionally substituted with oxo, halogen, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with at 1-4 groups independently selected from -Q-Z, oxo, halogen, CN, or $C_{1-6}$ aliphatic, wherein:
  Q is a covalent bond or a bivalent $C_{1-6}$ saturated or unsaturated, straight or branched, hydrocarbon chain, wherein one or two methylene units of Q are optionally and independently replaced by —NR—, —S—, —O—, —C(O)—, —SO—, or —SO$_2$—; and
  Z is hydrogen or $C_{1-6}$ aliphatic optionally substituted with oxo, halogen, or CN;
$R^2$ is selected from R, halogen, —N(R)C(O)OR, or 1-imidazoyl substituted with R, or:
  $R^1$ and $R^2$ are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group, wherein the warhead group is -Q-Z, and said ring is further substituted with 0-3 groups independently selected from oxo, halogen, CN, or $C_{1-6}$ aliphatic; and
$R^3$ is selected from hydrogen, lower alkyl, or halogen.

In certain embodiments, the W group is CH. In other embodiments, W is N. Thus, another embodiment of the present invention provides a compound of either of formulae II-b or II-c:

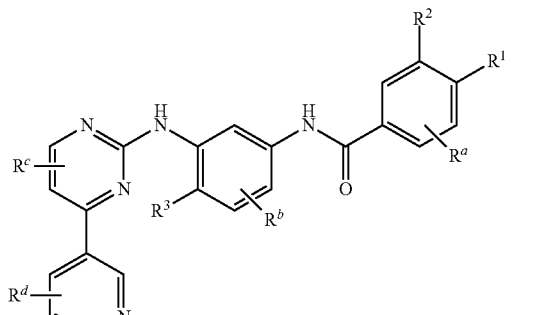

II-b

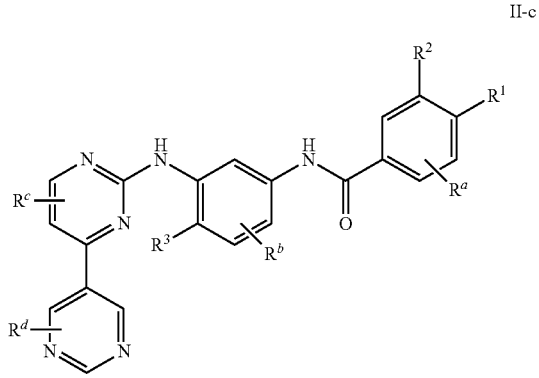

II-c or a pharmaceutically acceptable salt thereof, wherein each of $R^a$, $R^b$, $R^c$, $R^d$, $R^1$, $R^2$, and $R^3$ is as defined above and described in classes and subclasses herein.

In certain embodiments, each of the $R^a$, $R^b$, $R^c$, and $R^d$ groups is hydrogen.

As defined generally above, $R^1$ is -L-Y, wherein L is a covalent bond or a bivalent $C_{1-8}$ saturated or unsaturated, straight or branched, hydrocarbon chain, wherein one, two, or three methylene units of L are optionally and independently replaced by —NR—, —N(R)C(O)—, —C(O)N(R)—, —O—, —C(O)—, —OC(O)—, —C(O)O—, —S—, —SO—, —SO$_2$—, —C(=S)—, —C(=NR)—, —N=N—, or —C(=N$_2$)—, and Y is hydrogen, $C_{1-6}$ aliphatic, or a 3-7 membered saturated, partially unsaturated, or aryl ring having 0-3 heteroatoms independently selected from nitrogen, oxygen, or sulfur, and wherein said ring is substituted with 1-4 groups independently selected from oxo, halogen, CN, $C_{1-6}$ aliphatic, or -Q-Z.

In certain embodiments, L is a covalent bond.

In other embodiments, L is a bivalent $C_{1-8}$ saturated or unsaturated, straight or branched, hydrocarbon chain wherein at least one methylene unit of L is replaced by —S—, —S(O)—, —SO$_2$—, —C(=S)—, —C(=NR)—, or —C(=N$_2$)—, and one or two additional methylene units of L are optionally and independently replaced by —O—, —N(R)—, or —C(O)—. In some embodiments, L is a bivalent $C_{2-8}$ straight or branched, hydrocarbon chain wherein L has at least one double bond and at least one methylene unit of L is replaced by —NRC(O)—, —C(O)NR—, —N(R)SO$_2$—, —SO$_2$N(R)—, —S—, —S(O)—, —SO$_2$—, —C(=S)—, —C(=NR)—, or —C(=N$_2$)—, and one or two additional methylene units of L are optionally and independently replaced by cyclopropylene, —O—, —N(R)—, or —C(O)—. In still other embodiments, L is a bivalent $C_{1-8}$ straight or branched, alkylene chain, wherein at least one methylene unit of L is replaced by —S—, —S(O)—, —SO$_2$—, —C(=S)—, —C(=NR)—, or —C(=N$_2$)—, and one or two additional methylene units of L are optionally and independently replaced by —O—, —N(R)—, or —C(O)—. In some embodiments, L is a bivalent $C_{1-8}$, straight or branched, alkylene chain, wherein at least one methylene unit of L is replaced by —C(=N$_2$)—, and one or two additional methylene units of L are optionally and independently replaced by —NRC(O)—, —C(O)NR—, —S—, —S(O)—, —SO$_2$—, —C(=S)—, —C(=NR)—, —O—, —N(R)—, or —C(O)—.

In certain embodiments, L is a bivalent $C_{1-8}$ saturated or unsaturated, straight or branched, hydrocarbon chain. In certain embodiments, L is —CH$_2$—.

In some embodiments, L is a bivalent $C_{2-8}$ straight or branched, hydrocarbon chain wherein L has at least one triple bond. In certain embodiments, L is a bivalent $C_{2-8}$ straight or branched, hydrocarbon chain wherein L has at least one triple bond and one or two additional methylene units of L are optionally and independently replaced by —NRC(O)—, —C(O)NR—, —S—, —S(O)—, —SO$_2$—, —C(=S)—, —C(=NR)—, —O—, —N(R)—, or —C(O)—. In some embodiments, L has at least one triple bond and at least one methylene unit of L is replaced by —N(R)—, —N(R)C(O)—, or —O—.

Exemplary L groups include —C≡C—, —C≡CCH$_2$N (isopropyl)-, —NHC(O)C≡CCH$_2$CH$_2$—, —CH$_2$—C≡C—CH$_2$—, and —C≡CCH$_2$O—.

In certain embodiments, L is a bivalent $C_{2-8}$ straight or branched, hydrocarbon chain wherein L has at least one double bond and at least one methylene unit of L is replaced by cyclopropylene, —NRC(O)—, —C(O)NR—, —N(R)SO$_2$—, —SO$_2$N(R)—, —S—, —S(O)—, —SO$_2$—, —C(=S)—, —C(=NR)—, or —C(=N$_2$)—, and one or two additional methylene units of L are optionally and independently replaced by —O—, —N(R)—, or —C(O)—.

Exemplary L groups include —CH$_2$—, —NH—, —CH$_2$NH—, —NHCH$_2$—, —NHC(O)—, —NHC(O)CH$_2$OC(O)—, —NHC(O)CH=CH—, —CH$_2$NHC(O)—, —NHC(O)CH=CHCH$_2$N(CH$_3$)—, —NHC(O)CH=CHCH$_2$O—, —CH$_2$NHC(O)CH=CH—, —NHSO$_2$—, —NHSO$_2$CH$_2$—, —NHSO$_2$CH=CH—, —NHSO$_2$CH=CHCH$_2$—, —NHC(O)(C=N$_2$)—, —NHC(O)(C=N$_2$)C(O)—, —NHC(O)CH$_2$OC(O)—, —SO$_2$NH—, —NHC(O)CH=CHCH$_2$N(CH$_3$)—, and —NHC(O)CH=CHCH$_2$O—.

As described above, in certain embodiments, L is a bivalent $C_{2-8}$ straight or branched, hydrocarbon chain wherein L has at least one double bond. One of ordinary skill in the art will recognize that such a double bond may exist within the hydrocarbon chain backbone or may be "exo" to the backbone chain and thus forming an alkylidene group. By way of example, such an L group having an alkylidene branched chain includes —CH$_2$C(=CH$_2$)CH$_2$—. Thus, in some embodiments, L is a bivalent $C_{2-8}$ straight or branched, hydrocarbon chain wherein L has at least one alkylidenyl double bond. Exemplary L groups include —NHC(O)C(=CH$_2$)CH$_2$—.

In certain embodiments, L is a bivalent $C_{2-8}$ straight or branched, hydrocarbon chain wherein one methylene unit of L is replaced by cyclopropylene and one or two additional methylene units of L are independently replaced by —C(O)—, —NRC(O)—, —C(O)NR—, —N(R)SO$_2$—, or —SO$_2$N(R)—. Exemplary L groups include —NHC(O)-cyclopropylene-SO$_2$— and —NHC(O)-cyclopropylene-.

In certain embodiments, Y is hydrogen.

In certain embodiments, Y is $C_{1-6}$ aliphatic optionally substituted with oxo, halogen, or CN. In other embodiments, Y is $C_{1-6}$ alkyl. In some embodiments, Y is $C_{2-6}$ alkenyl. In other embodiments, Y is $C_{2-4}$ alkynyl. In certain embodiments, Y is cyclopropyl optionally substituted with —CN or —NO$_2$. In some embodiments, Y is cyclopropenyl or cyclobutenyl.

In certain embodiments, Y is a 3-10 membered monocyclic or bicyclic, saturated, partially unsaturated, or aryl ring having 0-3 heteroatoms independently selected from nitrogen, oxygen, or sulfur, and wherein said ring is substituted with 1-4 groups independently selected from -Q-Z, oxo, halogen, CN, or $C_{1-6}$ aliphatic.

In some embodiments, Y is phenyl or pyridyl.

In certain embodiments, Y is a saturated 3-6 membered monocyclic ring having 1-3 heteroatoms independently selected from nitrogen, oxygen, or sulfur, wherein Y is substituted as defined above. In some embodiments, Y is a saturated 3-4 membered monocyclic ring having 1 heteroatom selected from oxygen or nitrogen. Exemplary rings are epoxide and oxetane rings. In other embodiments, Y is a saturated 5-6 membered monocyclic ring having 1-2 heteroatom selected from oxygen or nitrogen. Such rings include piperidine and pyrrolidine.

In other embodiments, Y is a 5 membered partially unsaturated or aryl ring having 1-3 heteroatoms independently selected from nitrogen, oxygen, or sulfur, wherein Y is substituted as defined above. In some embodiments, Y is a 5 membered partially unsaturated or aryl ring having 1-3 heteroatoms independently selected from nitrogen, oxygen, and sulfur. Exemplary rings are thiadiazole, oxazole, oxadiazole, and 2,5-dihydro-1H-pyrrole.

In certain embodiments, Y is an 8-10 membered bicyclic, saturated, partially unsaturated, or aryl ring having 0-3 heteroatoms independently selected from nitrogen, oxygen, or sulfur, wherein Y is substituted as defined above. According to another aspect, Y is a 9-10 membered bicyclic, partially unsaturated, or aryl ring having 1-3 heteroatoms independently selected from nitrogen, oxygen, or sulfur. Exemplary bicyclic rings include 2,3-dihydrobenzo[d]isothiazole.

As defined generally above, when Y is a ring, said ring is substituted with 1-4 groups independently selected from -Q-Z, oxo, $NO_2$, halogen, CN, or $C_{1-6}$ aliphatic. In certain embodiments, Q is a bivalent $C_{1-6}$ saturated or unsaturated, straight or branched, hydrocarbon chain, wherein one or two methylene units of Q are optionally and independently replaced by —NR—, —NRC(O)—, —C(O)NR—, —S—, —O—, —C(O)—, —SO—, or —$SO_2$—. In other embodiments, Q is a bivalent $C_{2-6}$ straight or branched, hydrocarbon chain having at least one double bond, wherein one or two methylene units of Q are optionally and independently replaced by —NR—, —NRC(O)—, —C(O)NR—, —S—, —O—, —C(O)—, —SO—, or —$SO_2$—. In some embodiments, -Q-Z is —NHC(O)CH=$CH_2$ or —C(O)CH=$CH_2$. In certain embodiments, the Y ring is substituted with at least one group selected from oxo, fluoro, chloro, —NHC(O)CH=$CH_2$, —C(O)CH=$CH_2$, $NO_2$, —C(O)OEt, or CN.

In certain embodiments, Y is selected from those set forth in Table 1, below, wherein each wavy line indicates the point of attachment to the rest of the molecule.

TABLE 1

Exemplary Y groups:

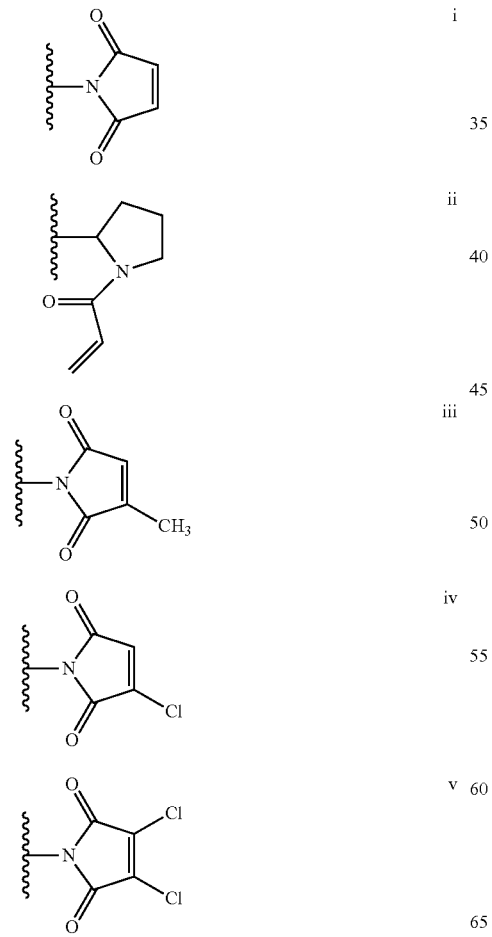

TABLE 1-continued

Exemplary Y groups:

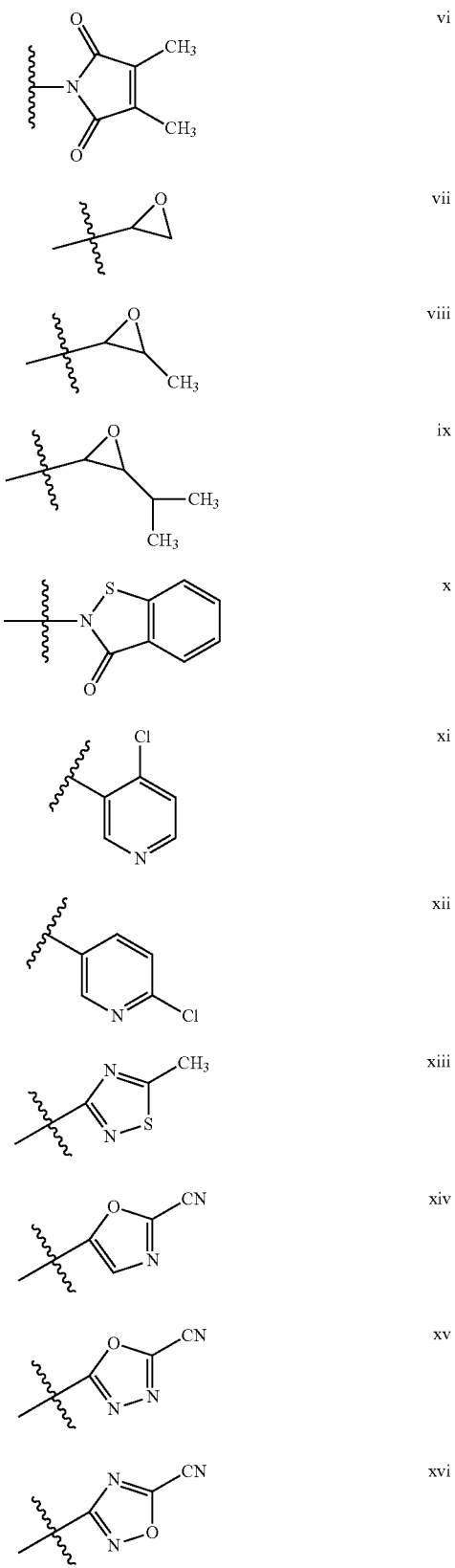

TABLE 1-continued
Exemplary Y groups:
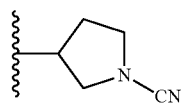 xvii
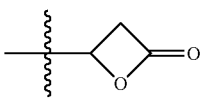 [SMILES: *C1CC(=O)O1] xviii
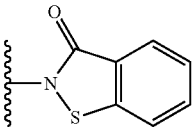 [SMILES: *n1sc2ccccc2c1=O] xix
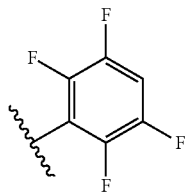 [SMILES: *c1c(F)c(F)cc(F)c1F] xx
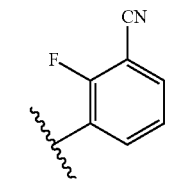 [SMILES: *c1cccc(C#N)c1F] xxi
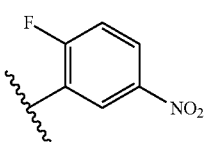 [SMILES: *c1cc([N+](=O)[O-])ccc1F] xxii
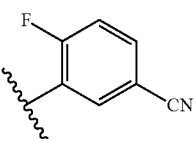 [SMILES: *c1cc(C#N)ccc1F] xxiii
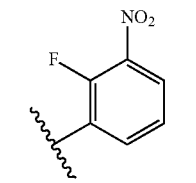 [SMILES: *c1cccc([N+](=O)[O-])c1F] xxiv
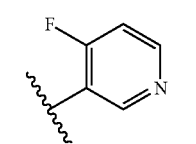 [SMILES: *c1cnccc1F] xxv
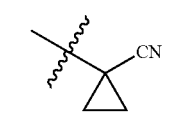 [SMILES: *C1(C#N)CC1] xxvi
TABLE 1-continued
Exemplary Y groups:
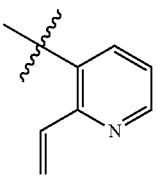 xxvii
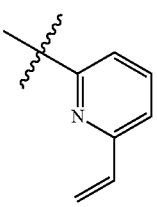 [SMILES: *c1cccc(C=C)n1] xxviii
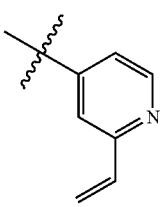 [SMILES: *c1ccnc(C=C)c1] xxix
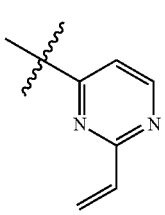 [SMILES: *c1ccnc(C=C)n1] xxx
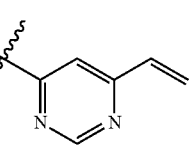 xxxi
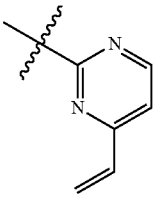 xxxii
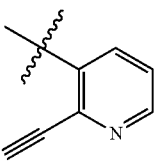 [SMILES: *c1cccnc1C#C] xxxiii
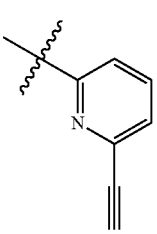 [SMILES: *c1cccc(C#C)n1] xxxiv TABLE 1-continued
Exemplary Y groups:
 xxxv
 xxxvi
 xxxvii
 xxxviii
 xxxix
 xl
 xli
 xlii
TABLE 1-continued
Exemplary Y groups:
 xliii
 xliv
 xlv
xlvi
xlvii
xlviii
xlix
l
li
lii TABLE 1-continued
Exemplary Y groups:
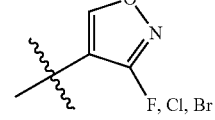 liii
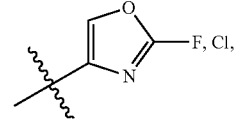 liv
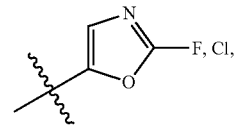 lv
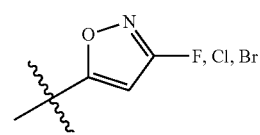 lvi
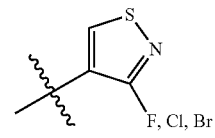 lvii
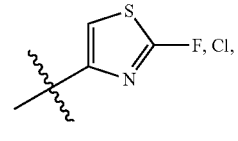 lviii
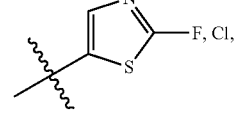 lix
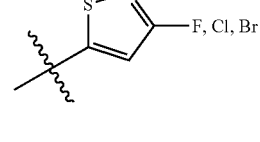 lx
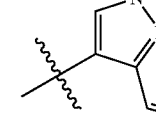 lxi
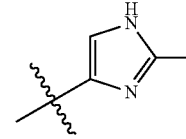 lxii
TABLE 1-continued
Exemplary Y groups:
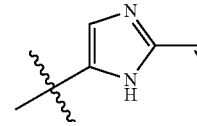 lxiii
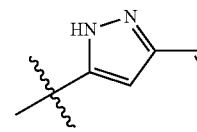 lxiv
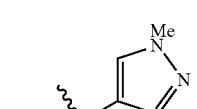 lxv
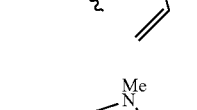 lxvi
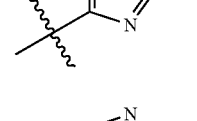 lxvii
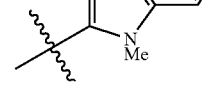 lxviii
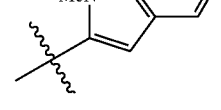 lxix
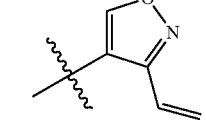 lxx
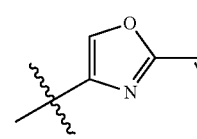 lxxi
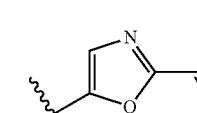 lxxii TABLE 1-continued
Exemplary Y groups:
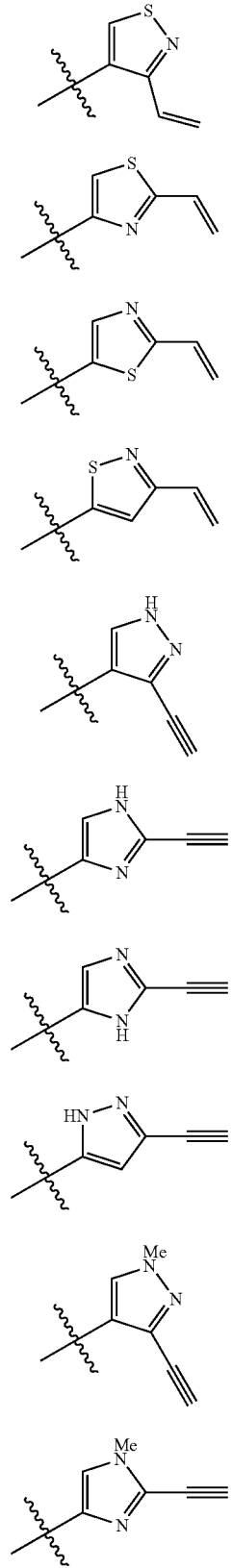
lxxiii
lxxiv
lxxv
lxxvi
lxxvii
lxxviii
lxxix
lxxx
lxxxi
lxxxii
TABLE 1-continued
Exemplary Y groups:
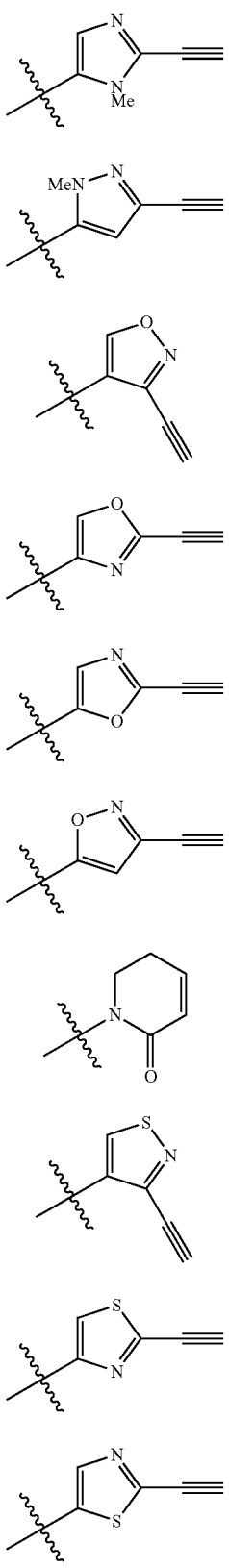
lxxxiii
lxxxiv
lxxxv
lxxxvi
lxxxvii
lxxxviii
lxxxix
xc
xci
xcii TABLE 1-continued Exemplary Y groups:

[Structures xciii through cii shown, including isothiazole with ethynyl, pyrrolinone, pyrrolidine acrylamide, pyrazole ethynyl, imidazole ethynyl, and halogenated pyrazole/imidazole variants]

TABLE 1-continued

Exemplary Y groups:

[Structures ciii through cix shown, including halogenated pyrazoles, vinyl pyrazoles and vinyl imidazoles]

In certain embodiments, Y is other than maleimide when L is —CH$_2$—. In other embodiments, Y is other then epoxide when L is —CH$_2$—.

In certain embodiments, $R^1$ is selected from those set forth in Table 2, below, wherein each wavy line indicates the point of attachment to the rest of the molecule.

TABLE 2

Exemplary $R^1$ Groups

[Structure i: cyanocyclopropyl amide]

[Structure ii: acrylamide ethyl]

TABLE 2-continued
Exemplary R¹ Groups
| | |
|---|---|
| 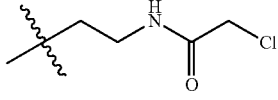 [SMILES: *CCNC(=O)CCl] | iii |
| 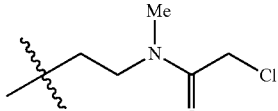 | iv |
| 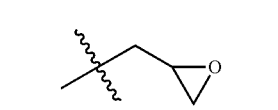 | v |
| 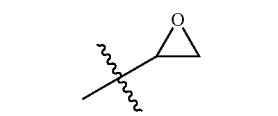 [SMILES: *C1CO1] | vi |
| 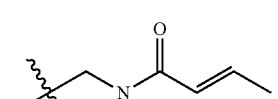 | vii |
| 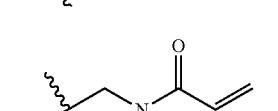 | viii |
| 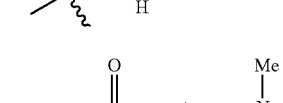 | ix |
| 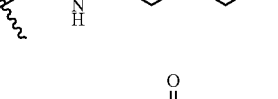 | x |
| 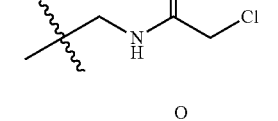 | xi |
| 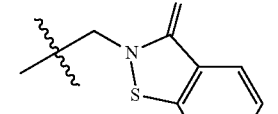 | xii |
| 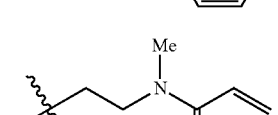 | xiii |
| 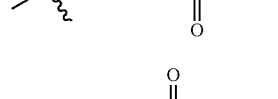 | xiv |
TABLE 2-continued
Exemplary R¹ Groups
| | |
|---|---|
| 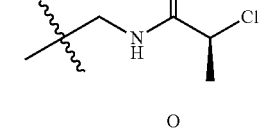 | xv |
| 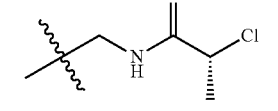 | xvi |
|  | xvii |
| 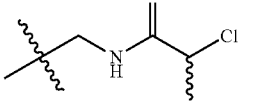 | xviii |
| 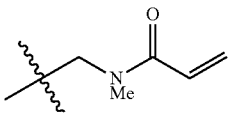 | xix |
| 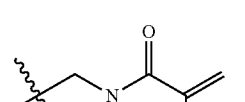 | xx |
| 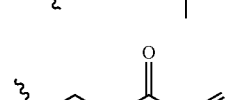 | xxi |
| 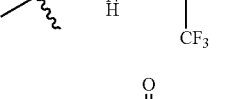 | xxii |
| 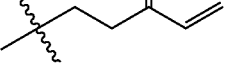 | xxiii |
| 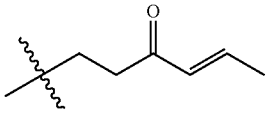 [SMILES: *CCC(=O)/C=C/C] | xiv |
| 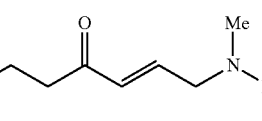 | xv |
| 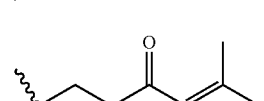 | xxvi |

TABLE 2-continued
Exemplary R¹ Groups
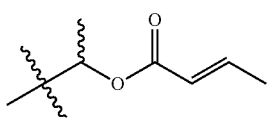 [SMILES: *C(C)OC(=O)/C=C/C] xxvii
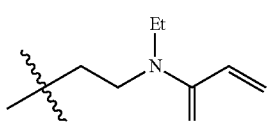 xxviii
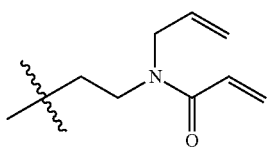 [SMILES: *CCN(CC=C)C(=O)C=C] xxix
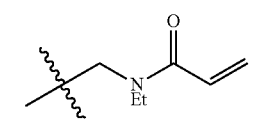 xxx
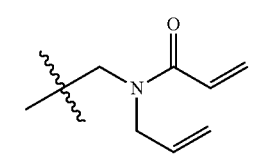 [SMILES: *CN(CC=C)C(=O)C=C] xxxi
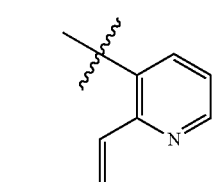 [SMILES: *c1cccnc1C=C] xxxii
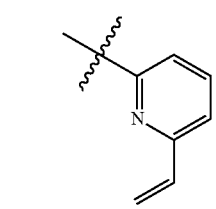 [SMILES: *c1cccc(C=C)n1] xxxiii
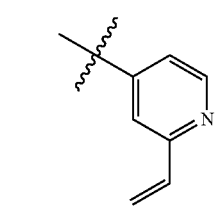 [SMILES: *c1ccnc(C=C)c1] xxxiv
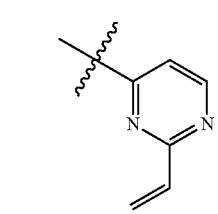 xxxv
TABLE 2-continued
Exemplary R¹ Groups
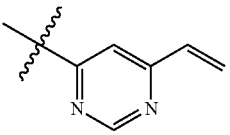 [SMILES: *c1cc(C=C)ncn1] xxxvi
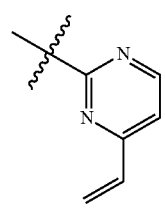 [SMILES: *c1nccc(C=C)n1] xxxvii
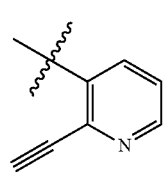 [SMILES: *c1cccnc1C#C] xxxviii
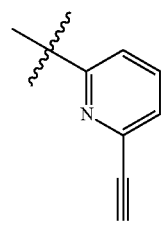 [SMILES: *c1cccc(C#C)n1] xxxix
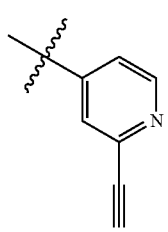 [SMILES: *c1ccnc(C#C)c1] xl
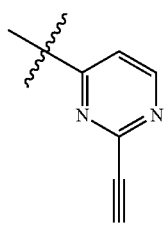 [SMILES: *c1ccnc(C#C)n1] xli
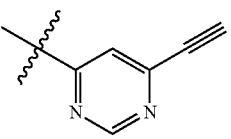 [SMILES: *c1cc(C#C)ncn1] xlii
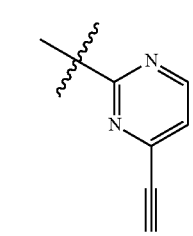 [SMILES: *c1nccc(C#C)n1] xliii TABLE 2-continued Exemplary R¹ Groups (Structures showing heteroaryl R¹ groups xliv through lxiii, each substituted with F, Cl, or Br)

xliv, xlv, xlvi, xlvii, xlviii, xlix, l, li, lii, liii, liv, lv, lvi, lvii, lviii, lix, lx, lxi, lxii, lxiii TABLE 2-continued
Exemplary R¹ Groups
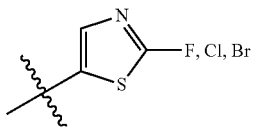 lxiv
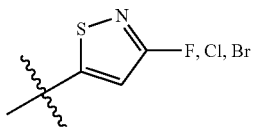 lxv
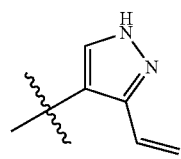 [SMILES: *c1c[nH]nc1C=C] lxvi
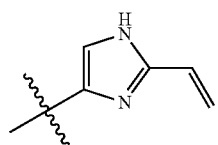 [SMILES: *c1c[nH]c(C=C)n1] lxvii
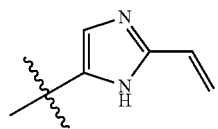 [SMILES: *c1cnc(C=C)[nH]1] lxviii
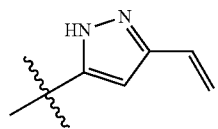 [SMILES: *c1cc(C=C)n[nH]1] lxix
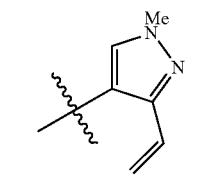 lxx
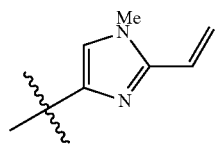 [SMILES: *c1cn(C)c(C=C)n1] lxxi
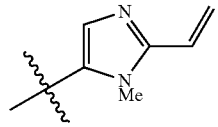 lxxii
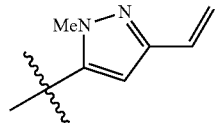 [SMILES: *c1cc(C=C)nn1C] lxxiii
TABLE 2-continued
Exemplary R¹ Groups
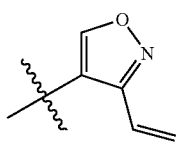 [SMILES: *c1conc1C=C] lxxiv
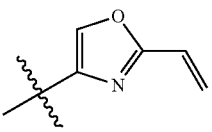 [SMILES: *c1coc(C=C)n1] lxxv
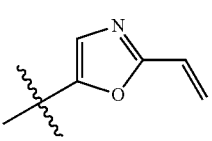 [SMILES: *c1cnc(C=C)o1] lxxvi
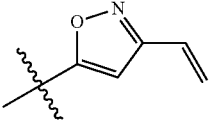 [SMILES: *c1cc(C=C)no1] lxxvii
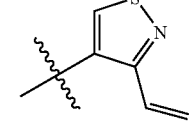 lxxviii
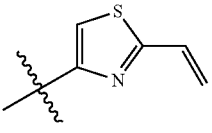 [SMILES: *c1csc(C=C)n1] lxxix
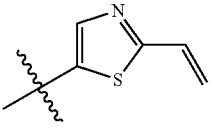 lxxx
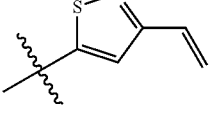 lxxxi
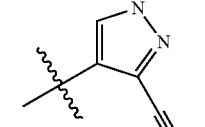 lxxxii
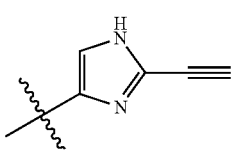 [SMILES: *c1c[nH]c(C#C)n1] lxxxiii TABLE 2-continued Exemplary R¹ Groups

| | |
|---|---|
| (structure) | lxxxiv |
| (structure) | lxxxv |
| (structure) | lxxxvi |
| (structure) | lxxxvii |
| (structure) | lxxxviii |
| (structure) | lxxxix |
| (structure) | xc |
| (structure) | xci |
| (structure) | xcii |
| (structure) | xciii |
| (structure) | xciv |
| (structure) | xcv |
| (structure) | xcvi |
| (structure) | xcvii |
| (structure) | xcviii |
| (structure) | xcix |
| (structure) | c |
| (structure) | ci |
| (structure) | cii |
| (structure) | ciii |

TABLE 2-continued

Exemplary R¹ Groups

| Structure | Label |
|---|---|
| cyclohexenyl-C(O)NH– with 2-F | civ |
| –CH₂-O-C(O)-cyclopropyl-C(O)CH₃ | cv |
| –C(O)-C≡CH | cvi |
| –NH-C(O)-C≡CH | cvii |
| –CH₂-O-C(O)-C≡CH | cviii |
| –C(O)-cyclopropyl-CN | cix |
| –CH₂-O-C(O)-CH=CH₂ | cx |
| pyrrolidinyl-N-C(O)-CH=CH₂ | cxi |
| –CH₂-N(CH₃)-C(O)-CH=CH-CH₂-N(CH₃)₂ | cxii |
| –CH₂-N(CH₂CH₃)-C(O)-CH=CH-CH₂-N(CH₃)₂ | cxiii |
| –CH₂-N(CH₂CH=CH₂)-C(O)-CH=CH-CH₂-N(CH₃)₂ | cxiv |
| 1H-pyrazol-3-yl with C≡CH | cxv |
| imidazol-4-yl with 2-C≡CH | cxvi |
| 1H-pyrazol-5-yl with 3-C≡CH | cxvii |
| pyrazol-1-yl with 3-C≡CH | cxviii |
| imidazol-1-yl with 2-C≡CH | cxix |
| 1H-pyrazol-5-yl with F, Cl, Br | cxx |
| imidazol-4-yl with F, Cl, Br | cxxi |
| 1H-pyrazol-5-yl with F, Cl, Br | cxxii |
| pyrazol-1-yl with F, Cl, Br | cxxiii |

TABLE 2-continued

Exemplary R¹ Groups

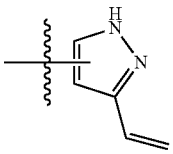
cxxiv

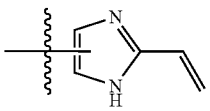
cxxv

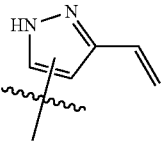
cxxvi

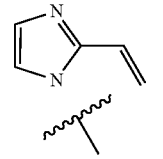
cxxvii

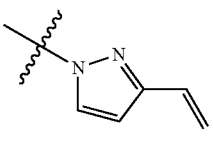 [SMILES: *n1ccc(C=C)n1]
cxxviii

In certain embodiments, R¹ is selected from —NHC(O)CH=CH₂ or —CH₂NHC(O)CH=CH₂.

As defined generally above, R¹ is a warhead group, or, when R¹ and R² form a ring, then -Q-Z is a warhead group. Without wishing to be bound by any particular theory, it is believed that such R¹ groups, i.e. warhead groups, are particularly suitable for covalently binding to a key cysteine residue in the binding domain of certain protein kinases. Protein kinases having a cysteine residue in the binding domain are known to one of ordinary skill in the art and include PDGFR (alpha and beta), cKit, KDR, and cFMS. In certain embodiments, compounds of the present invention have a warhead group characterized in that inventive compounds target one or more of the following cysteine residues:

| KDR | SRKCIHRDLA | (C1024; http://www.ebi.uniprot.org/entry/P35968) |
| --- | --- | --- |
| cKIT | AFLASKNCIH | (C788; http://www.ebi.uniprot.org/entry/P10721) |
| PDGFR-α | SKNCVHRDLA | (C814; http://www.ebi.uniprot.org/entry/P16234) |
| PDGFR-β | NCVHRDLAAR | (C822; http://www.ebi.uniprot.org/entry/P09619) |
| cFMS | SKNCIHRDVA | (C774; http://www.ebi.uniprot.org/entry/P07333) |

Thus, in some embodiments, R¹ is characterized in that the -L-Y moiety is capable of covalently binding to a cysteine residue thereby irreversibly inhibiting the enzyme. One of ordinary skill in the art will recognize that a variety of warhead groups, as defined herein, are suitable for such covalent bonding. Such R¹ groups include, but are not limited to, those described herein and depicted in Table 2, infra.

According to another aspect, the present invention provides a conjugate comprising any of PDGFR-α, PDGFR-β, c-KIT, cFMS, or KDR, or a mutant thereof, covalently bonded to an inhibitor at Cys814, Cys822, Cys788, Cys774, or Cys 1024, respectively. In some embodiments, the inhibitor is covalently bonded via a linker moiety.

In certain embodiments, the present invention provides a conjugate of the formula Cys814-linker-inhibitor moiety, Cys822-linker-inhibitor moiety, Cys788-linker-inhibitor moiety, Cys774-linker-inhibitor moiety, or Cys1024-linker-inhibitor moiety, wherein the Cys814 is of PDGFR-α; the Cys822 is of PDGFR-β; the Cys788 is of c-KIT; the Cys774 is of cFMS and the Cys1024 is of KDR. One of ordinary skill in the art will recognize that the "linker" group corresponds to an -L-Y warhead group as described herein. Accordingly, in certain embodiments, the linker group is as defined for -L-Y was defined above and described in classes and subclasses herein. It will be appreciated, however, that the linker group is bivalent and, therefore, the corresponding -L-Y group is also intended to be bivalent resulting from the reaction of the warhead with the targeted cysteine.

In certain embodiments, the inhibitor moiety is a compound of formula A:

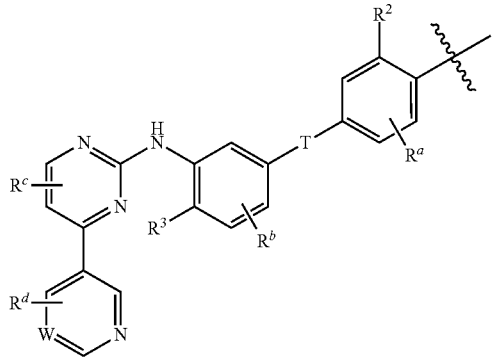

wherein each of the R², R³, Rᵃ, Rᵇ, Rᶜ, Rᵈ, and W groups of formula A is as defined for formula I above and described in classes and subclasses herein. Thus, in certain embodiments, the present invention provides a conjugate of any of formulae:

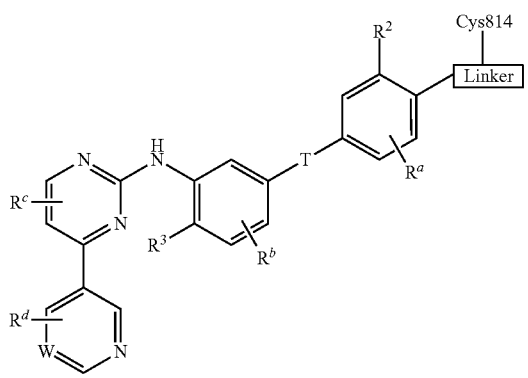

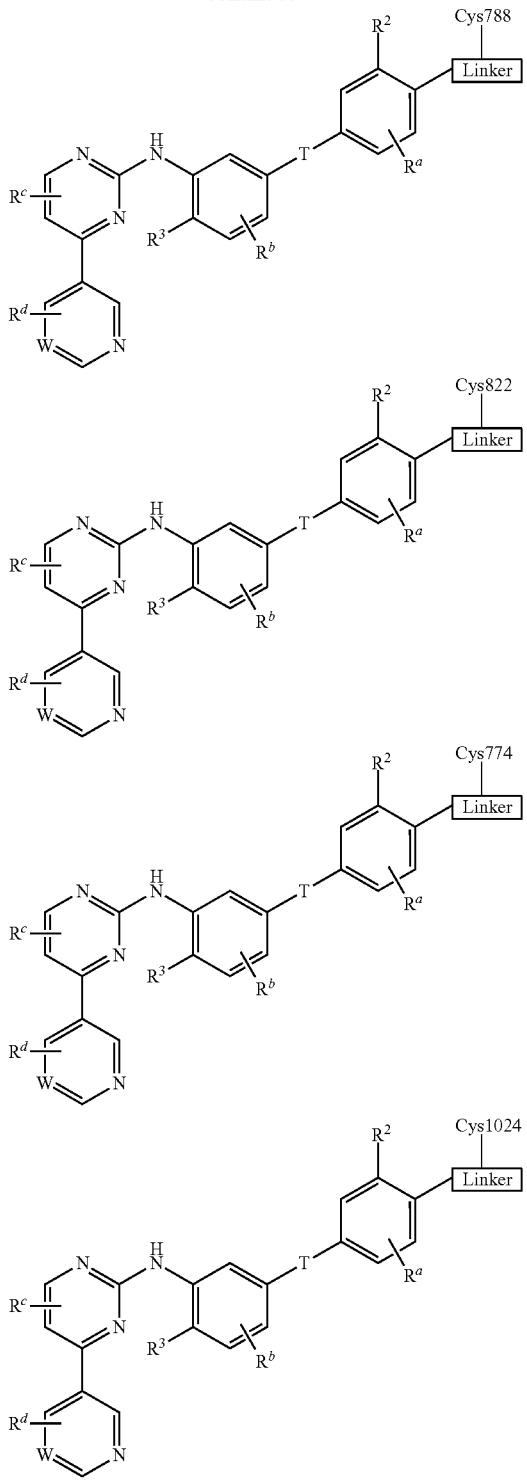

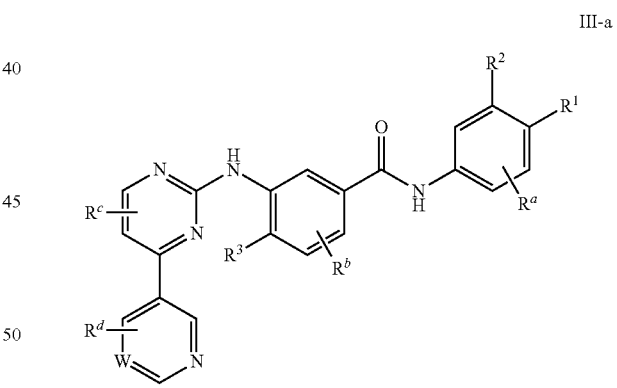

wherein each of the R², R³, R^a, R^b, R^c, R^d, and W groups of formula A is as defined for formula I above and described in classes and subclasses herein and wherein the Cys814 is of PDGFR-α; the Cys822 is of PDGFR-β; the Cys788 is of c-KIT; the Cys774 is of cFMS1 and the Cys1024 is of KDR.

As defined generally above, R² is selected from R, halogen, —N(R)C(O)OR, or 1-imidazoyl substituted with R, or R¹ and R² are taken together with their intervening atoms to form a 5-7 membered saturated, partially unsaturated, or aryl ring having 0-3 heteroatoms independently selected from nitrogen, oxygen, or sulfur, wherein said ring is substituted with 1-3 groups independently selected from oxo, halogen, CN, $C_{1-6}$ aliphatic, or -Q-Z.

In certain embodiments, R² is selected from R, halogen, —N(R)C(O)OR, or 1-imidazoyl substituted with R. In some embodiments, R² is halogen. In other embodiments, R² is R, wherein R is hydrogen. In still other embodiments, R² is R, wherein R is lower alkyl or lower haloalkyl. Exemplary R² groups include methyl, ethyl, trifluoromethyl, chloro, bromo, fluoro, and iodo. In certain embodiments, R² is trifluoromethyl.

According to some aspects, R¹ and R² are taken together with their intervening atoms to form a 5-7 membered saturated, partially unsaturated, or aryl ring having 0-3 heteroatoms independently selected from nitrogen, oxygen, or sulfur, wherein said ring is substituted with 1-3 groups independently selected from oxo, halogen, CN, $C_{1-6}$ aliphatic, or -Q-Z. In certain embodiments, R¹ and R² are taken together with their intervening atoms to form, together with the phenyl ring fused thereto, a naphthyl, tetrahydroquinoline, indoline, isoindoline, 1H-indole, or tetrahydroisoquinoline ring. In certain embodiments, R¹ and R² are taken together with their intervening atoms to form a naphthyl ring substituted with -Q-Z.

In certain embodiments, the ring formed by R¹ and R² is substituted with -Q-Z. In certain embodiments, the ring formed by R¹ and R² is substituted with —NHC(O)CH═CH₂, —C(O)CH═CH₂, or —CH₂N(CH₃)₂. In some embodiments, R¹ and R² are taken together with their intervening atoms to form a naphthyl ring substituted with —NHC(O)CH═CH₂.

As defined generally above, R³ is selected from hydrogen, lower alkyl, or halogen. In certain embodiments, R³ is lower alkyl. In some embodiments, R³ is methyl.

According to another aspect, the present invention provides a compound of formula III-a:

III-a or a pharmaceutically acceptable salt thereof, wherein:
W is CH or N;
each of R^a, R^b, R^c, and R^d is independently selected from R, OR, or halogen;
each R is independently hydrogen, lower alkyl, or lower haloalkyl;
R¹ is -L-Y, wherein:
L is a covalent bond or a bivalent $C_{1-8}$ saturated or unsaturated, straight or branched, hydrocarbon chain, wherein one, two, or three methylene units of L are optionally and independently replaced by —NR—, —N(R)C(O)—, —C(O)N(R)—, —O—, —C(O)—, —OC(O)—, —C(O)O—, —S—, —SO—, —SO₂—, —C(═S)—, —C(═NR)—, or —C(═N₂)—;

Y is hydrogen, $C_{1-6}$ aliphatic optionally substituted with oxo, halogen, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with at 1-4 groups independently selected from -Q-Z, oxo, halogen, CN, or $C_{1-6}$ aliphatic, wherein:

Q is a covalent bond or a bivalent $C_{1-6}$ saturated or unsaturated, straight or branched, hydrocarbon chain, wherein one or two methylene units of Q are optionally and independently replaced by —NR—, —S—, —O—, —C(O)—, —SO—, or —SO$_2$—; and Z is hydrogen or $C_{1-6}$ aliphatic optionally substituted with oxo, halogen, or CN;

$R^2$ is selected from R, halogen, —N(R)C(O)OR, or 1-imidazoyl substituted with R, or:

$R^1$ and $R^2$ are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group, wherein the warhead group is -Q-Z, and said ring is further substituted with 0-3 groups independently selected from oxo, halogen, CN, or $C_{1-6}$ aliphatic; and $R^3$ is selected from hydrogen, lower alkyl, or halogen.

In certain embodiments, each of the W, $R^a$, $R^b$, $R^c$, $R^d$, $R^1$, $R^2$, and $R^3$ groups of formula III-a is as defined above and described in classes and subclasses herein.

In certain embodiments, the $R^3$ group of formula III-a is lower alkyl.

As described herein, in certain embodiments, the W group of formula III-a is CH and in other embodiments, W is N. Thus, another embodiment of the present invention provides a compound of either of formulae III-b or III-c:

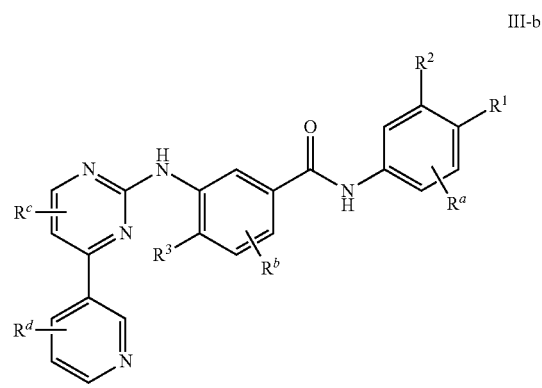

III-b

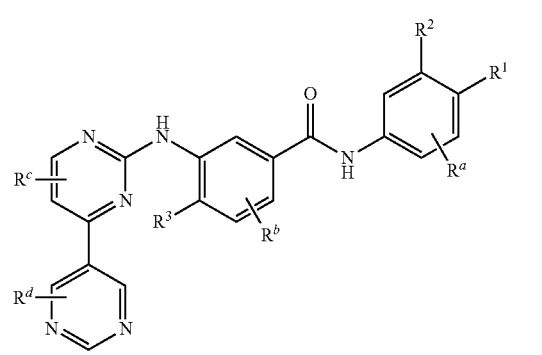

III-c or a pharmaceutically acceptable salt thereof, wherein each of $R^a$, $R^b$, $R^c$, $R^d$, $R^1$, $R^2$, and $R^3$ is as defined above and described in classes and subclasses herein.

Exemplary compounds of formula II are set forth in Table 3 below.

TABLE 3

Exemplary Compounds of Formula II

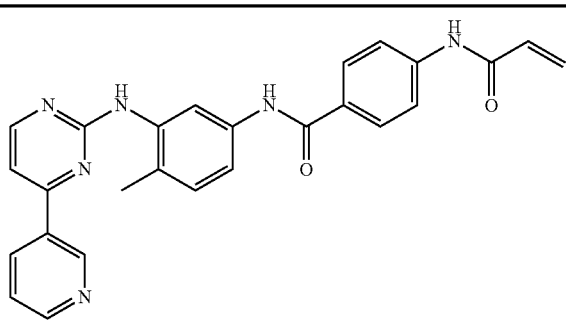

II-1

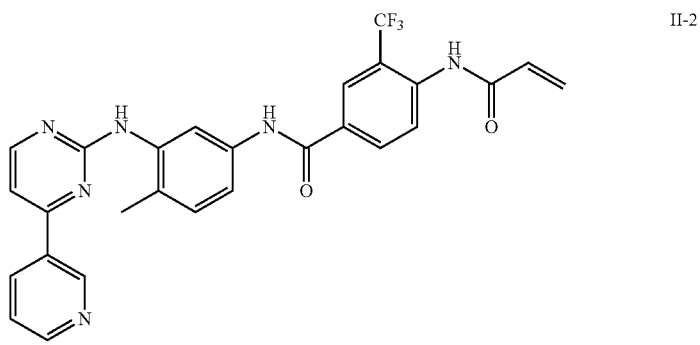

II-2

TABLE 3-continued
Exemplary Compounds of Formula II
II-3
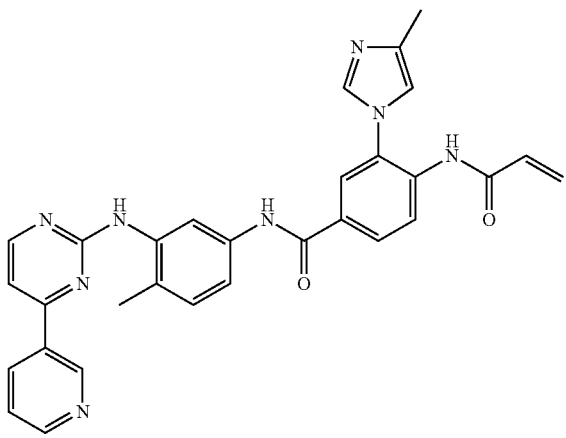 [SMILES: C=CC(=O)Nc1ccc(C(=O)Nc2ccc(C)c(Nc3nccc(-c4cccnc4)n3)c2)cc1-n1cnc(C)c1]
II-4
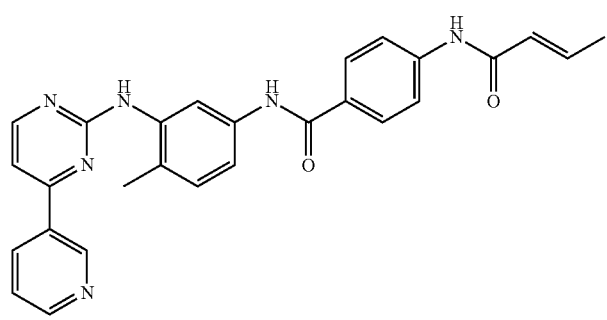 [SMILES: C/C=C/C(=O)Nc1ccc(C(=O)Nc2ccc(C)c(Nc3nccc(-c4cccnc4)n3)c2)cc1]
II-5
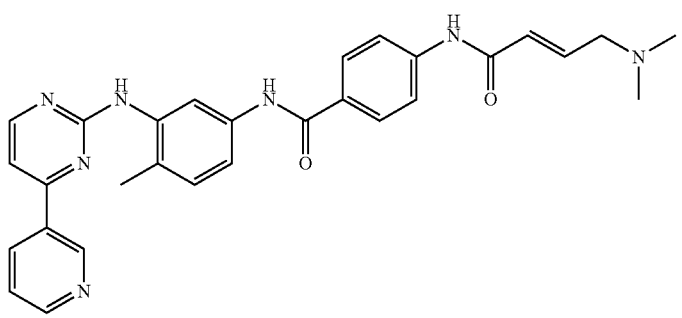
II-6
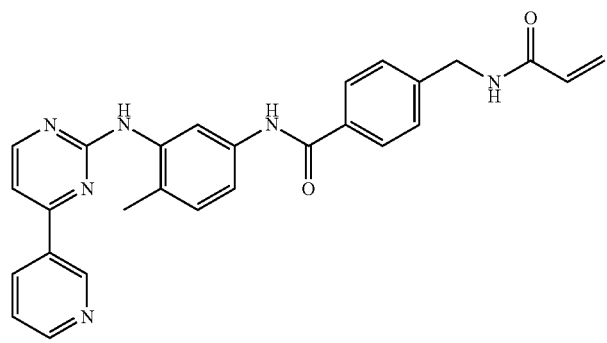 [SMILES: C=CC(=O)NCc1ccc(C(=O)Nc2ccc(C)c(Nc3nccc(-c4cccnc4)n3)c2)cc1]

TABLE 3-continued
Exemplary Compounds of Formula II
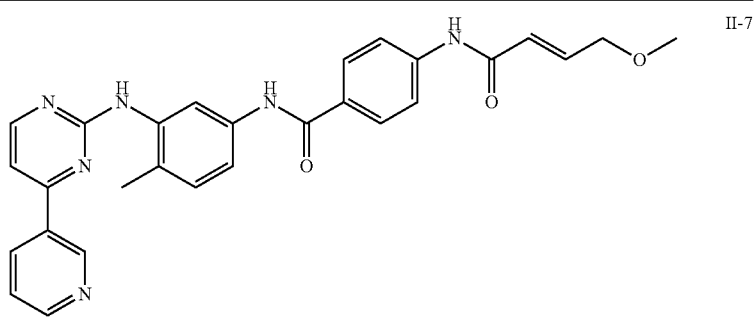
II-7
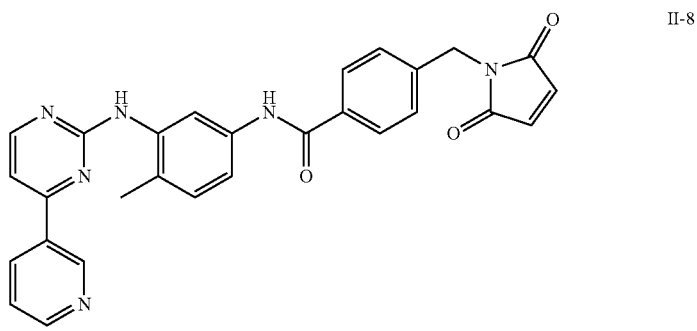
II-8
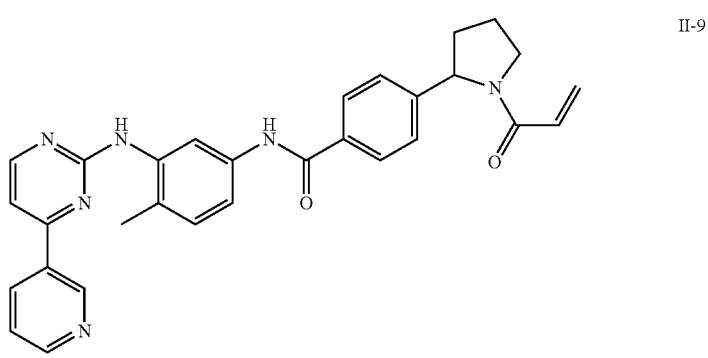
II-9
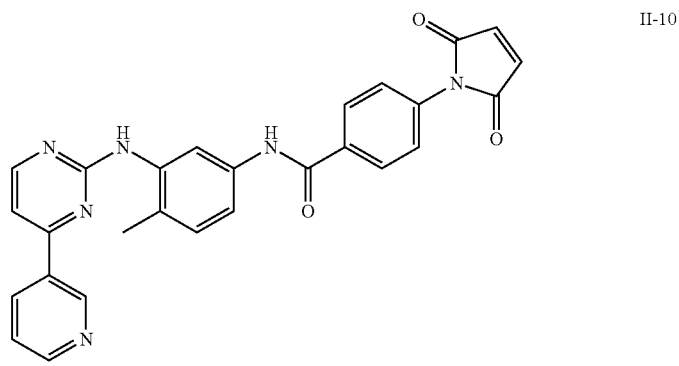
II-10

TABLE 3-continued
Exemplary Compounds of Formula II
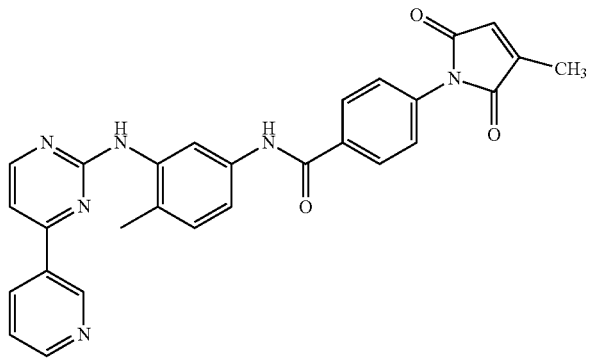 [SMILES: CC1=CC(=O)N(c2ccc(C(=O)Nc3ccc(C)c(Nc4nccc(-c5cccnc5)n4)c3)cc2)C1=O]
II-11
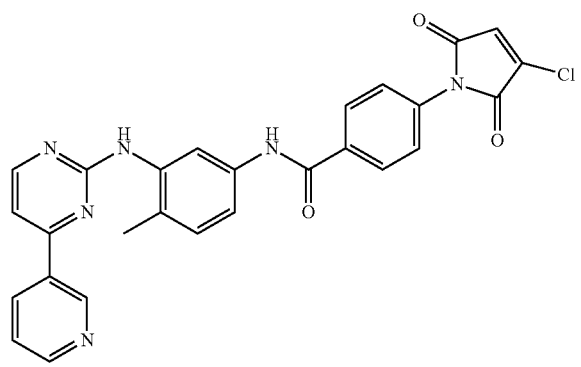 [SMILES: Cc1ccc(NC(=O)c2ccc(N3C(=O)C=C(Cl)C3=O)cc2)cc1Nc1nccc(-c2cccnc2)n1]
II-12
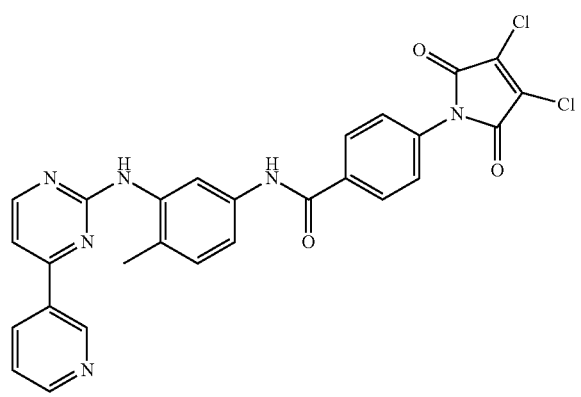 [SMILES: Cc1ccc(NC(=O)c2ccc(N3C(=O)C(Cl)=C(Cl)C3=O)cc2)cc1Nc1nccc(-c2cccnc2)n1]
II-13
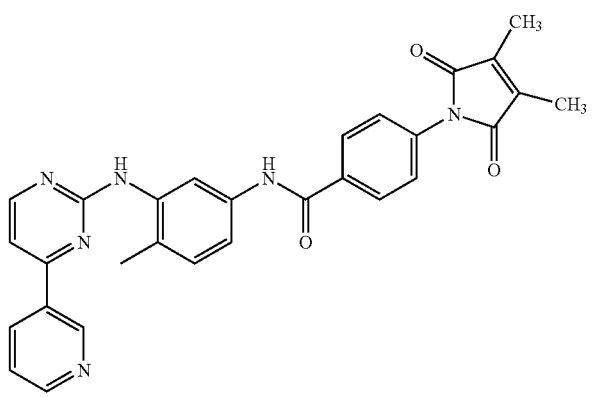 [SMILES: CC1=C(C)C(=O)N(c2ccc(C(=O)Nc3ccc(C)c(Nc4nccc(-c5cccnc5)n4)c3)cc2)C1=O]
II-14

TABLE 3-continued
Exemplary Compounds of Formula II
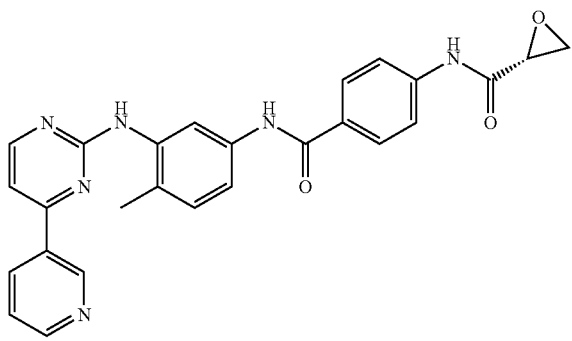 [SMILES: Cc1ccc(NC(=O)c2ccc(NC(=O)[C@H]3CO3)cc2)cc1Nc1nccc(-c2cccnc2)n1]
II-15
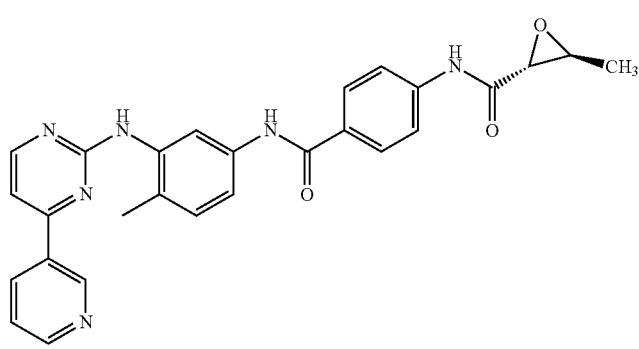 [SMILES: Cc1ccc(NC(=O)c2ccc(NC(=O)[C@@H]3O[C@H]3C)cc2)cc1Nc1nccc(-c2cccnc2)n1]
II-16
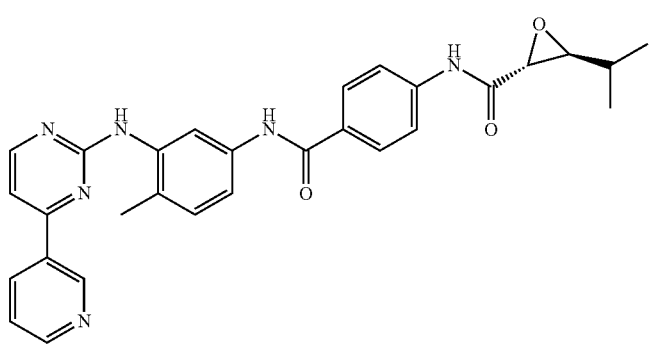 [SMILES: Cc1ccc(NC(=O)c2ccc(NC(=O)[C@@H]3O[C@H]3C(C)C)cc2)cc1Nc1nccc(-c2cccnc2)n1]
II-17
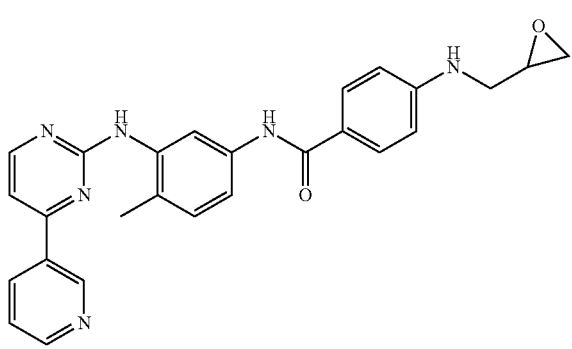 [SMILES: Cc1ccc(NC(=O)c2ccc(NCC3CO3)cc2)cc1Nc1nccc(-c2cccnc2)n1]
II-18

TABLE 3-continued
Exemplary Compounds of Formula II
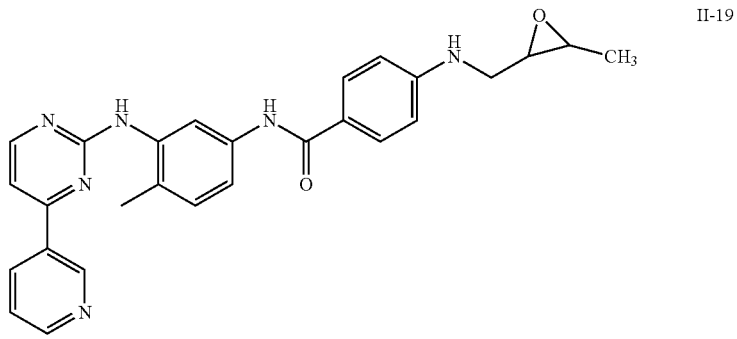
II-19
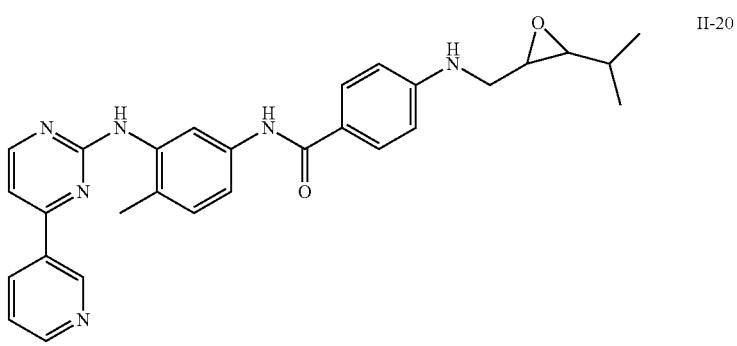
II-20
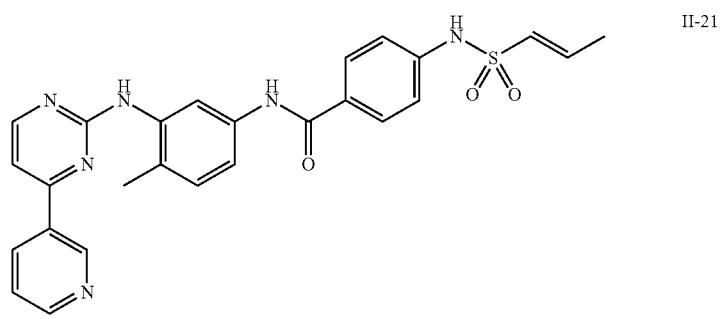
II-21
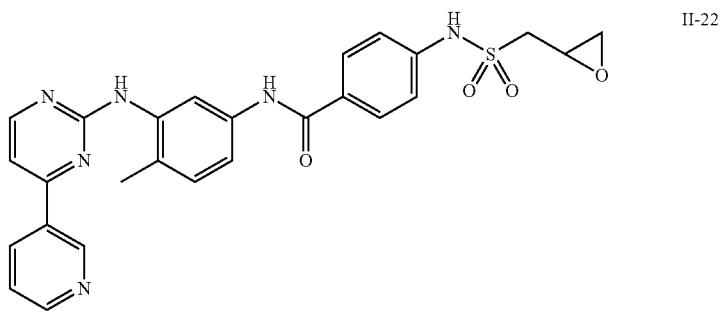
II-22

TABLE 3-continued
Exemplary Compounds of Formula II
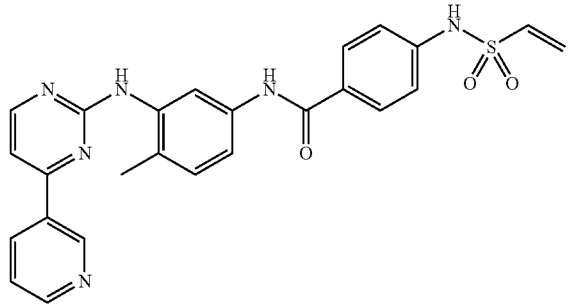 [SMILES: C=CS(=O)(=O)Nc1ccc(C(=O)Nc2ccc(C)c(Nc3nccc(-c4cccnc4)n3)c2)cc1]
II-23
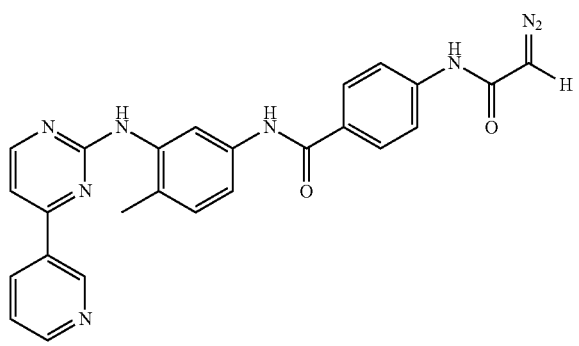
II-24
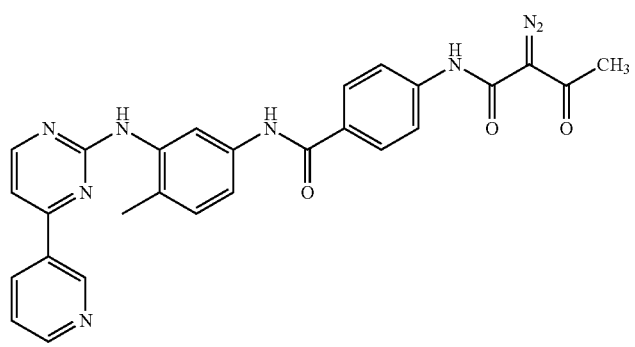
II-25
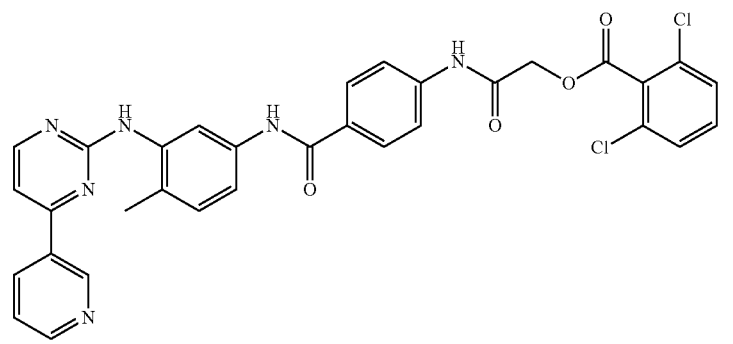 [SMILES: Cc1ccc(NC(=O)c2ccc(NC(=O)COC(=O)c3c(Cl)cccc3Cl)cc2)cc1Nc1nccc(-c2cccnc2)n1]
II-26

TABLE 3-continued
Exemplary Compounds of Formula II
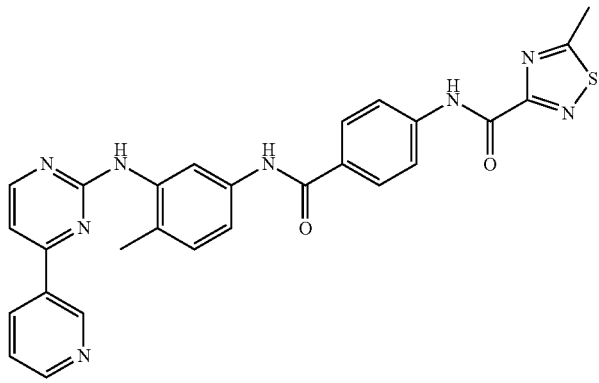 [SMILES: Cc1nc(C(=O)Nc2ccc(C(=O)Nc3ccc(C)c(Nc4nccc(-c5cccnc5)n4)c3)cc2)ns1]
II-27
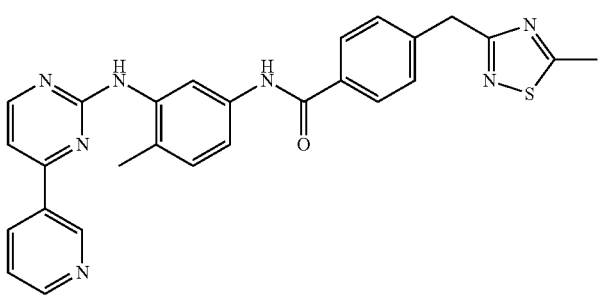 [SMILES: Cc1nc(Cc2ccc(C(=O)Nc3ccc(C)c(Nc4nccc(-c5cccnc5)n4)c3)cc2)ns1]
II-28
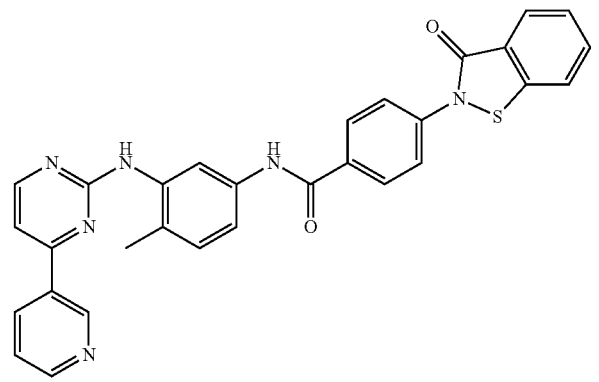 [SMILES: Cc1ccc(NC(=O)c2ccc(-n3sc4ccccc4c3=O)cc2)cc1Nc1nccc(-c2cccnc2)n1]
II-29
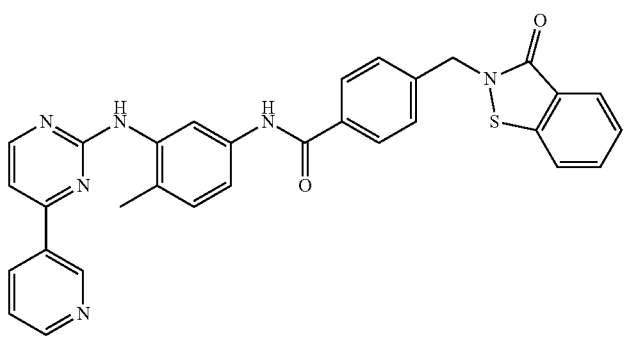 [SMILES: Cc1ccc(NC(=O)c2ccc(Cn3sc4ccccc4c3=O)cc2)cc1Nc1nccc(-c2cccnc2)n1]
II-30

TABLE 3-continued
Exemplary Compounds of Formula II
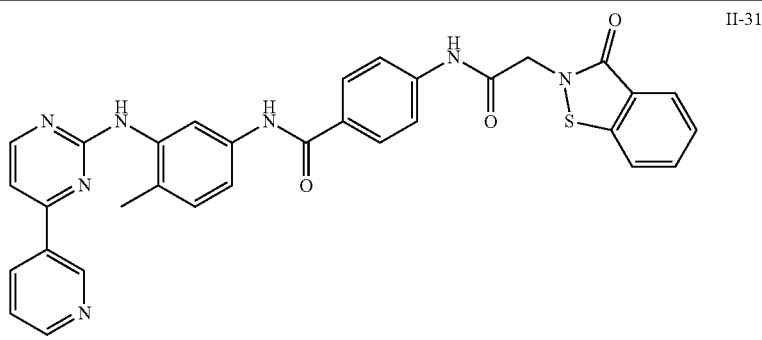
II-31
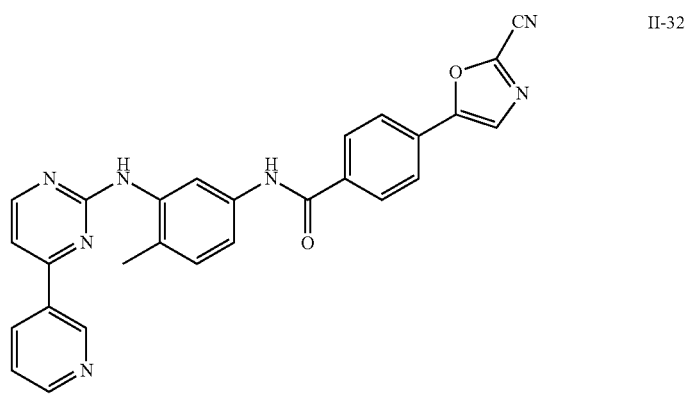
II-32
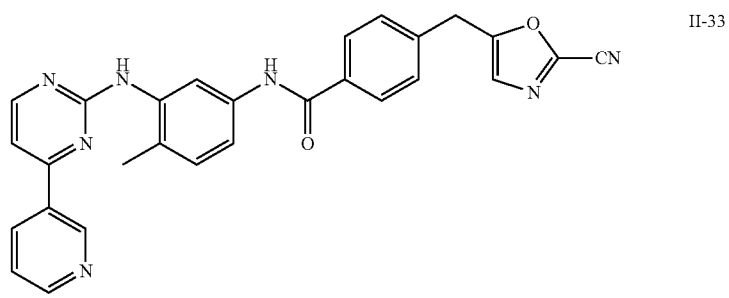
II-33
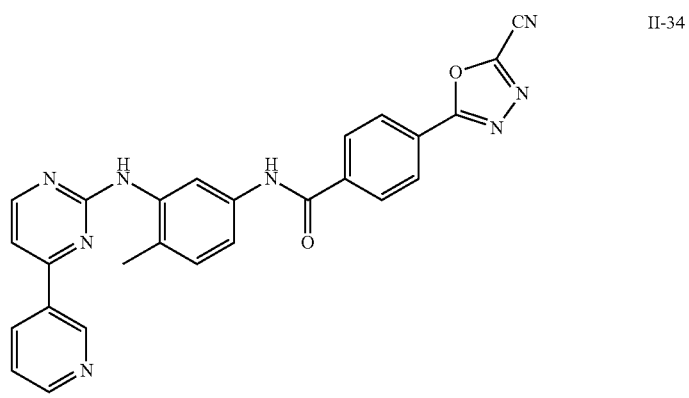
II-34

TABLE 3-continued
Exemplary Compounds of Formula II
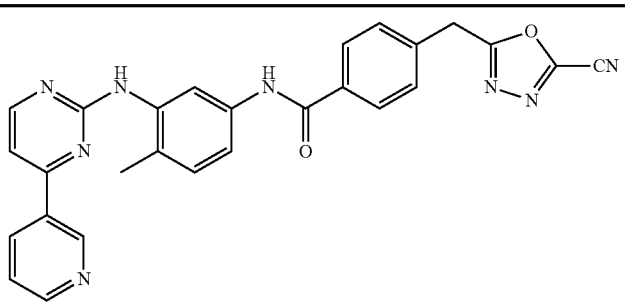
II-35
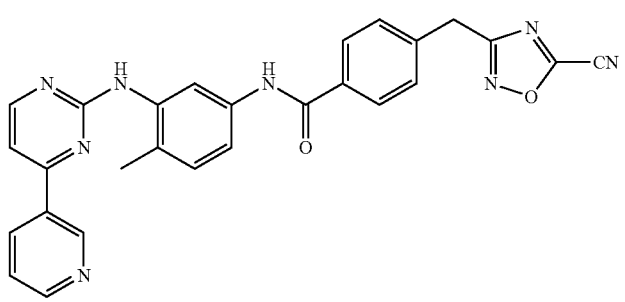 [SMILES: Cc1ccc(NC(=O)c2ccc(Cc3noc(C#N)n3)cc2)cc1Nc1nccc(-c2cccnc2)n1]
II-36
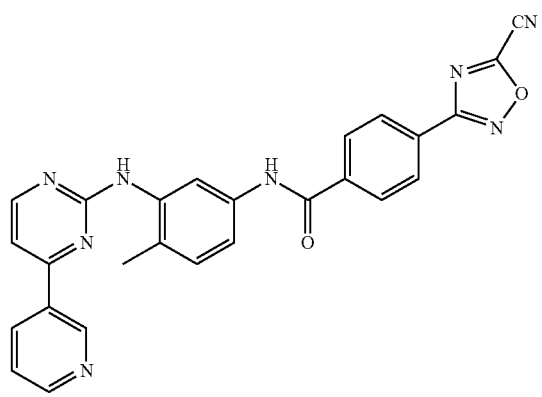 [SMILES: Cc1ccc(NC(=O)c2ccc(-c3noc(C#N)n3)cc2)cc1Nc1nccc(-c2cccnc2)n1]
II-37
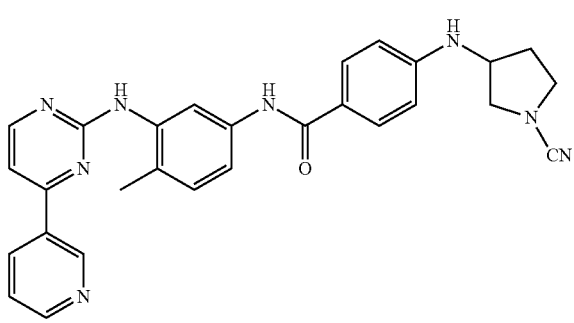 [SMILES: Cc1ccc(NC(=O)c2ccc(NC3CCN(C#N)C3)cc2)cc1Nc1nccc(-c2cccnc2)n1]
II-38

TABLE 3-continued
Exemplary Compounds of Formula II
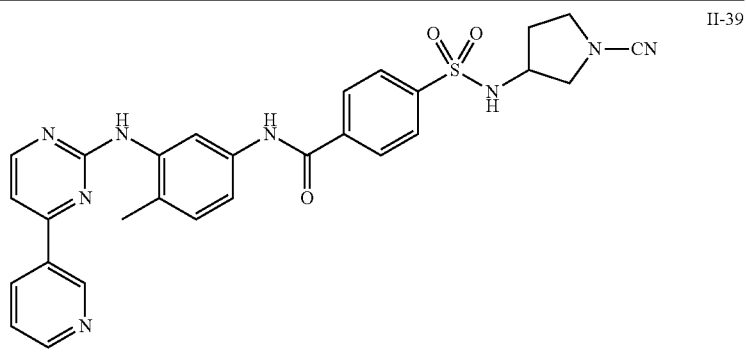
II-39
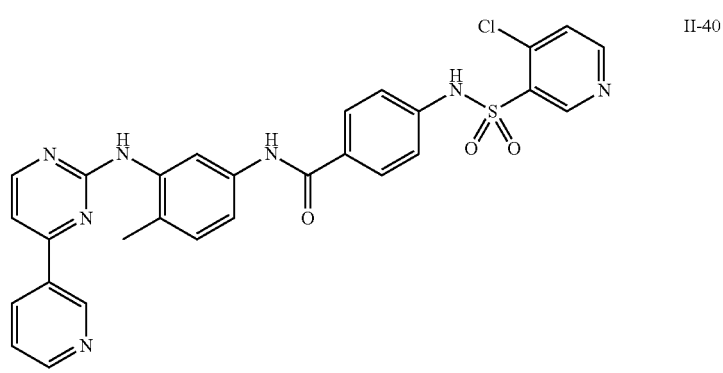
II-40
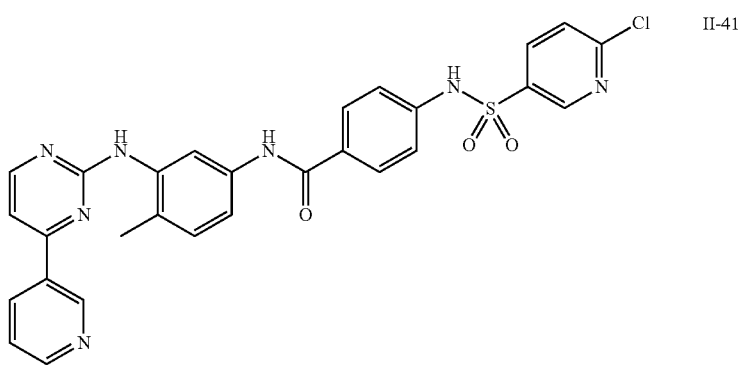
II-41
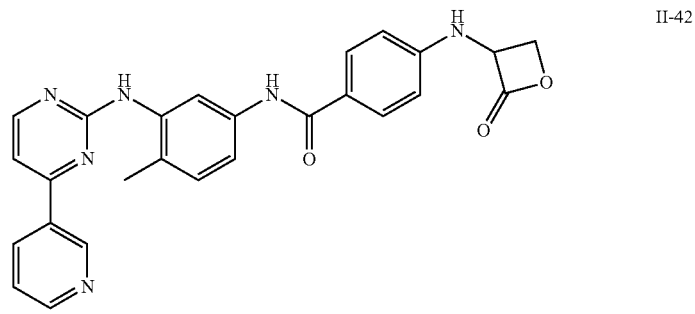
II-42

TABLE 3-continued
Exemplary Compounds of Formula II
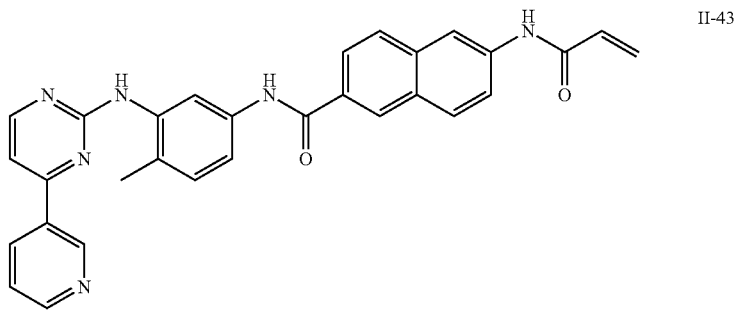
II-43
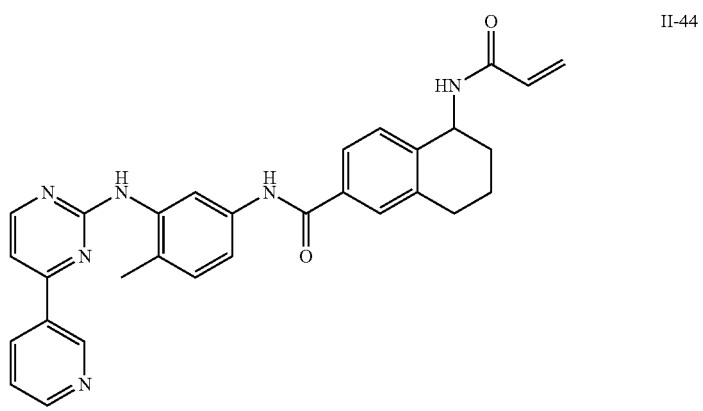
II-44
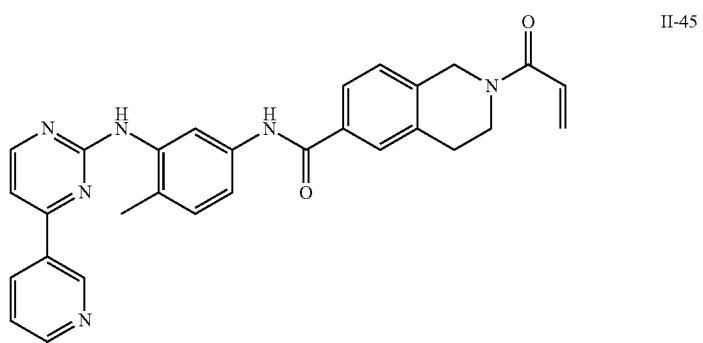
II-45
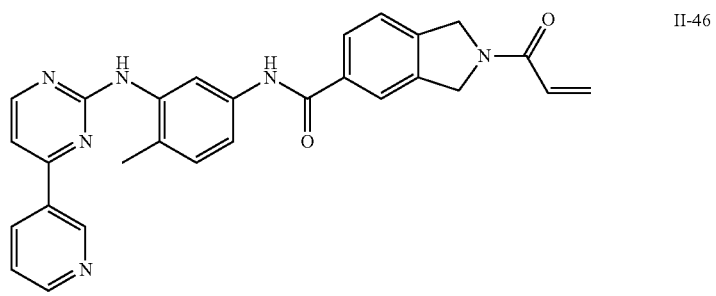
II-46

TABLE 3-continued
Exemplary Compounds of Formula II
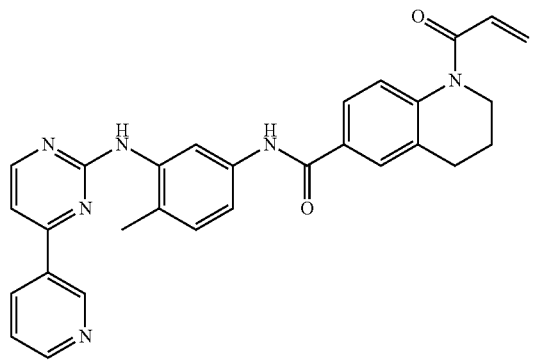 [SMILES: C=CC(=O)N1CCCc2cc(C(=O)Nc3ccc(C)c(Nc4nccc(-c5cccnc5)n4)c3)ccc21]
II-47
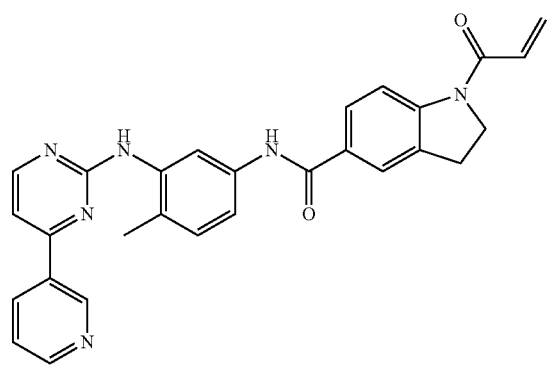 [SMILES: C=CC(=O)N1CCc2cc(C(=O)Nc3ccc(C)c(Nc4nccc(-c5cccnc5)n4)c3)ccc21]
II-48
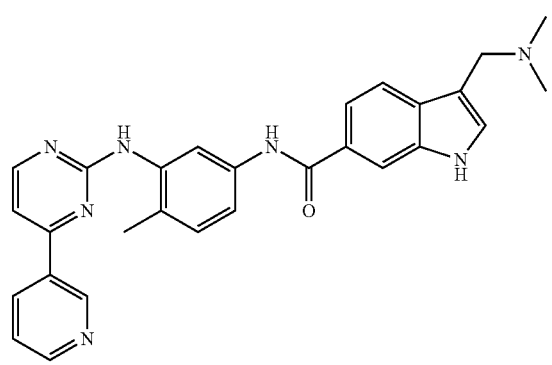 [SMILES: Cc1ccc(NC(=O)c2ccc3c(CN(C)C)c[nH]c3c2)cc1Nc1nccc(-c2cccnc2)n1]
II-49
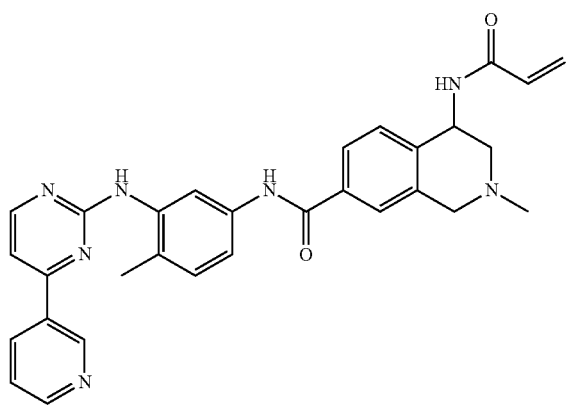 [SMILES: C=CC(=O)NC1CN(C)Cc2cc(C(=O)Nc3ccc(C)c(Nc4nccc(-c5cccnc5)n4)c3)ccc21]
II-50

TABLE 3-continued
Exemplary Compounds of Formula II
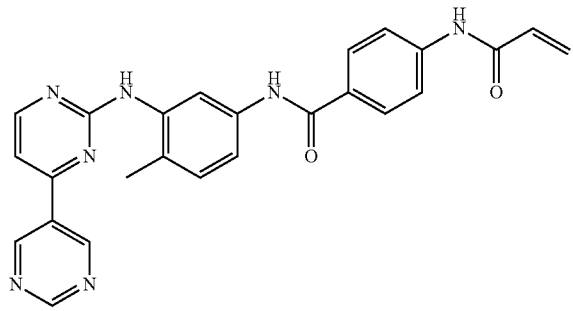 [SMILES: C=CC(=O)Nc1ccc(C(=O)Nc2ccc(C)c(Nc3nccc(-c4cncnc4)n3)c2)cc1]
II-51
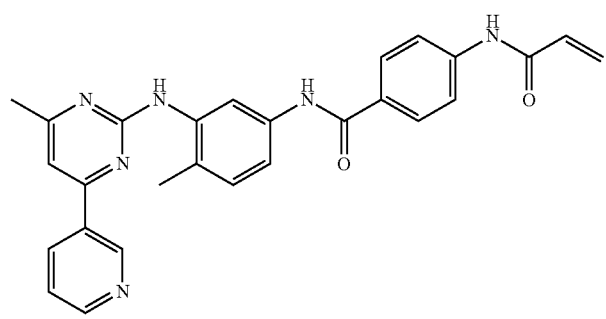 [SMILES: C=CC(=O)Nc1ccc(C(=O)Nc2ccc(C)c(Nc3nc(C)cc(-c4cccnc4)n3)c2)cc1]
II-52
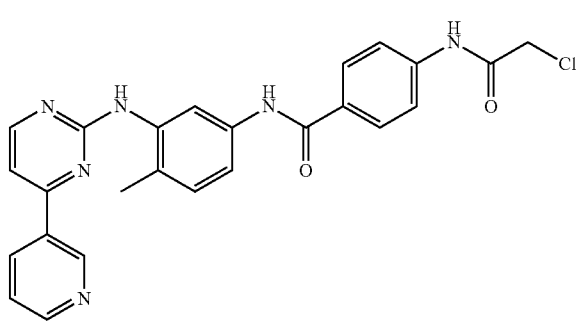 [SMILES: Cc1ccc(NC(=O)c2ccc(NC(=O)CCl)cc2)cc1Nc1nccc(-c2cccnc2)n1]
II-53
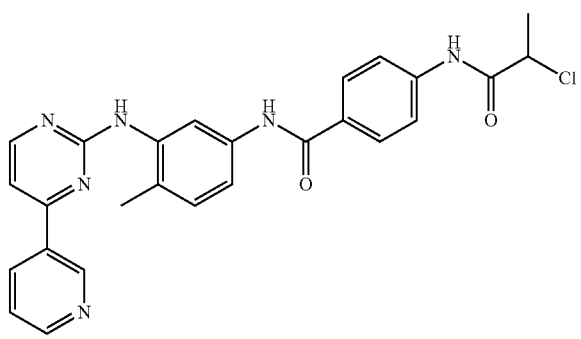 [SMILES: Cc1ccc(NC(=O)c2ccc(NC(=O)C(C)Cl)cc2)cc1Nc1nccc(-c2cccnc2)n1]
II-54

TABLE 3-continued
Exemplary Compounds of Formula II
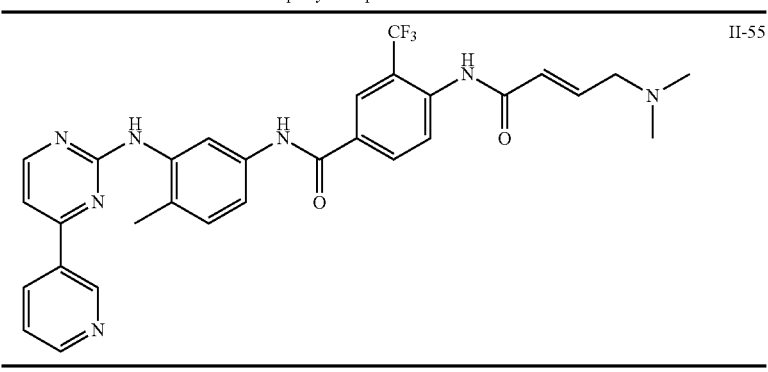
II-55
In certain embodiments, the present invention provides any compound depicted in Table 3, above, or a pharmaceutically acceptable salt thereof.
Exemplary compounds of formula III are set forth in Table 4, below.
TABLE 4
Exemplary Compounds of Formula III
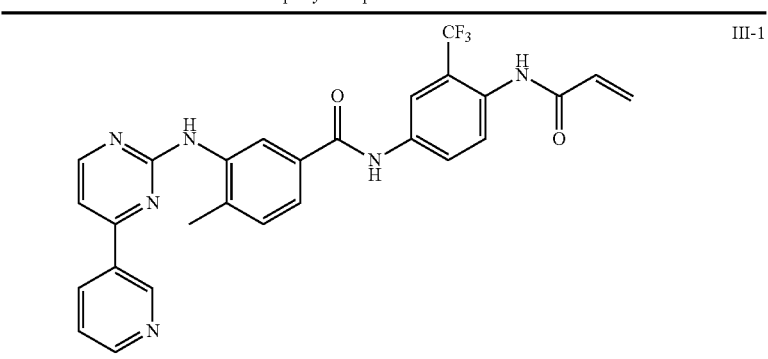
III-1
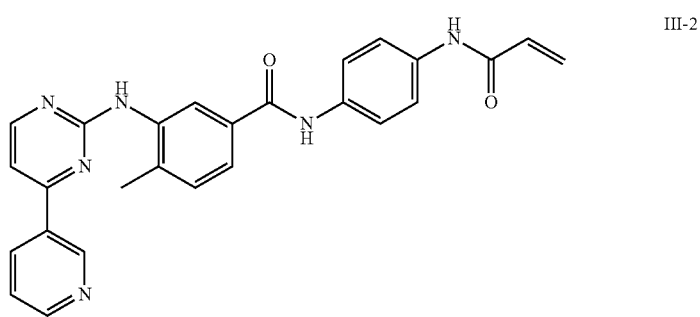
III-2
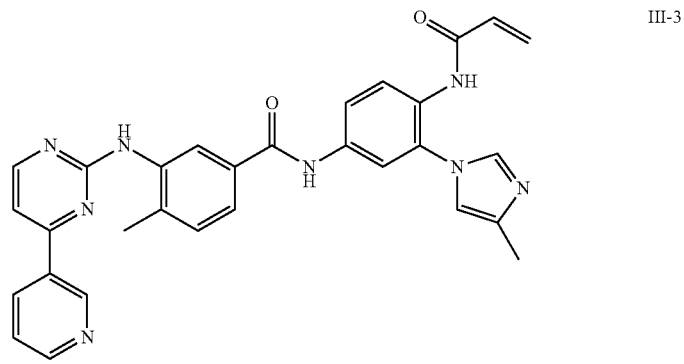
III-3

TABLE 4-continued
Exemplary Compounds of Formula III
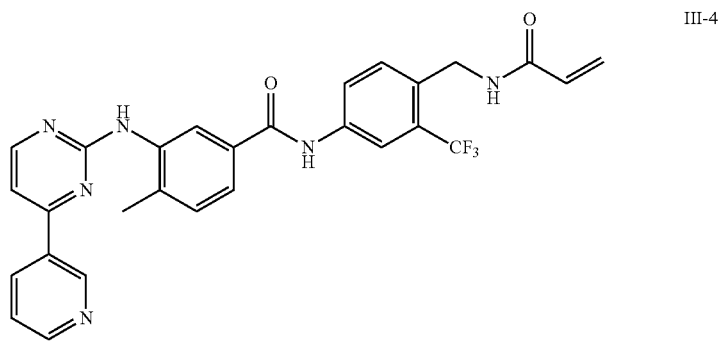
III-4
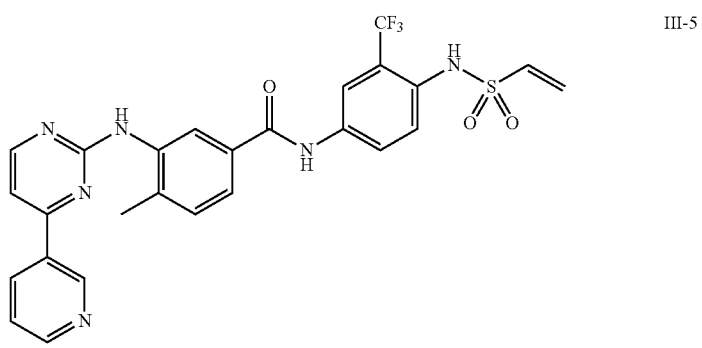
III-5
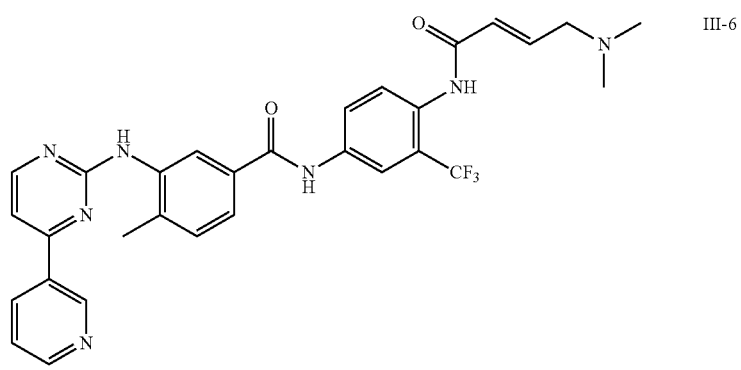
III-6
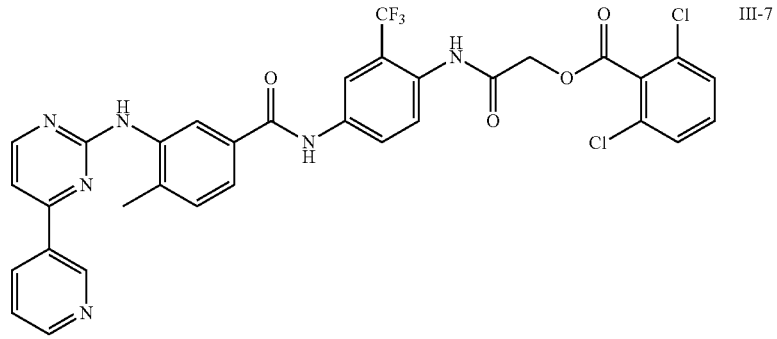
III-7

TABLE 4-continued
Exemplary Compounds of Formula III
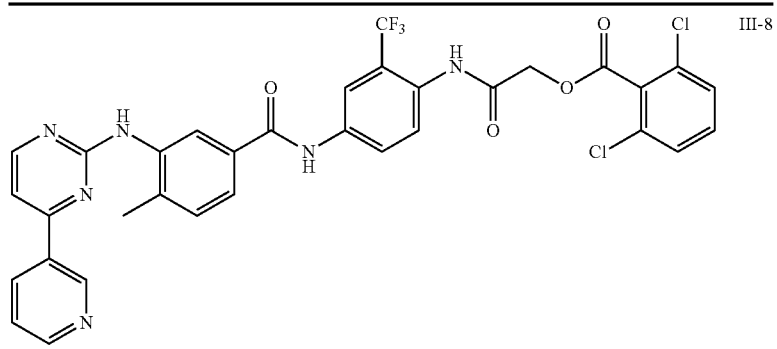
III-8
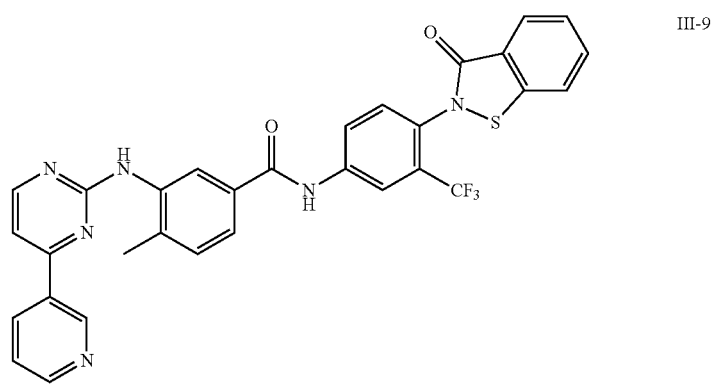
III-9
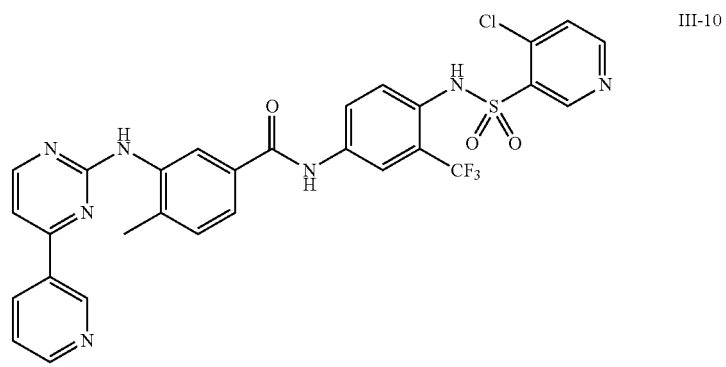
III-10
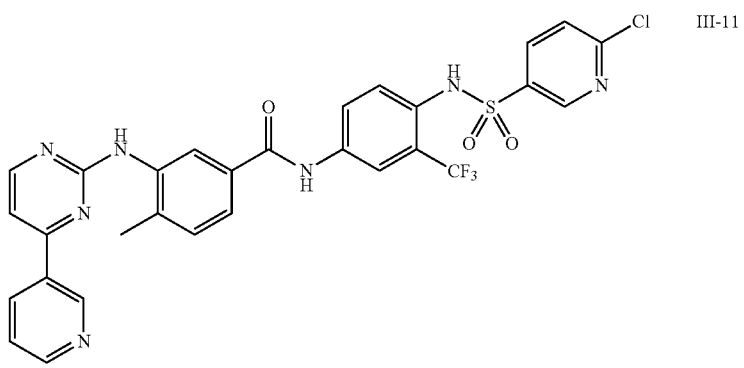
III-11

TABLE 4-continued
Exemplary Compounds of Formula III
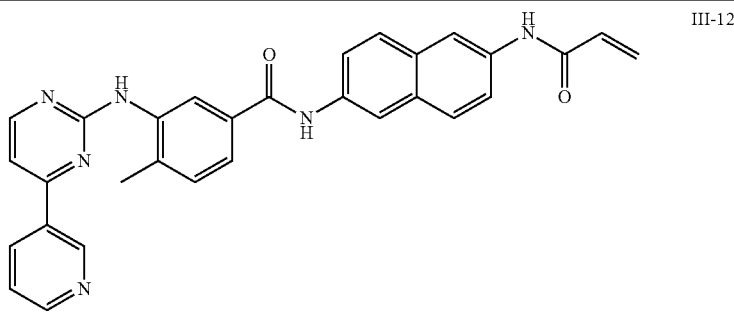
III-12
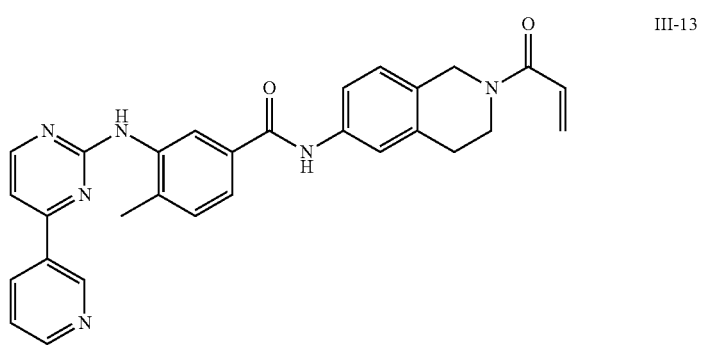
III-13
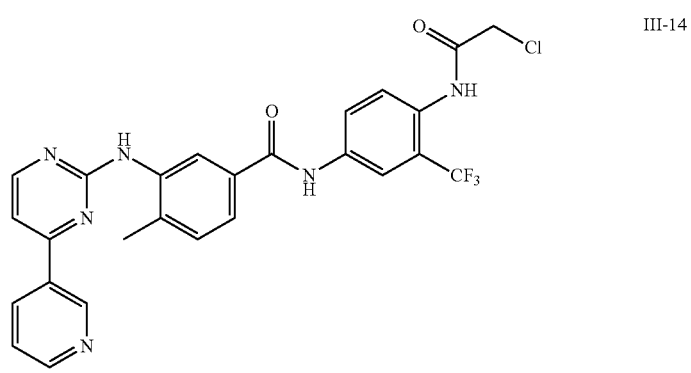
III-14
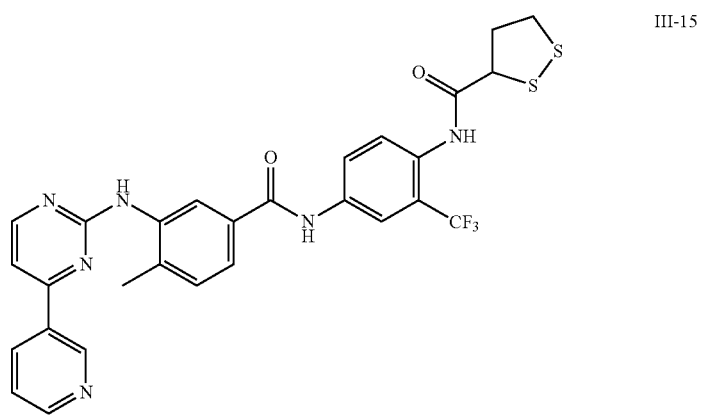
III-15

TABLE 4-continued
Exemplary Compounds of Formula III
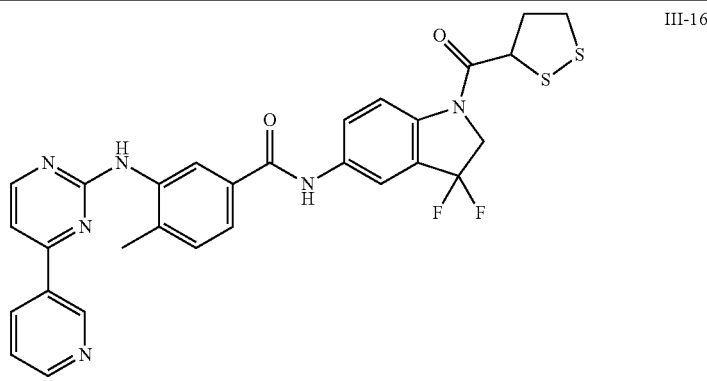
III-16
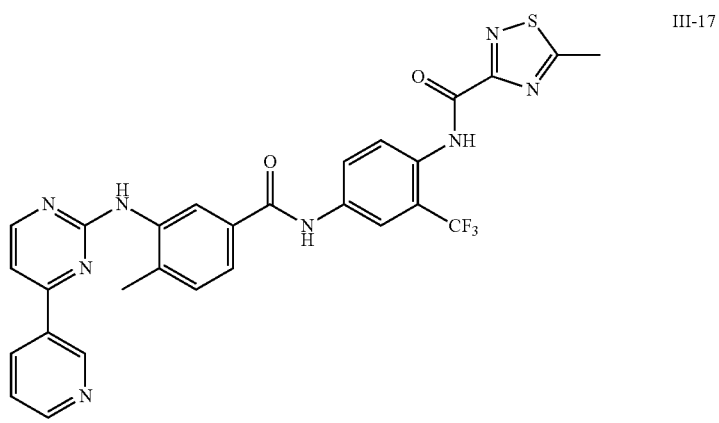
III-17
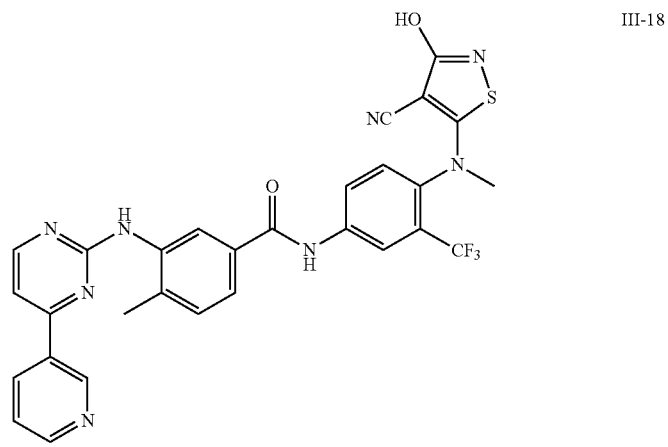
III-18
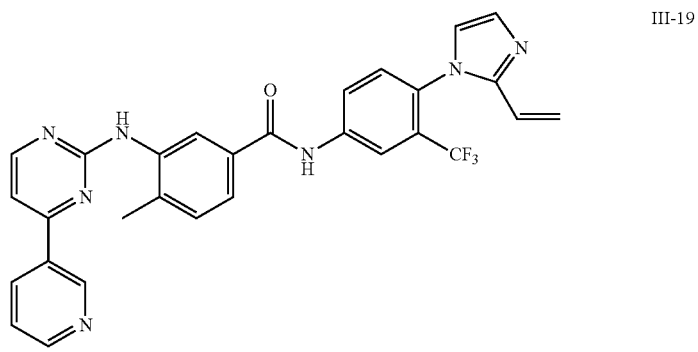
III-19

In certain embodiments, the present invention provides any compound depicted in Table 4, above, or a pharmaceutically acceptable salt thereof.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit a protein kinase, particularly PDGFR (alpha and beta), cKit, KDR, or cFMS, in a biological sample or in a patient. In certain embodiments, the amount of compound in compositions of this invention is such that is effective to measurably inhibit a protein kinase, particularly PDGFR (alpha and beta) and/or cKit, in a biological sample or in a patient. Preferably a composition of this invention is formulated for administration to a patient in need of such composition. Most preferably, a composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of PDGFR (alpha and beta), cKit, KDR, or cFMS.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N+(C_{1-4} alkyl)_4$ salts. This invention also envisions the quaternization of any basic nitrogen-containing groups of the compounds disclosed herein. Water or oil-soluble or dispersible products may be obtained by such quaternization.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of protein kinase activity of one or more enzymes. Further information relating to kinase structure, function and their role in disease or disease symptoms is available at the Protein Kinase Resource website (http://kinases.sdsc.edu/html/index.shtml).

Drug resistance is emerging as a significant challenge for targeted therapies. For example, drug resistance has been reported for Gleevec® and Iressa®, as well as several other kinase inhibitors in development. In addition, drug resistance has been reported for the cKit and PDGFR receptors. It has been reported that irreversible inhibitors may be effective against drug resistant forms of protein kinases (Kwak, E. L., R. Sordella, et al. (2005). "Irreversible inhibitors of the EGF receptor may circumvent acquired resistance to gefitinib." *PNAS* 102(21): 7665-7670.) Without wishing to be bound by any particular theory, it is believed that compounds of the present invention may be effective inhibitors of drug resistant forms of protein kinases.

As used herein, the term "clinical drug resistance" refers to the loss of susceptibility of a drug target to drug treatment as a consequence of mutations in the drug target As used herein, the term "resistance" refers to changes in the wild-type nucleic acid sequence coding a target protein, and/or the protein sequence of the target, which changes decrease or abolish the inhibitory effect of the inhibitor on the target protein.

Examples of kinases that are inhibited by the compounds and compositions described herein and against which the methods described herein are useful include PDGFR (alpha and beta), cKit, KDR, and cFMS.

The activity of a compound utilized in this invention as an inhibitor of PDGFR (alpha and beta), cKit, KDR, or cFMS, may be assayed in vitro, in vivo or in a cell line. In vitro assays include assays that determine inhibition of either the phosphorylation activity and/or the subsequent functional consequences, or ATPase activity of activated PDGFR (alpha and beta), cKit, KDR, or cFMS. Alternate in vitro assays quantitate the ability of the inhibitor to bind to PDGFR (alpha and beta), cKit, KDR, or cFMS. Inhibitor binding may be measured by radiolabelling the inhibitor prior to binding, isolating the inhibitor/PDGFR, inhibitor/cKit, inhibitor/KDR, or inhibitor/cFMS complex and determining the amount of radiolabel bound. Alternatively, inhibitor binding may be determined by running a competition experiment where new inhibitors are incubated with PDGFR (alpha and beta), cKit, KDR, or cFMS bound to known radioligands. Detailed conditions for assaying a compound utilized in this invention as an inhibitor of PDGFR (alpha and beta), cKit, KDR, or cFMS are set forth in the Examples below.

Tyrosine kinases are a class of enzymes that mediate intracellular signal transduction pathways. Abnormal activity of these kinases has been shown to contribute to cell proliferation, carcinogenesis and cell differentiation. Thus, agents that modulate the activity of tyrosine kinases are useful for preventing and treating proliferative diseases associated with these enzymes.

Platelet-derived growth factor receptor (PDGFR) is an important target in tumor cell proliferation, cell migration, and angiogenesis, and may mediate the high interstitial fluid pressure (IFP) of tumors. PDGFR signaling pathways have been implicated in the development and growth of solid tumors. Blockade of PDGFR receptors has been shown to inhibit angiogenesis, tumor vascular maturation and maintenance, and tumor cell proliferation leading to tumor regression.

Additionally, PDGFR signals induce expression of proangiogenic signals (including VEGF) in endothelial cells, further stimulating tumor angiogenesis. PDGFR is essential for regulating the proliferation and migration of pericytes to the tumor vessel in angiogenesis. Pericytes are smooth vascular muscle cells that, with the help of endothelial cells, provide a structure around which new blood vessels may be formed. The expression of PDGFR on pericytes is a key event involved in the maturation and survival of tumor vasculature. Additionally, emerging data suggest that PDGF receptors mediate the high IFP of tumors, which has been shown to be a barrier to the efficient uptake of chemotherapeutic drugs.

PDGF-receptor (PDGFR) has two subunits—PDGFR-α and PDGRR-β, which can form homo or heterodimers upon ligand binding. There are several PDGF ligands: AB, BB, CC and DD. PDGFR is expressed on early stem cells, mast cells, myeloid cells, mesenchymal cells and smooth muscle cells. Only PDGFR-β has been implicated in myeloid leukemias, usually as a translocation partner with Tel, Huntingtin interacting protein (HIP1) or Rabaptin. Recently it was shown that activation mutations in PDGFR-α kinase domain play an important role in gastrointestinal stromal tumors (GIST).

According to another embodiment, the invention provides a method for treating or lessening the severity of a PDGFR-mediated disease or condition in a patient comprising the step of administering to said patient a composition according to the present invention.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The term "PDGFR-mediated disease" or "condition", as used herein means any disease or other deleterious condition in which PDGFR is known to play a role. Accordingly, another embodiment of the present invention relates to treating or lessening the severity of one or more diseases in which PDGFR is known to play a role. Specifically, the present invention relates to a method of treating or lessening the severity of a disease or condition selected from a proliferative disorder, wherein said method comprises administering to a patient in need thereof a composition according to the present invention.

In certain embodiments, the present invention provides a method for inhibiting the growth of blood vessels. Such a method is useful for treating disorders associated with deregulated angiogenesis, such as diseases caused by ocular neovascularisation, including retinopathies, such as diabetic retinopathy or age-related macula degeneration, psoriasis, haemangioblastoma, such as haemangioma, mesangial cell proliferative disorders, such as chronic or acute renal diseases, e.g. diabetic nephropathy, malignant nephrosclerosis, thrombotic microangiopathy syndromes or transplant rejection. Such disorders also include inflammatory renal disease, such as glomerulonephritis, mesangioproliferative glomerulonephritis, haemolytic-uraemic syndrome, diabetic nephropathy, hypertensive nephrosclerosis, atheroma, arterial restenosis, autoimmune diseases, diabetes, endometriosis, chronic asthma, and neoplastic diseases (solid tumors, but also leukemias and other "liquid tumors"), such as breast cancer, cancer of the colon, lung cancer (e.g., small-cell lung cancer), cancer of the prostate or Kaposi's sarcoma. In some embodiments, the present invention provides a method of inhibiting the growth of tumours, including preventing the metastatic spread of tumors and the growth of micrometastases. In certain embodiments, the present invention provides a method for treating a leukemia.

According to another embodiment, the present invention relates to a method of treating the growth or metastasis of tumor/cancer cells; and carcinomas (e.g, squamous cell carcinomas, multiple myeloma, melanoma, glioma, glioblastomas, leukemia, sarcomas, leiomyomas, mesothelioma, GIST, and carcinomas of the lung, breast, ovary, cervix, liver, biliary tract, gastrointestinal tract, pancreas, prostate, and head and neck, wherein said method comprises administering to a patient in need thereof a compound of the present invention, or pharmaceutically acceptable composition thereof.

In certain embodiments, the present invention provides a method for the treatment of conditions which include an accumulation of excess extracellular matrix; a fibrotic condition (which can be induced by drug or radiation), e.g., scleroderma, lupus nephritis, connective tissue disease, wound healing, surgical scarring, spinal cord injury, CNS scarring, acute injury, pulmonary fibrosis (such as idiopathic pulmonary fibrosis and radiation-induced pulmonary fibrosis), chronic obstructive pulmonary disease, adult respirator/distress syndrome, acute lung injury, drug-induced lung injury, glomerulonephritis, diabetic nephropathy, hypertension-induced nephropathy, alimentary track or gastrointestinal fibrosis, renal fibrosis, hepatic or biliary fibrosis, liver cirrhosis, primary biliary cirrhosis, cirrhosis due to fatty liver disease (alcoholic and nonalcoholic steatosis), primary sclerosing cholangitis, restenosis, cardiac fibrosis, opthalmic scarring, fibrosclerosis, fibrotic cancers, fibroids, fibroma, fibroadenomas, fibrosarcomas, transplant arteriopathy, and keloid); and, other conditions such as cachexia, hypertension, ankylosing spondylitis, demyelination in multiple sclerosis, cerebral angiopathy and Alzheimer's disease, wherein said method comprises administering to a patient in need thereof a compound of the present invention, or pharmaceutically acceptable composition thereof.

Other embodiments provide a method for treating a hematopoietic or non-hematopoietic malignancy in a patient in need thereof, wherein said method comprises administering to a patient in need thereof a compound, of the present invention, or pharmaceutically acceptable composition thereof. In certain embodiments, the present invention provides a method for treating AML, chronic myelogenous leukemia (CML), mastocytosis, anaplastic large-cell lymphoma, ALL, gastrointestinal stromal tumor (GIST), T-cell lymphoma, adenoid cytsic carcinoma, angiosarcoma, endometrial carcinoma, small cell lung carcinoma, prostate cancer, ovarian cancer, breast carcinoma, thyroid carcinoma, malignant melanoma or colon carcinoma, wherein said method comprises administering to a patient in need thereof a compound of the present invention, or pharmaceutically acceptable composition thereof.

According to another aspect, the present invention provides a method for treating a disease or condition selected from cancer such as brain cancer, genitourinary tract cancer, lymphatic system cancer, stomach cancer, cancer of the larynx, lung cancer, pancreatic cancer, breast cancer, Kaposi's sarcoma, and leukemia; endometriosis, benign prostatic hyperplasia; vascular diseases such as restenosis and atherosclerosis; autoimmune diseases such as rheumatoid arthritis and psoriasis; ocular conditions such as proliferative or angiogenic retinopathy and macular degeneration; and inflammatory diseases such as contact dermatitis, asthma and delayed hypersensitivity reactions, wherein said method comprises administering to a patient in need thereof a compound of the present invention, or pharmaceutically acceptable composition thereof.

In certain embodiments, the present invention provides a method for treating a disease or condition selected from osteoporosis, rheumatoid arthritis patients, inflammatory bowel disease, glomerulonephritis, allograft rejection, and arteriosclerosis, and cancer, wherein said method comprises administering to a patient in need thereof a compound of the present invention, or pharmaceutically acceptable composition thereof.

A family of type III receptor tyrosine kinases including c-Kit plays an important role in the maintenance, growth and development of hematopoietic and non-hematopoietic cells. c-Kit regulates maintenance of stem cell/early progenitor pools as well the development of mature lymphoid and myeloid cells. Upon activation, the kinase domain induces autophosphorylation of the receptor as well as the phosphorylation of various cytoplasmic proteins that help propogate the activation signal leading to growth, differentiation and survival. Some of the downstream regulators of c-Kit receptor signaling include, PLCγ, PI3-kinase, Grb-2, SHIP and Src related kinases. Both receptor tyrosine kinases have been shown to play a role in a variety of hematopoietic and non-hematopoietic malignancies. Mutations that induce ligand independent activation of c-Kit have been implicated acute-myelogenous leukemia (AML), acute lymphocytic leukemia (ALL), mastocytosis and gastrointestinal stromal tumor (GIST). These mutations include single amino acid changes in the kinase domain or internal tandem duplications, point mutations or in-frame deletions of the juxtamembrane region of the receptors. In addition to activating mutations, ligand dependent (autocrine or paracrine) stimulation of over-expressed wild-type c-Kit can contribute to the malignant phenotype.

According to another embodiment, the invention provides a method for treating or lessening the severity of a cKit-mediated disease or condition in a patient comprising the step of administering to said patient a composition according to the present invention.

The term "cKit-mediated disease" or "condition", as used herein means any disease or other deleterious condition in which cKit is known to play a role. Accordingly, another embodiment of the present invention relates to treating or lessening the severity of one or more diseases in which cKit is known to play a role. Specifically, the present invention relates to a method of treating or lessening the severity of a disease or condition selected from a proliferative disorder, wherein said method comprises administering to a patient in need thereof a composition according to the present invention.

The term "c-KIT-mediated disease", as used herein means any disease or other deleterious condition in which a c-KIT family kinase is known to play a role. Such conditions include, without limitation, AML, chronic myelogenous leukemia (CML), mastocytosis, anaplastic large-cell lymphoma, ALL, gastrointestinal stromal tumor (GIST), T-cell lymphoma, adenoid cytsic carcinoma, angiosarcoma, endometrial carcinoma, small cell lung carcinoma, prostate cancer, ovarian cancer, breast carcinoma, thyroid carcinoma, malignant melanoma and colon carcinoma.

KDR is a tyrosine kinase receptor that also binds VEGF (vascular endothelial growth factor). The binding of VEGF to the KDR receptor leads to angiogenesis, which is the sprouting of capillaries from preexisting blood vessels. High levels of VEGF are found in various cancers causing tumor angiogenesis and permitting the rapid growth of cancerous cells. Therefore, suppressing VEGF activity is a way to inhibit tumor growth, and it has been shown that this can be achieved by inhibiting KDR receptor tyrosine kinase. For example inhibitors of the tyrosine kinase are reported to also suppress tumor vascularization and the growth of multiple tumors.

Examples of cancers that may be treated by such inhibitors include brain cancer, genitourinary tract cancer, lymphatic system cancer, stomach cancer, cancer of the larynx, lung cancer, pancreatic cancer, breast cancer, Kaposi's sarcoma, and leukemia. Other diseases and conditions associated with abnormal tyrosine kinase activity include vascular disease, autoimmune diseases, ocular conditions, and inflammatory diseases.

According to another embodiment, the invention provides a method for treating or lessening the severity of a KDR-mediated disease or condition in a patient comprising the step of administering to said patient a composition according to the present invention.

The term "KDR-mediated disease", as used herein means any disease or other deleterious condition in which a KDR family kinase is known to play a role. Accordingly, another embodiment of the present invention relates to treating or lessening the severity of one or more diseases in which KDR is known to play a role. Specifically, the present invention relates to a method of treating or lessening the severity of a disease or condition selected from cancer such as brain cancer, genitourinary tract cancer, lymphatic system cancer, stomach cancer, cancer of the larynx, lung cancer, pancreatic cancer, breast cancer, Kaposi's sarcoma, and leukemia; endometriosis, benign prostatic hyperplasia; vascular diseases such as restenosis and atherosclerosis; autoimmune diseases such as rheumatoid arthritis and psoriasis; ocular conditions such as proliferative or angiogenic retinopathy and macular degeneration; and inflammatory diseases such as contact dermatitis, asthma and delayed hypersensitivity reactions.

cFMS is the receptor for Colony-stimulating factor 1 (CSF-1) which promotes the survival, proliferation, and differentiation of mononuclear phagocyte lineages. CSF-1 exerts its activities by binding to cell-surface cFMS receptors, resulting in autophosphorylation by receptor cFMS kinase and a subsequent cascade of intracellular signals. Receptor expression in macrophage lineages is consistent with the ability of exogenous CSF-1 to increase cytokine production in mice after lipopolysaccharide (LPS) challenge, increase the production of monocytes and macrophages in mice, and exacerbate arthritis in mice and rats. Mice with a nonfunctional CSF-1 ligand or receptor are osteopetrotic, deficient in several macrophage populations, and have diminished response to inflammatory challenge.

The CSF-1-cFMS-receptor pathway is up-regulated in a number of human pathologies that involve chronic activation of tissue macrophage populations and, thus, could be a target for drug therapy. CSF-1 promotes osteoclast development and bone degradation in vitro and, thus, could contribute to the excessive osteoclast activity in osteoporosis and at sites of orthopedic implant failure. CSF-1 is elevated in the synovial fluid of rheumatoid arthritis patients, and synovial fibroblasts from rheumatoid arthritis patients produce high levels of CSF-1, suggesting a role for CSF-1 in joint degradation. Increases in CSF-1 production are also associated with the accumulation of tissue macrophages seen in inflammatory bowel disease, glomerulonephritis, allograft rejection, and arteriosclerosis. In addition, the growth of several tumor types is associated with overexpression of CSF-1 and cFMS receptor in cancer cells and/or tumor stroma.

The compounds and compositions, according to the method of the present invention, may be administered using any amount and any route of administration effective for treating or lessening the severity of cancer, an autoimmune disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting PDGFR (alpha and beta), cKit, KDR, or cFMS activity in a biological sample comprising the step of contacting said biological sample with a compound of this invention, or a composition comprising said compound. In certain embodiments, the invention relates to a method of irreversibly inhibiting PDGFR (alpha and beta), cKit, KDR, or cFMS activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of protein kinase, or a protein kinase selected from PDGFR (alpha and beta), cKit, KDR, or cFMS, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting one or more of PDGFR (alpha and beta), cKit, KDR, or cFMS activity in a patient comprising the step of administering to said patient a compound of the present invention, or a composition comprising said compound. According to certain embodiments, the invention relates to a method of irreversibly inhibiting one or more of PDGFR (alpha and beta), cKit, KDR, or cFMS activity in a patient comprising the step of administering to said patient a compound of the present invention, or a composition comprising said compound. In other embodiments, the present invention provides a method for treating a disorder mediated by one or more of PDGFR (alpha and beta), cKit, KDR, or cFMS, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents, which are normally administered to treat that condition, may also be present in the compositions of this invention. As used herein, additional therapeutic agents that are normally administered to treat a particular disease, or condition, are known as "appropriate for the disease, or condition, being treated".

For example, compounds of the present invention, or a pharmaceutically acceptable composition thereof, are administered in combination with chemotherapeutic agents to treat proliferative diseases and cancer. Examples of known chemotherapeutic agents include, but are not limited to, Adriamycin, dexamethasone, vincristine, cyclophosphamide, fluorouracil, topotecan, taxol, interferons, platinum derivatives, taxane (e.g., paclitaxel), vinca alkaloids (e.g., vinblastine), anthracyclines (e.g., doxorubicin), epipodophyllotoxins (e.g., etoposide), cisplatin, methotrexate, actinomycin D, actinomycin D, dolastatin 10, colchicine, emetine, trimetrexate, metoprine, cyclosporine, daunorubicin, teniposide, amphotericin, alkylating agents (e.g., chlorambucil), 5-fluorouracil, camptothecin, cisplatin, metronidazole, and Gleevec™, among others. In other embodiments, a compound of the present invention is administered in combination with a biologic agent, such as Avastin or VECTIBIX.

In certain embodiments, compounds of the present invention, or a pharmaceutically acceptable composition thereof, are administered in combination with an antiproliferative or chemotherapeutic agent selected from any one or more of Abarelix, aldesleukin, Aldesleukin, Alemtuzumab, Alitretinoin, Allopurinol, Altretamine, Amifostine, Anastrozole, Arsenic trioxide, Asparaginase, Azacitidine, BCG Live, Bevacuzimab, Avastin, Fluorouracil, Bexarotene, Bleomycin, Bortezomib, Busulfan, Calusterone, Capecitabine, Camptothecin, Carboplatin, Carmustine, Celecoxib, Cetuximab, Chlorambucil, Cisplatin, Cladribine, Clofarabine, Cyclophosphamide, Cytarabine, Dactinomycin, Darbepoetin alfa, Daunorubicin, Denileukin, Dexrazoxane, Docetaxel, Doxorubicin (neutral), Doxorubicin hydrochloride, Dromostanolone Propionate, Epirubicin, Epoetin alfa, Erlotinib, Estramustine, Etoposide Phosphate, Etoposide, Exemestane, Filgrastim, floxuridine fludarabine, Fulvestrant, Gefitinib, Gemcitabine, Gemtuzumab, Goserelin Acetate, Histrelin Acetate, Hydroxyurea, Ibritumomab, Idarubicin, Ifosfamide, Imatinib Mesylate, Interferon Alfa-2a, Interferon Alfa-2b, Irinotecan, Lenalidomide, Letrozole, Leucovorin, Leuprolide Acetate, Levamisole, Lomustine, Megestrol Acetate, Melphalan, Mercaptopurine, 6-MP, Mesna, Methotrexate, Methoxsalen, Mitomycin C, Mitotane, Mitoxantrone, Nandrolone, Nelarabine, Nofetumomab, Oprelvekin, Oxaliplatin, Paclitaxel, Palifermin, Pamidronate, Pegademase, Pegaspargase, Pegfilgrastim, Pemetrexed Disodium, Pentostatin, Pipobroman, Plicamycin, Porfimer Sodium, Procarbazine, Quinacrine, Rasburicase, Rituximab, Sargramostim, Sorafenib, Streptozocin, Sunitinib Maleate, Talc, Tamoxifen, Temozolomide, Teniposide, VM-26, Testolactone, Thioguanine, 6-TG, Thiotepa, Topotecan, Toremifene, Tositumomab, Trastuzumab, Tretinoin, ATRA, Uracil Mustard, Valrubicin, Vinblastine, Vincristine, Vinorelbine, Zoledronate, or Zoledronic acid.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and antiviral agents; agents for treating blood disorders such as corticosteroids, anti-leukemic agents, and growth factors; and agents for treating immunodeficiency disorders such as gamma globulin.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I, an additional therapeutic agent, and a pharmaceutically acceptable carrier, adjuvant, or vehicle.

The amount of both, an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

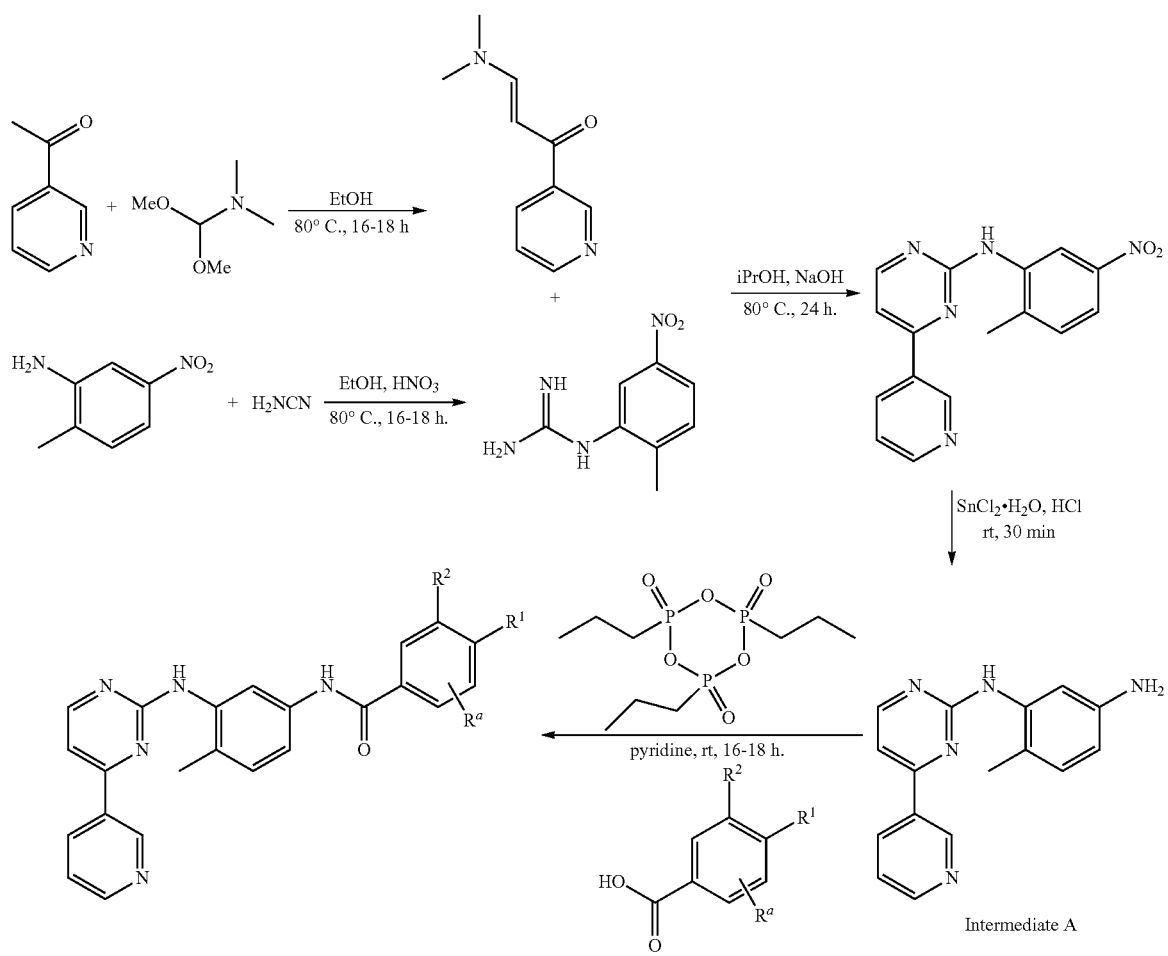

Intermediate A

Example 1

Synthesis of Intermediate A

Step 1: 3-Dimethylamino-1-pyridin-3-yl-propenone

3-Acetylpyridine (2.5 g, 20.64 mmol) and N,N-dimethylformamide dimethylacetal (3.20 ml, 24 mmol) were refluxed in ethanol (10 mL) overnight. The reaction mixture was cooled to room temperature and evaporated under reduced pressure. Diethyl ether (20 mL) was added to the residue and the mixture was cooled to 0° C. The mixture was filtered to give 3-dimethylamino-1-pyridin-3-yl-propenone (1.9 g, 10.78 mmol) as yellow crystals. (Yield: 52%.) This material was used in subsequent steps without further purification.

Step 2: N-(2-Methyl-5-nitro-phenyl)-guanidinium nitrate

2-Methyl-5-nitro aniline (10 g, 65 mmol) was dissolved in ethanol (25 mL), and concentrated HNO₃ (4.6 mL) was added to the solution dropwise followed by 50% aqueous solution of cyanamide (99 mmol). The reaction mixture was refluxed overnight and then cooled to 0° C. The mixture was filtered and the residue was washed with ethyl acetate and diethyl ether and dried to provide N-(2-Methyl-5-nitro-phenyl)-guanidinium nitrate (4.25 g, yield: 34%).

Step 3: 2-methyl-5-nitrophenyl-(4-pyridin-3-yl-pyrimidin-2-yl)-amine

To a suspension of 3-dimethylamino-1-pyridin-3-yl-propenone (1.70 g, 9.6 mmol) and N-(2-methyl-5-nitro-phenyl)-guanidinium nitrate (2.47 g, 9.6 mmol) in 2-propanol (20 mL) was added NaOH (430 mg, 10.75 mmol) and the resulting mixture was refluxed for 24 h. The reaction mixture was cooled to 0° C. and the resulting precipitate was filtered. The solid residue was suspended in water and filtered and then washed with 2-propanol and diethyl ether and dried. 0.87 g (2.83 mmol) of 2-methyl-5-nitrophenyl-(4-pyridin-3-yl-pyrimidin-2-yl)-amine was isolated. (Yield: 30%.)

Step 4: 4-Methyl-N-3-(4-pyridin-3-yl-pyrimidin-2-yl)-benzene-1,3-diamine (Intermediate A)

A solution of SnCl₂.2H₂O (2.14 g, 9.48 mmol) in concentrated hydrochloric acid (8 mL) was added to 2-methyl-5-nitro-phenyl-(4-pyridin-3-yl-pyrimidin-2-yl)-amine (0.61 g, 1.98 mmol) with vigorous stirring. After 30 min of stirring the mixture was poured onto crushed ice, made alkaline with K₂CO₃, and extracted three times with of ethyl acetate (50 ml). Organic phases were combined, dried over MgSO₄, and evaporated to dryness. Recrystallization from dichloromethane resulted in 252.6 mg (0.91 mmol) of 4-methyl-N-3-(4-pyridin-3-yl-pyrimidin-2-yl)-benzene-1,3-diamine (yield: 46%) as an off-white solid.

Example 1

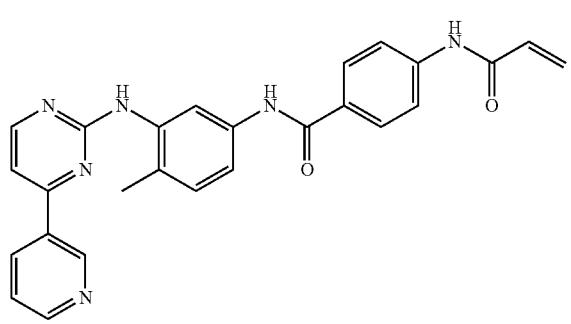

II-1

Step 1: 4-(acrylamido)benzoic acid

A solution of 4-aminobenzoic acid (1.40 g, 10 mmol) in DMF (10 mL) and pyridine (0.5 ml) was cooled to 0° C. To this solution was added of acryloyl chloride (0.94 g, 10 mmol) and the resulting mixture was stirred for 3 hours. The mixture was poured into 200 ml of water and the white solid obtained was filtered, washed with water and ether. Drying under high vacuum provided 1.8 g of the desired product which was used in the next step without purification.

Step 2

4-(Acrylamido)benzoic acid (82 mg, 0.43 mmol) and Intermediate A (100 mg, 0.36 mmol) were dissolved in pyridine (4 ml) under nitrogen and stirred. To this solution was added 1-propane phosphonic acid cyclic anhydride (0.28 g, 0.43 mmol) and the resulting solution was stirred overnight at room temperature. The solvent was evaporated to a small volume and then poured into a 50 ml of cold water. The solid formed was filtered and a yellow powder was obtained. Purification of the crude product by column chromatography (95:5 CHCl$_3$:MeOH) provided 30 mg of 4-acrylamido-N-(4-methyl-3-(4-(pyridin-3-yl)pyrimidin-2-ylamino)phenyl)benzamide (II-1) as a white powder. MS (M+H+): 251.2; $^1$H NMR (DMSO-D$_6$, 300 MHz) δ (ppm): 10.42 (s, 1H), 10.11 (s, 1H), 9.26 (d, 1H, J=2.2 Hz), 8.99 (s, 1H), 8.68 (dd, 1H, J=3.0 and 1.7 Hz), 8.51 (d, 1H, J=5.2 Hz), 8.48 (m, 1H), 8.07 (d, 1H, J=1.7 Hz), 7.95 (d, 2H, J=8.8 Hz), 7.79 (d, 2H, J=8.8 Hz), 7.45 (m, 3H), 7.19 (d, 1H, J=8.5 Hz), 6.47 (dd, 1H, J=16.7 and 9.6 Hz), 6.30 (dd, H, J=16.7 and 1.9 Hz), 5.81 (dd, 1H, J=9.9 and 2.2 Hz), 2.22 (s, 3H).

Example 2

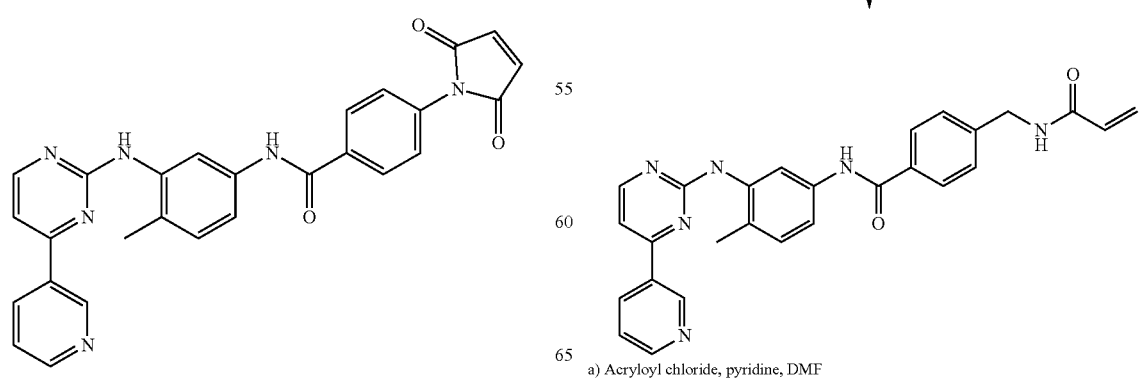

II-10

Compound II-10 can be synthesized from 4-(2,5-dioxo-2H-pyrrol-1(5H)-yl)benzoic acid and Intermediate A in substantially the same manner as described in Example 1. 4-Maleimidobenzoic acid is commercially available from multiple vendors.

Example 3

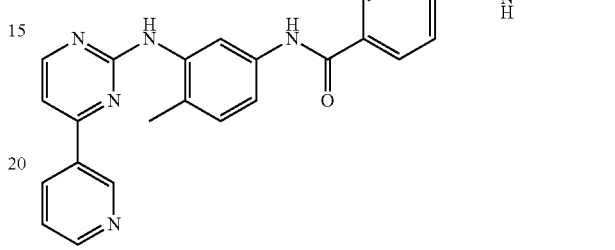

II6

Scheme 2

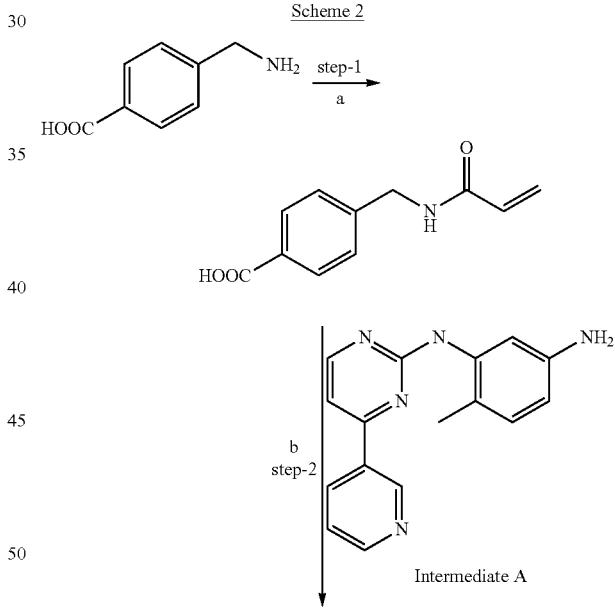

Intermediate A a) Acryloyl chloride, pyridine, DMF
b) BOP reagent, DIEA, CH$_3$CN, 16 h

Step-1: 4-(Acryloylaminomethyl)-benzoic acid

To a stirred solution of 4-aminomethyl benzoic acid (5 g, 33.0 mmol) and pyridine (1.5 mL) in DMF (35 mL) was added acryloyl chloride (2.97 g, 33.0 mmol) at 0° C. dropwise. The reaction mixture was allowed to come to room temperature and stirred further for 4 days. After that it was poured in water (100 mL) and stirred for 15 min and then extracted with EtOAc (3×150 mL). The combined organic extract was washed with brine (50 mL), dried over $Na_2SO_4$ and concentrated under reduced pressure to give crude product. Column chromatography (silica, 230-400, mixtures of $CHCl_3$/MeOH) provided the desired product (0.7 g, 9.95%) as a white solid which was used for next step.

Step-2: 4-(Acryloylaminomethyl)-N-[4-methyl-3-(4-pyridin-3-ylpyrimidin-2-ylamino)phenyl]benzamide (II-6)

To a solution of 4-(acryloylaminomethyl)-benzoic acid (75 mg, 0.37 mmol) in $CH_3CN$ (4 mL) was added BOP reagent (245 mg, 0.55 mmol), followed by DIEA (150 mg, 1.1 mmol) and Intermediate A (100 mg, 0.37 mmol). The reaction mixture was allowed to stir at rt for 16 h and then quenched with water (10 mL) and extracted with ethyl acetate (3×5 mL). The combined organic extract was washed with water (2 mL), brine (2 mL). Drying over $Na_2SO_4$ followed by concentration under reduced pressure gave crude product which was purified by column chromatography (silica, 230-400, mixtures of chloroform/methanol) to get II-6 (70 mg, 41%) as a white solid. MS (M+H$^+$): 464.5, 1H NMR (DMSO-d$_6$, 400 MHZ) δ (ppm): 2.20 (s, 3H), 4.40-4.42 (m, 2H), 5.62 (dd, J=2.2 & 10 Hz, 1H), 6.12 (dd, J=2.2 & 17 Hz, 1H), 6.26 (dd, J=10 & 17 Hz, 1H), 7.19 (d, J=8.2 Hz, 1H), 7.37-7.54 (m, 5H), 7.90 (d, J=8.2 Hz, 2H), 8.06 (s, 1H), 8.47-8.50 (m, 2H), 8.67-8.68 (m, 2H), 9.0 (s, 1H), 9.26 (s, 1H), 10.15 (s, 1H).

Example 4

II-8

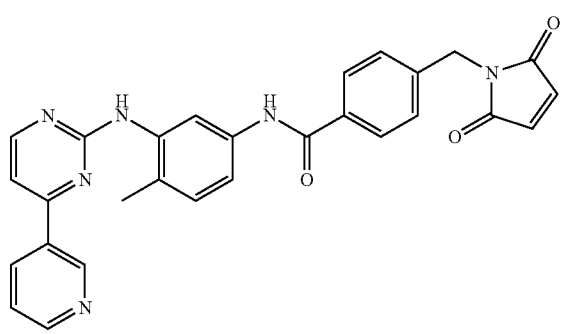

Scheme 3

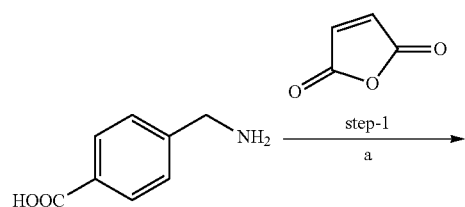

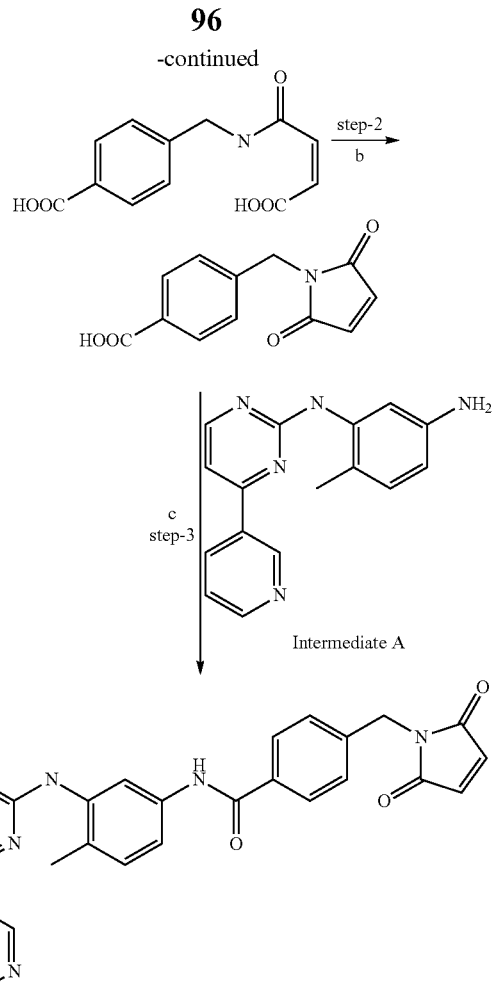

a) AcOH, rt, 18 h;
b) P$_2$O$_5$, dioxan, 100° C., 18 h;
c) BOP reagent, DIEA, DMF, rt, 16 h

Step-1: 4-[(3-carboxy acryloylamino)methyl]benzoic acid

To a solution of 4-aminobenzoic acid (1.54 g, 10.18 mmol) in acetic acid (20 mL) was added maleic anhydride (1 g, 10.10 mmol) and the reaction was stirred at room temperature for 18 h. A white solid precipitated out which was filtered, washed with water (3×5 mL) and dried to yield the desired product (2.3 g, 90%) as a white amorphous solid which was used as such for the next step.

Step-2: 4-(2,5-Dioxo-2,5-dihydropyrrol-1-methyl)benzoic acid

To a stirred solution of 4-[(3-carboxy acryloylamino)methyl]benzoic acid (1 g, 4.0 mmol) in dioxan (20 mL) was added $P_2O_5$ (0.84 g, 6.0 mmol) and the reaction mixture was refluxed for 18 h. Then the reaction mixture was cooled and solvents were removed on a rotatory evaporator under reduced pressure. The residue was taken in ice-cold water (5 mL) and the solution was extracted with EtOAc (3×50 mL). The combined EtOAc extract was washed with brine (25 mL), dried over $Na_2SO_4$ and concentrated under reduced pressure to yield 4-(2,5-dioxo-2,5-dihydropyrrol-1-methyl)benzoic acid (0.1 g, 10%) as a light cream colored solid which was used without further purification.

Step-3: 4-(2,5-Dioxo-2,5-dihydropyrrol-1-ylmethyl)-N-[4-methyl-3-(4-pyridin-3-yl-pyrimidin-2-ylamino)-phenyl]benzamide (II-8)

To a solution of 4-(2,5-dioxo-2,5-dihydropyrrol-1-methyl) benzoic acid (84 mg, 0.37 mmol) in DMF (2 mL) was added BOP reagent (240 mg, 0.54 mmol) and the reaction was stirred for 10 min. To it was added DIEA (140 mg, 1.08 mmol) and the reaction was further stirred for 10 min. Finally, Intermediate A (100 mg, 0.37 mmol) was added to it and reaction was allowed to stir at rt for 16 h. Then the reaction mixture was diluted with water (15 mL) and extracted with EtOAc (3×15 mL). The combined EtOAc extract was washed with brine (5 mL), dried ($Na_2SO_4$) and concentrated under reduced pressure to get 100 mg of the title compound as a crude solid. It was further purified by prep. HPLC to get pure II-8 (30 mg, 16.6%) as a light brown solid. MS (M+H$^+$): 490.1, 1H NMR (DMSO-$d_6$, 400 MHZ) δ (ppm): 2.20 (s, 3H), 4.66 (s, 2H), 7.10 (s, 2H), 7.19 (d, J=8.4 Hz, 1H), 7.35 (d, J=8.34 Hz, 2H), 7.41-7.52 (m, 3H), 7.88 (d, J=8.3 Hz, 2H), 8.05 (d, J=1.8 Hz, 1H), 8.45-8.50 (m, 2H), 8.66 (dd, J=1.5 & 4.7 Hz, 1H), 8.97 (s, 1H), 9.25 (s, 1H), 10.16 (s, 1H).

Example 5

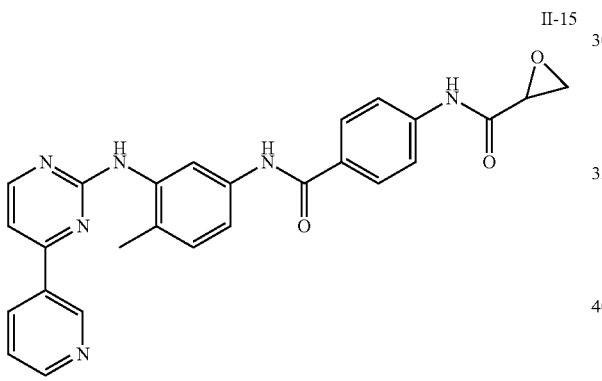

II-15

Compound II-15 can be synthesized by treating compound II-1 (prepared according to Example 1) with dimethyldioxirane in acetone using a protocol similar to that described in Bioorganic & Medicinal Chemistry 10 (2002) 355-360.

Example 6

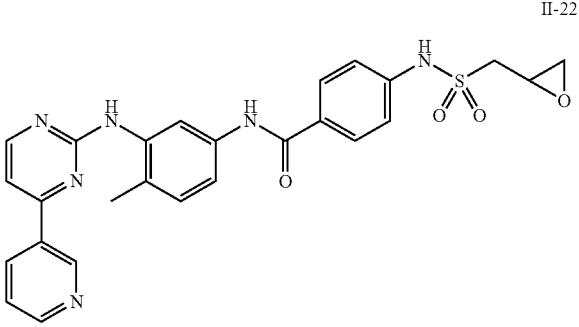 [SMILES: Cc1ccc(NC(=O)c2ccc(NS(=O)(=O)CC3CO3)cc2)cc1Nc1nccc(-c2cccnc2)n1]

II-22

Step 1

4-(Allylsulfonamido)benzoic acid can be prepared by treating 4-amino benzoic acid with commercially available prop-2-ene-1-sulfonyl chloride in a mixture of DMF and pyridine using the protocol in Example 1.

Step 2

4-(Allylsulfonamido)-N-(4-methyl-3-(4-(pyridin-3-yl) pyrimidin-2-ylamino)phenyl)benzamide can be prepared by treating Intermediate A and 4-(allylsulfonamido)benzoic acid in a manner substantially similar to that described in Example 1.

Step 3

Compound II-22 can be synthesized by treating 4-(Allylsulfonamido)-N-(4-methyl-3-(4-(pyridin-3-yl)pyrimidin-2-ylamino)phenyl)benzamide with dimethyldioxirane in acetone using a protocol similar to that described in Bioorganic & Medicinal Chemistry 10 (2002) 355-360.

Example 7

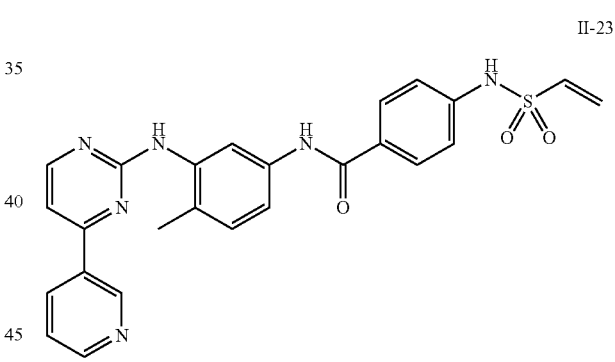

II-23

Step 1

Ethenesulfonyl chloride can be prepared from commercially available 2-chloroethanesulfonyl chloride in the presence of triethylamine using a protocol substantially similar to that described in Canadian Journal of Chemistry (1984), 62(10), 1977-95.

Step 2

4-(Vinylsulfonamido)benzoic acid can be synthesized by treating 4-(aminomethyl)benzoic acid with ethenesulfonyl chloride in a mixture of DMF and pyridine in a manner substantially similar to that described in Example 1.

99

Step 3

Compound II-23 can be synthesized from 4-(vinylsulfonamido)benzoic acid and Intermediate A using the same reaction conditions as in Example 1.

Example 8

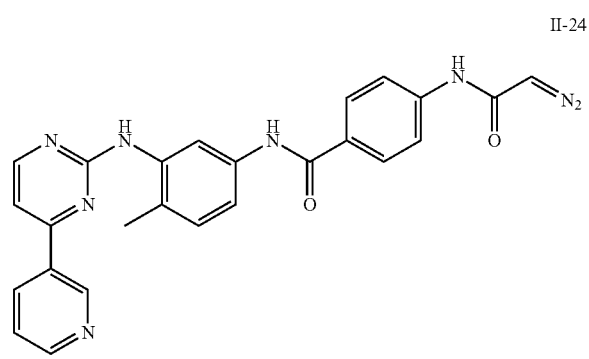

II-24

Step 1

2-(2-Tosylhydrazono)acetic acid can be prepared by treating glyoxalic acid with 4-methylbenzenesulfonohydrazide in a mixture of HCl and water using the protocol described in Organic Syntheses, 49, 22-7; 1969

100

Step 2

Treatment of commercially available tert-butyl 4-aminobenzoate with 2-(2-tosylhydrazono)acetic acid in the presence of DCC in THF followed by deprotection of the carboxylic acid with trifluoroacetic acid can provide 4-[[[(4-methylphenyl)sulfonyl]hydrazono]acetylamino]benzoic acid (protocol similar to that described Tetrahedron Letters, 33(38), 5509-10; 1992)

Step 3

Coupling of 4-[[[(4-methylphenyl)sulfonyl]hydrazono]acetylamino]benzoic acid and Intermediate A in the presence of DCC in THF followed by treatment with triethyl amine can provide compound II-24 (protocol similar to that described Tetrahedron Letters, 33(38), 5509-10; 1992)

Example 9

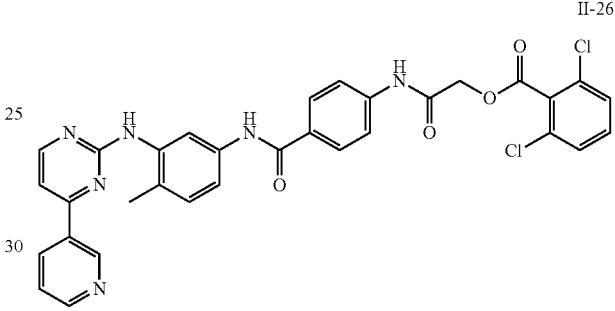

II-26

Scheme 4

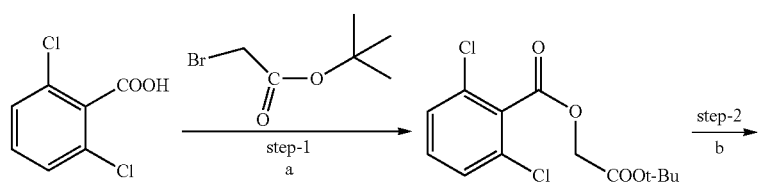

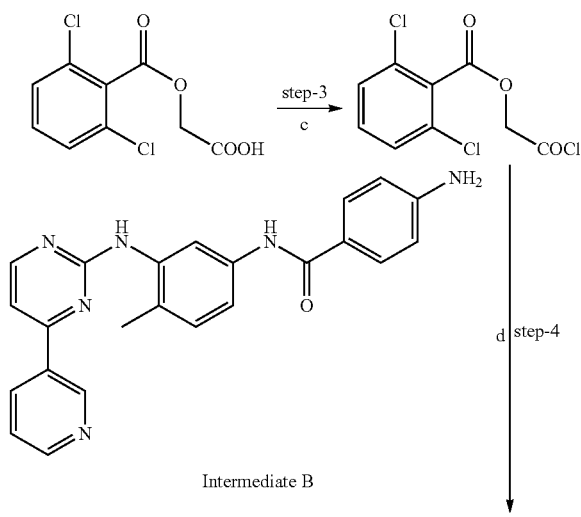

Intermediate B

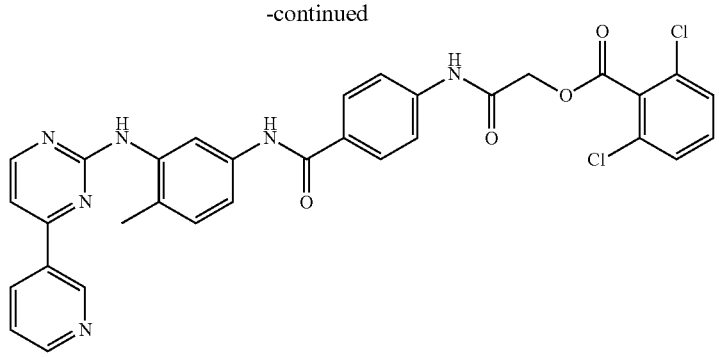

II-26 a) K$_2$CO$_3$, acetone, rt, 16 h;
b) TFA/DCM, 0° C. to rt, 16 h;
c) SOCl$_2$, Cat. DMF, CH$_2$Cl$_2$, 45° C., 3 h;
d) Et$_3$N, CH$_2$Cl$_2$, 0 to 10° C., 1.5 h.

Step-1

To a stirred solution of 2,6-dichlorobenzoic acid (0.20 g, 1.05 mmol) in acetone (10 mL) was added bromo ester (0.25 g, 1.25 mmol) and the reaction was allowed to stir at rt for 16 h. It was then filtered, filtrate concentrated to get a residue which on trituration with petroleum ether offered the corresponding diester as a white crystalline solid. Filtration, followed by drying gave the diester (0.29 g, 91%) as a white solid which was used for next step.

Step-2

The diester (0.26 g, 0.85 mmol) was dissolved in CH$_2$Cl$_2$ (5.0 mL) and to it was added trifluoroacetic acid (0.39 g, 3.38 mmol) at 0° C. The reaction mixture was allowed to come to rt and further stirred for 12 h at rt. It was then concentrated to the corresponding acid (0.2 g, 95.3%) as a white solid.

Step-3

To a stirred suspension of acid (0.15 g, 0.80 mmol) in CH$_2$Cl$_2$ (3.0 mL) was added DMF (1 drop) followed by SOCl$_2$ (0.14 g, 1.2 mmol). The reaction mixture was heated at 45° C. for 3 h, cooled and concentrated under reduced pressure to give the acid chloride which was used as such for the next step without further purifications.

Step-4

To a stirred suspension of the acid chloride (HCl salt, 0.1 g, 0.2 mmol) in CH$_2$Cl$_2$ (3.0 mL) was added Et$_3$N (0.12 g, 1.1 mmol) at 0° C. To it was added freshly prepared Intermediate B (0.33 g, 1.3 mmol, crude) and the reaction mixture was allowed to stir at 0° C. to 10° C. for 1.5 h. After completion of the reaction (TLC) the reaction was quenched with water (1 mL) and extracted with CH$_2$Cl$_2$ (3×5 mL). The combined CH$_2$Cl$_2$ extract was washed with water (2 mL), brine (2 mL), dried (Na$_2$SO$_4$) and concentrated under reduced pressure to get crude II-26 which was purified further by preparative HPLC to get pure II-26 (0.07 g, 48%) as a yellow solid. LC/MS (M+H$^+$): 627, 1H NMR (CD$_3$OD, 400 MHZ) δ (ppm): 2.21 (s, 3H), 5.01 (s, 2H), 7.19 (d, J=8.48 Hz, 1H), 7.42-7.64 (m, 6H), 7.73 (d, J=8.76 Hz, 2H), 7.95 (d, J=8.76 Hz, 2H), 8.06 (d, J=1.8 Hz, 1H), 8.46-8.51 (m, 2H), 8.67 (dd, J=1.2 & 4.68 Hz, 1H), 9.0 (s, 1H), 9.28 (s, 1H), 10.1 (s, 1H), 10.52 (s, 1H).

Synthesis of Intermediate B

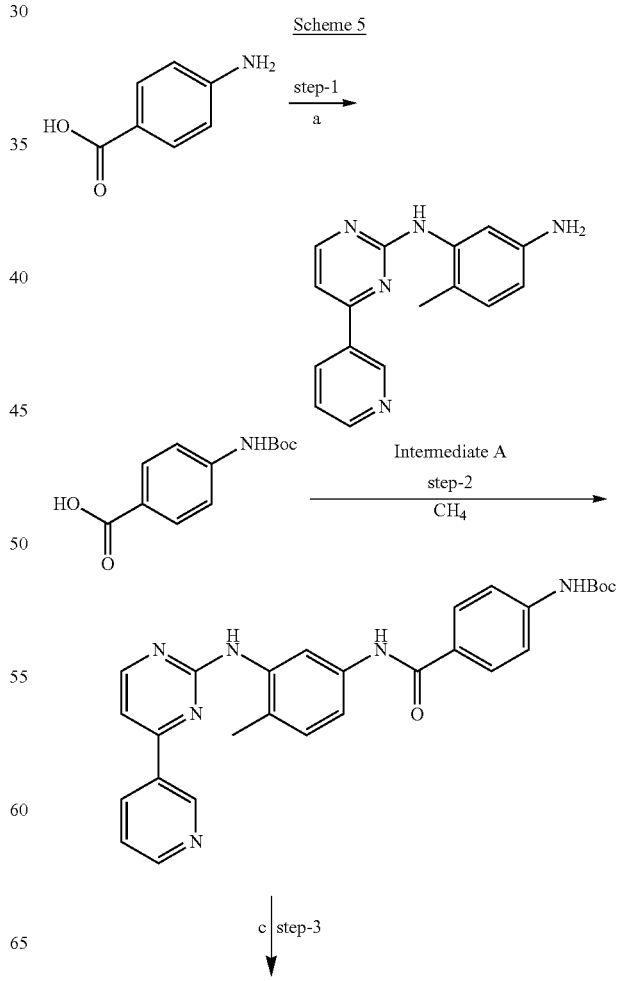

Scheme 5

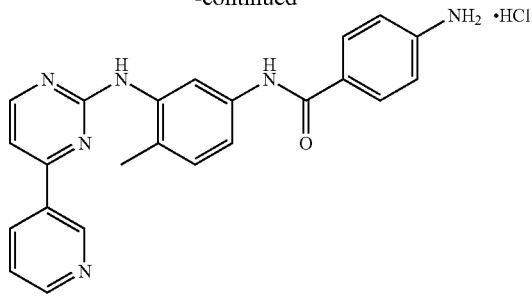

Intermediate B a) (BOC)₂O, dioxan/10% NaHCO₃ soln.;
b) EDCI/HOBT, DIPEA, CH₂Cl₂;
c) dioxan/HCl, rt, 16 h.

Step-1

To a solution of 4-aminobenzoic acid (5.0 g, 36.44 mmol) in 1,4-dioxan/10% aq. NaHCO₃ soln (1:1, 20 mL) was added a cat. amount of TBAB (0.58 g, 1.82 mmol) and the reaction mixture was stirred at 0° C. To it was added BOC anhydride (11.91 g, 54.6 mmol) and the reaction was allowed to stir at rt for 22 h. The reaction mixture was then acidified with 10% aq. citric acid soln. when 4N-Boc-aminobenzoic acid precipitated out as a white solid. It was filtered, washed with water (100 mL), dried to get 4N-Boc-aminobenzoic acid (6.8 g, 79%) as a white solid, which was used for next step.

Step-2

To a solution of 4N-Boc-aminobenzoic acid (0.85 g, 3.6 mmol) in CH₂Cl₂ (20 mL) was added EDCI (0.76 g, 3.97 mmol) and HOBT (0.54 g, 3.97 mmol). The reaction was stirred for 15 min and to it was added DIPEA (0.51 g, 3.97 mmol) and Intermediate A (1.0 g, 3.6 mmol). The reaction was further stirred at rt for 24 h and then diluted with EtOAc (100 mL), washed with water (2×25 mL), brine (10 mL) and dried over Na₂SO₄. Concentration under reduced pressure provided the corresponding amide as a crude solid which was crystallized (CH₂Cl₂/MeOH) to get the amide (0.4 g, 22%) as a white solid.

Step-3

A solution of the amide (0.4 g, 0.8 mmol) in dioxan (10 mL) was cooled to 0° C. and purged with dry HCl for 10 min (reaction mixture turns acidic) and allowed to stir for 16 h. After that the solvents were removed under reduced pressure to get Intermediate B, which was washed with ether (10 mL) to get Intermediate B (0.28 g, 87%) as an orange solid.

Example 10

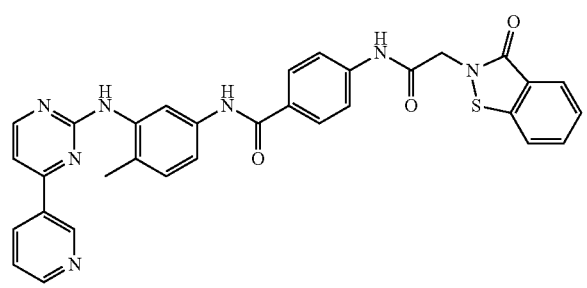

II-30

Step 1

2-(Chlorocarbonyl)phenyl hypochlorothioite can be prepared from 2,2'-dithiodibenzoic acid by treatment with thionyl chloride as described in Synthetic Communications, 13(12), 977-83; 1983

Step 2

Treatment of glycine with 2-(chlorocarbonyl)phenyl hypochlorothioite in the presence of pyridine can provide 2-(3-oxobenzo[d]isothiazol-2(3H)-yl)acetic acid as described in Farmaco, 44(9), 795-807; 1989.

Step 3

Coupling of 2-(3-oxobenzo[d]isothiazol-2(3H)-yl)acetic acid and Intermediate A in the presence of DCC and N-hydroxysuccinimde in DMF/CH₂Cl₂ can provide compound II-30 (protocol similar to that described in Synthesis, (17), 2647-2654; 2003).

Example 11

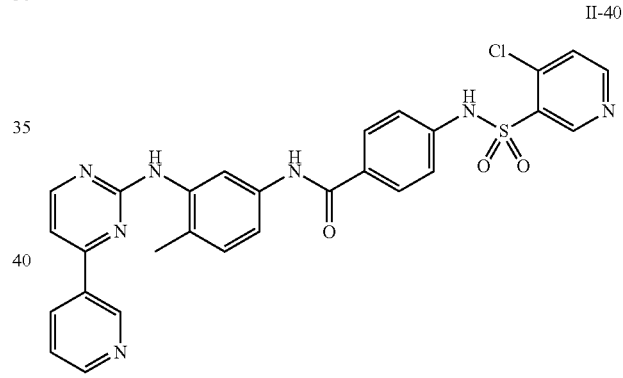

II-40

Scheme 6

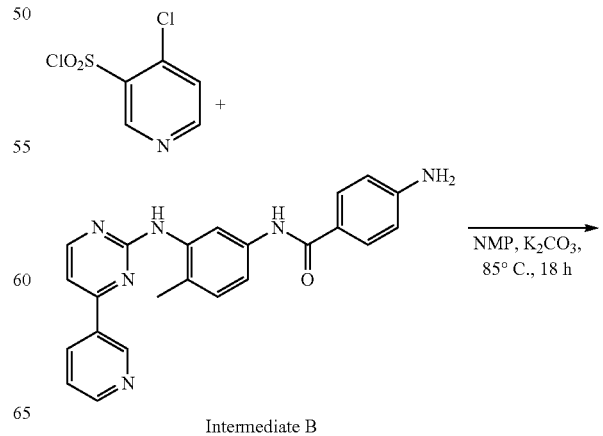

Intermediate B

-continued

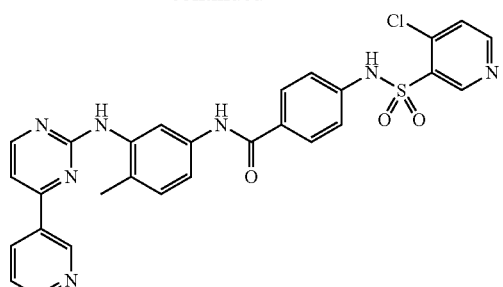

II-40

To a stirred mixture of Intermediate B (0.4 g, 1.01 mmol) and pyridinyl sulfonyl chloride (0.23 g, 1.11 mmol) in NMP (5 mL) was added dry K₂CO₃ (0.35 g, 2.52 mmol) and the reaction was heated at 85° C. for 18 h. The reaction mixture was then cooled, diluted with CH₂Cl₂ (5 mL) and allowed to pass through a small bed of Celite®. The filtrate was concentrated, purified by chromatography (alumina, mixtures of CHCl₃ & MeOH) to get crude II-40 which was further purified by preparative HPLC to get II-40 (0.015 g, 2.6%) as a pale yellow solid. LC/MS (M−H⁺): 569.8, 1H NMR (DMSO-d₆, 400 MHZ) δ (ppm): 2.19 (s, 3H), 7.16 (d, J=8.28 Hz, 1H), 7.22 (d, J=8.68 Hz, 2H), 7.38-7.41 (m, 2H), 7.49-7.52 (m, 1H), 7.77-7.82 (m, 3H), 8.0 (s, 1H), 8.44-8.49 (m, 2H), 8.67 (dd, J=1.36 & 4.68 Hz, 1H), 8.74 (d, J=5.28 Hz, 1H), 8.96 (s, 1H), 9.14 (s, 1H), 9.25 (d, J=1.36 Hz, 1H), 10.06 (s, 1H), 11.32 (s, 1H)

Example 12

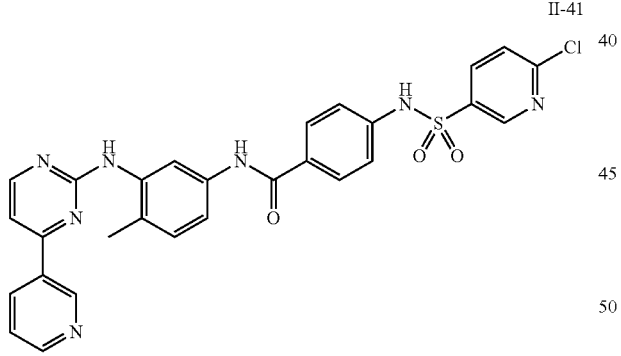

II-41

-continued

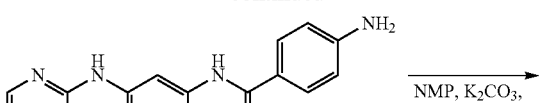

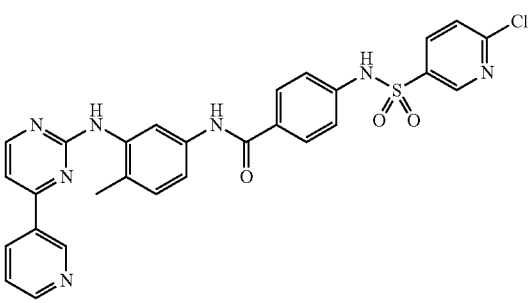

To a stirred solution of Intermediate B (0.40 g, 1.01 mmol) and pyridinylsulfonyl chloride (0.32 g, 1.5 mmol) in NMP was added dry K₂CO₃ (0.56 g, 4.04 mmol) and the reaction was heated at 85° C. for 18 h. The reaction was then cooled, diluted with CH₂Cl₂ (5 mL) and passed through a pad of Celite®. The filtrate was concentrated and purified by chromatography (neutral alumina, mixtures of CHCl₃ & MeOH) to get II-41 which was further purified by preparative HPLC to afford II-41 (0.028 g, 4.8%) as an off white solid. LC/MS (M+H⁺): 572.1, 1H NMR (MeOD, 400 MHZ) δ (ppm): 2.31 (s, 3H), 7.24-7.28 (m, 3H), 7.35-7.38 (m, 2H), 7.53-7.56 (m, 1H), 7.59 (d, J=8.44 Hz, 1H), 7.86 (d, J=8.72 Hz, 2H), 8.14-8.18 (m, 2H), 8.46 (d, J=5.24 Hz, 1H), 8.57-8.61 (m, 2H), 8.63 (d, J=1.56 Hz, 1H), 9.30 (s, 1H)

Example 13

II-44

[structure of II-44]

Scheme 7

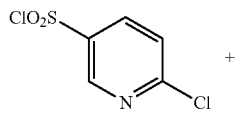

+

Scheme 8

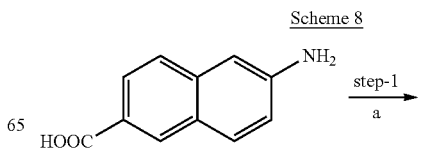

step-1
a

-continued

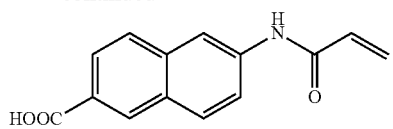

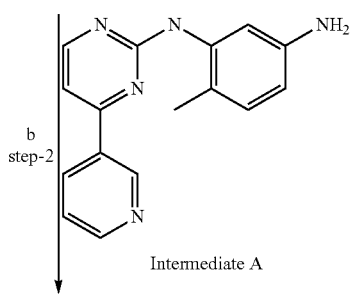

Intermediate A

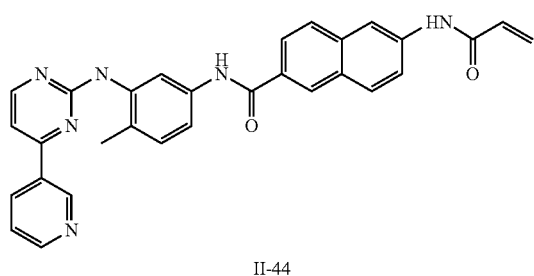

II-44 a) Acryloyl chloride, pyridine, DMF;
b) HATU, DIEA, DMF, rt, 16 h

Step-1: 6-Acryloylaminonaphthalene-2-carboxylic acid

To a stirred solution of 2-Amino-6-naphthoic acid (0.3 g, 1.6 mmol) in DMF (2 mL) and pyridine (0.3 mL) was added at 0° C., acryloyl chloride (0.15 g, 1.6 mmol). The resulting mixture was allowed to come to rt and stirred further for 2 h. After that it was poured in water (5 mL) and the solid separated was filtered and dried under reduced pressure to get the desired product (160 mg, 41.5%) as a pale brown solid. This solid was used in the next step without further purification.

Step-2: 6-Acryloylaminonaphthalene-2-carboxylic acid[4-methyl-3-(4-pyridin-3-yl pyrimidin-2-ylamino)phenyl]amide (II-44)

To a stirred solution of 6-acryloylaminonaphthalene-2-carboxylic acid (74 mg, 0.31 mmol) and Intermediate A (85 mg, 0.31 mmol) in DMF (2 mL) was added DIEA (0.08 mL). To it was added HATU (0.176 g, 0.47 mmol) and the reaction mixture was allowed to stir at rt for 16 h. The reaction mixture was then diluted with water (5 mL) and EtOAc (10 mL) and passed through a small pad of Celite® to remove inorganics. The organic and aqueous phases were separated and the aqueous phase was again extracted with EtOAc (2×10 mL). The combined organics were washed with brine (10 mL), dried ($Na_2SO_4$) and then purified by flash chromatography (silica, 230-400, mixtures of $CHCl_3$/MeOH) to get II-44 (33 mg, 21%) as a pale yellow solid. MS (M+H): 500.5, 1H NMR (DMSO-$d_6$, 400 MHZ) δ (ppm): 2.23 (s, 3H), 5.82 (d, J=10 Hz, 1H), 6.32 (d, J=16 Hz, 1H), 6.51 (dd, J=10 & 16 Hz, 1H), 7.22 (d, J=8.2 Hz, 1H), 7.43 (dd, J=0.8 & 5.2 Hz, 1H), 7.50-7.54 (m, 2H), 7.73 (d, J=9.2 Hz, 1H), 7.93-8.0 (m, 2H), 8.04 (d, J=8.8 Hz, 1H), 8.12 (s, 1H), 8.48-8.68 (m, 4H), 8.67 (d, J=4.7 Hz, 1H), 9.0 (s, 1H), 9.28 (d, J=1 Hz, 1H), 10.34 (s, 1H), 10.49 (s, 1H)

Example 14

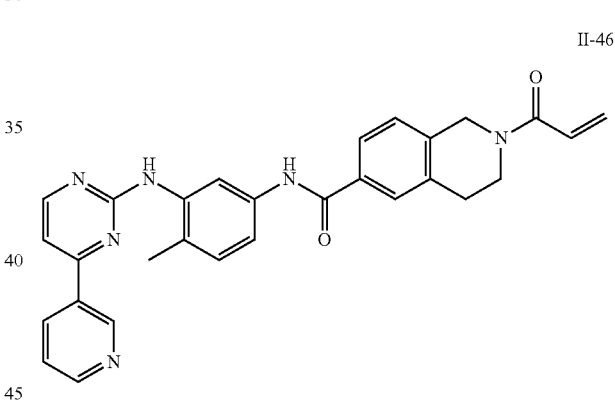

II-46

Step 1 tert-Butyl 6-((4-methyl-3-(4-(pyridin-3-yl)pyrimidin-2-ylamino)phenyl)carbamoyl)-3,4-dihydroisoquinoline-2(1H)-carboxylate can be synthesized by treating commercially available 2-[[(1,1-dimethylethyl)oxy]carbonyl]-1,2,3,4-tetrahydro-6-isoquinolinecarboxylic acid and Intermediate A using the same reaction conditions as in Example 1.

Step 2

Deprotection of tert-butyl 6-((4-methyl-3-(4-(pyridin-3-yl)pyrimidin-2-ylamino)phenyl)carbamoyl)-3,4-dihydroisoquinoline-2(1H)-carboxylate with HCl/dioxane followed by treatment with acryloyl chloride in a mixture of DMF and pyridine using the protocol in step 2 of Example 1 can provide compound II-46.

Scheme 9

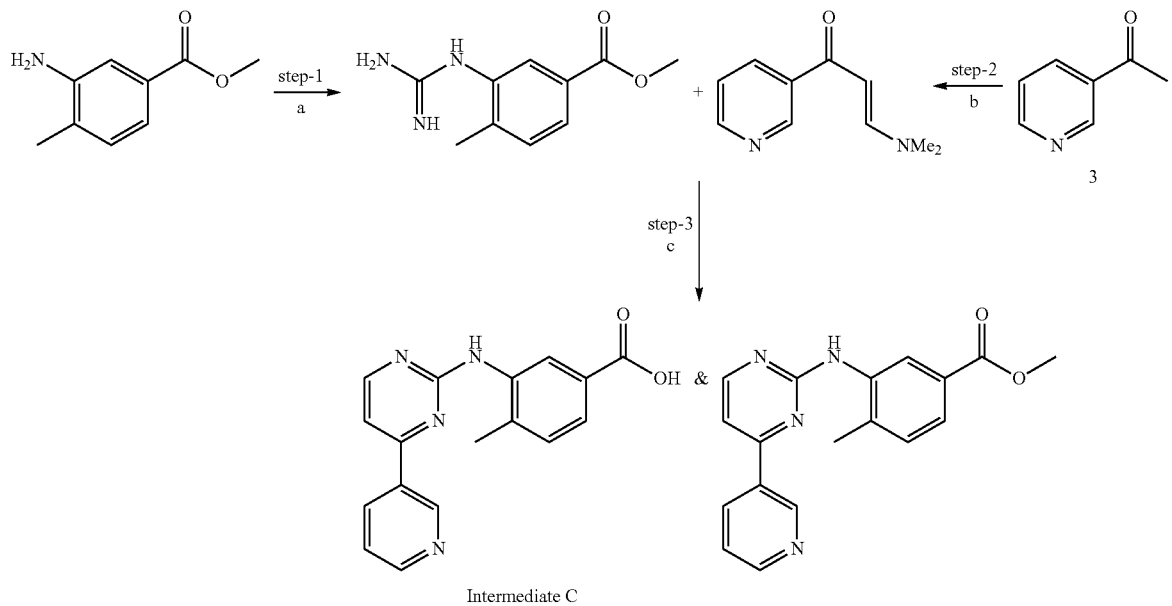

Intermediate C a) NH₂CN, EtOH/HCl, 90° C., 15 h,
b) DMF-DMA, ethanol, reflux, 16 h,
c) NaOH/EtOH, reflux, 16 h

Step-1

To a stirred solution of the aniline ester (5 g, 30.27 mmol) in ethanol (12.5 mL) was added conc. HNO₃ (3 mL), followed by 50% aq. solution of cyanamide (1.9 g, 46.0 mmol) at rt. The reaction mixture was heated at 90° C. for 16 h and then cooled to 0° C. A solid precipitated out which was filtered, washed with ethyl acetate (10 mL), diethyl ether (10 mL), and dried to give the corresponding guanidine (4.8 g, 76.5%) as a light pink solid which was used without further purifications.

Step-2

A stirred solution of 3-acetyl pyridine (10.0 g, 82.56 mmol) and N,N-dimethylformamide dimethyl acetal (12.8 g, 96.00 mmol) in ethanol (40 mL) was refluxed for 16 h. It was then cooled to rt and concentrated under reduced pressure to get a crude mass. The residue was taken in ether (10 mL), cooled to 0° C. and filtered to get the corresponding enamide (7.4 g, 50.8%) as a yellow crystalline solid.

Step-3

A stirred mixture of the guanidine derivative (2 g, 9.6 mmol), the enamide derivative (1.88 g, 10.7 mmol) and NaOH (0.44 g, 11.0 mmol) in ethanol (27 mL) was refluxed at 90° C. for 48 h. The reaction mixture was then cooled and concentrated under reduced pressure to get a residue. The residue was taken in ethyl acetate (20 mL) and washed with water (5 mL). The organic and aqueous layers were separated and treated separately to get the corresponding ester and Intermediate C respectively. The aq. layer was cooled and acidified with 1.5 N HCl (pH~3-4) when a white solid precipitated out. The precipitate was filtered, dried and excess water was removed by azeotropic distillation over toluene (2×10 mL) to get Intermediate C (0.5 g) as a pale yellow solid.

1H NMR (DMSO-d₆, 400 MHz) δ (ppm): 2.32 (s, 3H), 7.36 (d, J=10.44 Hz, 1H), 7.53 (d, J=6.84 Hz, 1H), 760-7.72 (m, 2H), 8.26 (s, 1H), 8.57 (d, J=6.84 Hz, 1H), 8.64 (d, J=10.28 Hz, 1H), 8.70-8.78 (bs, 1H), 9.15 (s, 1H), 9.35 (s, 1H). The organic extract was washed with brine (3 mL), dried (Na₂SO₄) and concentrated under reduced pressure to get the ester of Intermediate C as crude solid. It was further purified by column chromatography (SiO₂, 60-120 mesh, MeOH/CHCl₃: 10/90) to get the ester of Intermediate C (0.54 g) as a yellow solid.

Scheme 10

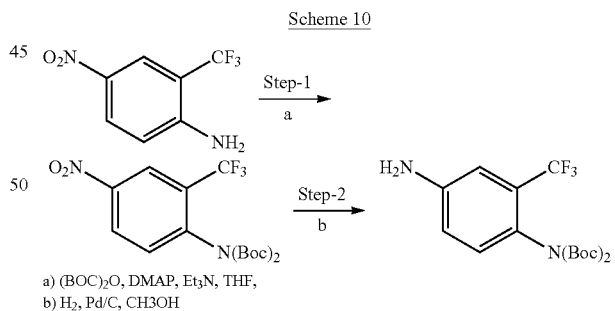

a) (BOC)₂O, DMAP, Et₃N, THF,
b) H₂, Pd/C, CH3OH

Step-1

To a stirring solution of the nitroaniline (0.15 g, 0.7 mmol) in THF (0.3 mL) was added Et₃N (0.11 mL, 0.73 mmol) and DMAP (0.05 g, 0.44 mmol). To it was added BOC anhydride (0.33 mL, 1.52 mmol) and the reaction was allowed to reflux for 5 h. The reaction mixture was then cooled, diluted with THF (15 mL) and washed with brine (5 mL). The organic phase was separated, dried over Na₂SO₄, filtered and concentrated under reduced pressure to get a crude mass. The crude product was further purified by column chromatography (SiO$_2$, 230-400 mesh, Hexane/EtOAc:8/2) to get corresponding di-Boc protected aniline (0.25 g, 88%) as a white crystalline solid which was taken for next step without further purification.

Step-2

A solution of Boc protected aniline (0.25 g, 0.62 mmol) in MeOH (5 mL) was hydrogenated (H$_2$, 3 Kg) over 10% Pd/C (0.14 g, 0.13 mmol) at 20° C. for 12 h. The reaction mixture was passed through a short pad of Celite®, concentrated under reduced pressure to get the corresponding aniline as an off-white solid (0.18 g, 77.6%). 1H NMR (CD$_3$OD, 400 MHz) δ (ppm): 1.36 (s, 18H), 6.84-6.87 (m, 1H), 6.95-6.97 (m, 2H).

Example 15

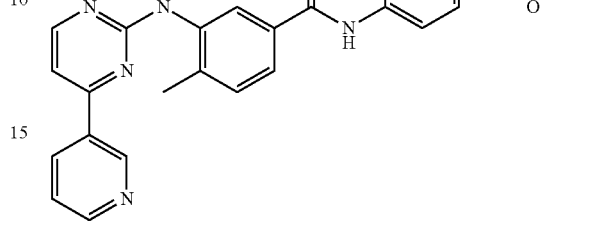

III-1

Scheme 11

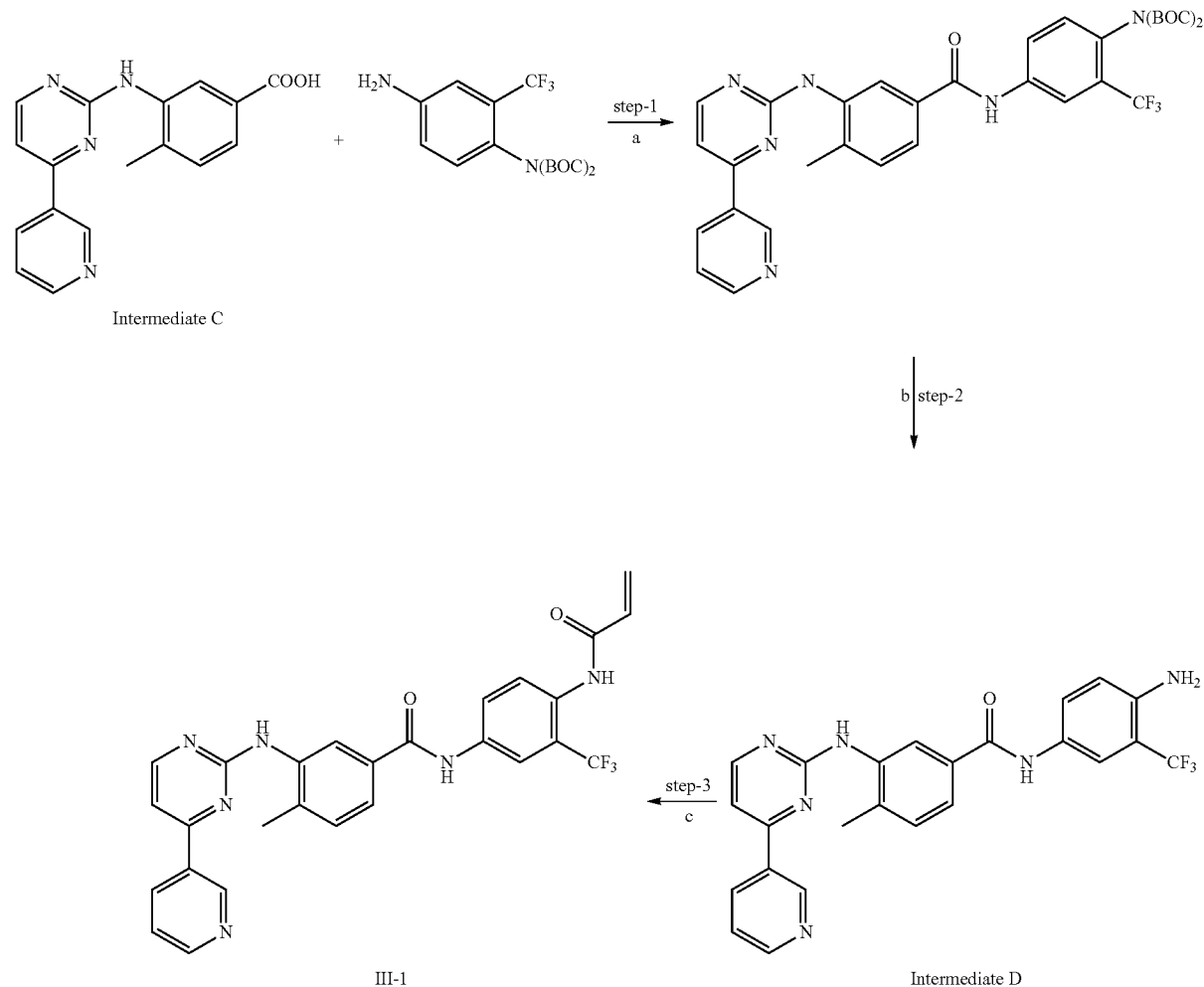

a) HATU, DIEA, CH$_3$CN, 85° C., 16 h,
b) TFA/CH$_2$Cl$_2$, 0° C. to rt, 3 h,
c) acryloyl chloride, pyridine, DMF, rt a) HATU, DIEA, CH₃CN, 85° C., 16 h, b) TFA/CH₂Cl₂, 0° C. to rt, 3 h, c) acryloyl chloride, pyridine, DMF, rt Step-1

Coupling of Intermediate C with diboc protected aniline in the presence of HATU, DIEA in acetonitrile can provide the corresponding amide Step-2

Deprotection of the Boc groups to give Intermediate D can be accomplished by treating the amide with TFA in methylene chloride at 0° C. and then warming up to room temperature.

Step 3

Acylation of Intermediate D with acryloyl chloride in a mixture of pyridine and DMF can provide III-1 similar to a procedure used in Example 1.

Example 16

III-5

Compound III-5 can be prepared by treating Intermediate D with ethene sulfonyl chloride in a mixture of pyridine and DMF using a protocol similar to that in Example 7.

Example 17

III-7

Compound III-7 can be prepared by treating Intermediate D with acid chloride prepared in Step 3, Example 9 in a mixture of triethyl amine and methylene chloride using a protocol similar to that in Example 9.

Example 18

III-8

Compound III-8 can be synthesized by treating compound III-1 (prepared according to Example 15) with dimethyldioxirane in acetone using a protocol similar to that described in Bioorganic & Medicinal Chemistry 10 (2002) 355-360.

Example 19

III-10

Compound III-10 can be synthesized by treating Intermediate D with chloropyridinyl sulfonyl chloride using a protocol similar to that described in Example 11.

Example 20

III-11

Compound III-11 can be synthesized by treating Intermediate D with chloropyridinyl sulfonyl chloride using a protocol similar to that described in Example 12.

Example 21

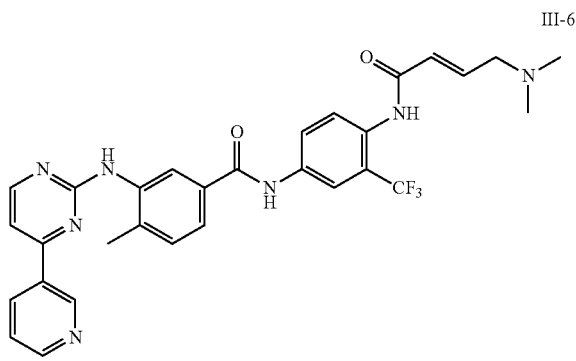

III-6

To a stirred solution of trans-4-dimethylamino-2-butenoic acid (0.13 g, 0.80 mmol) in acetonitrile (1.0 mL) was added oxalyl chloride (0.153 g, 1.2 mmol) at 0° C. The reaction mixture was allowed to stir at 0° C. for 30 minutes and then at room temperature for 2 h. Finally it was heated at 45° C. for 5 min, and cooled to room temperature. This mixture was added to a solution of Intermediate D (0.075 g, 0.16 mmol) in N-methylpyrrolidone (1.0 mL) at 0° C. The reaction mixture was stirred at 0° C. to 10° C. for 2 h, was quenched with cold water (1 mL), and was extracted with $CHCl_3$ (3×5 mL). The combined organic extract was washed sequentially with water (1 mL) and brine (1 mL), and then was dried over $Na_2SO_4$. Concentration under reduced pressure followed by purification by column chromatography ($SiO_2$, 230-400 mesh, $CHCl_3$/MeOH, 95/5) gave III-6 (0.02 g, 22%) as a light yellow solid. $^1H$ NMR (DMSO-d6) δ ppm: 2.18 (s, 6H), 2.34 (s, 3H), 3.06 (d, J=5.6 Hz, 2H), 6.25-6.45 (m, 1H), 6.65-6.85 (m, 1H), 7.43 (d, J=8.12 Hz, 1H), 7.47-7.52 (m, 3H), 7.74 (dd, J=1.76 & 8.0 Hz, 1H), 8.06 (dd, J=2 & 8.76 Hz, 1H), 8.22 (d, J=2.68 Hz, 1H), 8.29 (s, 1H), 8.43-8.45 (m, 1H), 8.54 (d, J=5.16 Hz, 1H), 8.68 (dd, J=1.64 & 4.8 Hz, 1H), 9.16 (s, 1H), 9.27 (d, J=1.8 Hz, 1H), 9.62 (s, 1H), 10.48 (s, 1H); LCMS m/e: 576.3 (M+1).

Example 22

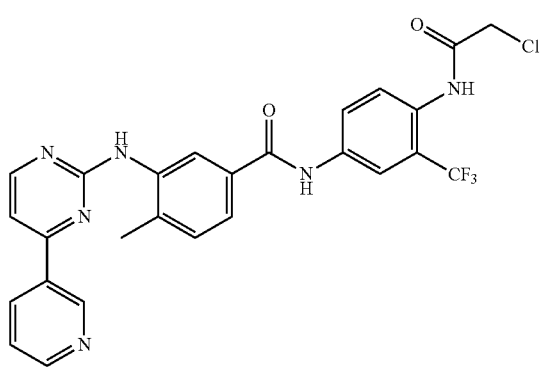

III-14

To a stirred solution of Intermediate D (0.1 g, 0.22 mmol) in THF (10 mL) at 0° C. was added $Et_3N$ (0.033 g, 0.32 mmol) under $N_2$. Chloroacetyl chloride (0.029 g, 0.26 mmol) was added dropwise with stirring and the reaction mixture was allowed to come to room temperature and was stirred for 12 h. The reaction mixture was concentrated under reduced pressure to give a residue, which was taken in EtOAc (10 mL). This solution was washed with water (2 mL) and the aqueous layer was again extracted with EtOAc (2×10 mL). The EtOAc fractions were combined and were washed with brine (2 mL). Following drying over $Na_2SO_4$ and filtration the EtOAc solution and was concentrated under reduced pressure to give crude residue, which was then purified by column chromatography ($SiO_2$, 60-120 mesh, $CHCl_3$/MeOH:9/1) to give III-14 (50 mg, 43%) as a pale yellow solid. 1H NMR (DMSO-$d_6$) δ ppm: 2.34 (s, 3H), 4.30 (s, 2H), 7.42-7.48 (m, 4H), 7.73-7.75 (m, 1H), 8.05-8.10 (m, 1H), 8.24 (d, J=2.2 Hz, 1H), 8.29 (s, 1H), 8.43 (d, J=8.04 Hz, 1H), 8.54 (d, J=5.16 Hz, 1H), 8.67 (dd, J=1.6 & 4.76 Hz, 1H), 9.16 (s, 1H), 9.26 (d, J=2.2 Hz, 1H), 9.89 (s, 1H), 10.50 (s, 1H); LCMS: m/e 541.2 (M+1)

Example 23

PDGFR Inhibition Assay

Method A:

Compounds may also be assayed as inhibitors of PDGFR in a manner substantially similar to the method described in Roberts, et al., "Antiangiogenic and Antitumor Activity of a Selective PDGFR Tyrosine Kinase Inhibitor, CP-673,451" Cancer Research 65, 957-966, Feb. 1, 2005. In this assay, a glutathione S-transferase-tagged kinase domain construct of the intracellular portion of the PDGFR-β (amino acids 693-1,401, accession no. J03278) is expressed in Sf-9 cells (baculovirus expression system, Invitrogen, Carlsbad, Calif.). Enzyme kinetics are determined by incubating the enzyme with increasing concentrations of ATP in phosphorylation buffer [50 mmol/L HEPES (pH 7.3), 125 mmol/L NaCl, 24 mmol/L $MgCl_2$ in Nunc Immuno MaxiSorp 96-well plates previously coated with 100 μL of 100 μg/mL poly-Glu-Tyr (4:1 ratio) diluted in PBS. After 10 minutes, the plates are washed (PBS, 0.1% Tween 20), incubated with anti-phosphotyrosine-horseradish peroxidase antibody, and diluted in PBS, 0.05% Tween 20, 3% BSA for 30 minutes at room temperature. The plates are washed as above and incubated with 3,3',5,5'-tetramethylbenzidine. The reaction is stopped by adding an equal volume of 0.09 N $H_2SO_4$. The phosphotyrosine-dependent signal is then quantitated on a plate reader at 450 nm. For routine enzyme assays, the enzyme is incubated with 10 μmol/L (final) ATP in the presence of compound diluted in DMSO (1.6% v/v DMSO assay final) for 30 minutes at room temperature in plates, as above, previously coated with 100 μL of 6.25 μg/mL poly-Glu-Tyr. The remainder of the assay is carried out as above, and $IC_{50}$ values are calculated as percent inhibition of control. Selectivity assays are done as described above using purified recombinant enzyme (generated as described above) and ATP concentrations at or up to 3× above the $K_m$ for each enzyme.

Method B:

Compounds were assayed as inhibitors of PDGFR in a manner substantially similar to the method described by Invitrogen Corp (Invitrogen Corporation, 1600 Faraday Avenue, Carlsbad, Calif., CA; http://www.invitrogen.com/downloads/Z-LYTE_Brochure_1205.pdf) using the Z'-LYTE™ biochemical assay procedure or similar biochemical assay. The Z'-LYTE™ biochemical assay employs a fluorescence-based, coupled-enzyme format and is based on the differential sensitivity of phosphorylated and non-phosphorylated peptides to proteolytic cleavage.

Compound I-1 was tested at 0.1 µM and 1 µM in duplicate. Compound I-1 showed a mean inhibition of PDGFR-α of 76% at 1 µM and 29% at 0.1 µM.

Method C

Compounds may also be assayed as inhibitors of PDGFR alpha (h) in a manner substantially similar to the method described by Upstate (http://www.upstate.com/img/pdf/KP_Protocol_121506.pdf). The protein is recombinant human PDGFRα, residues 550-end, containing an N-terminal His6-tag. Expressed by baculovirus in Sf21 insect cells. Purified using Ni2+/NTA agarose. In a final reaction volume of 25 µL, PDGFR alpha (wild-type) (5-10 mU) is incubated with 8 mM MOPS pH 7.0, 0.2 mM EDTA, 10 mM MnCl$_2$, 0.1 mg/mL poly(Glu, Tyr) 4:1, 10 mM MgAcetate and [©-33P-ATP] (specific activity approx. 500 cpm/pmol, concentration as required). The reaction is initiated by the addition of the MgATP mix. After incubation for 40 minutes at room temperature, the reaction is stopped by the addition of 5 µL of a 3% phosphoric acid solution. 10 µL of the reaction is then spotted onto a Filtermat A and washed three times for 5 minutes in 75 mM phosphoric acid and once in methanol prior to drying and scintillation counting. The compound is dissolved to 50× final assay concentration in 100% DMSO, and assayed using 0.5 µL of this compound solution in a final reaction volume of 25 ul as above. DMSO only (0.5 ul) is tested in parallel as a control Method D Briefly, 10× stock of PDGFRα (PV3811) enzyme, 1.13× ATP (AS001A) and Y12-Sox peptide substrates (KCZ1001) was prepared in 1× kinase reaction buffer consisting of 20 mM Tris, pH 7.5, 5 mM MgCl$_2$, 1 mM EGTA, 5 mM β-glycerophosphate, 5% glycerol (10× stock, KB002A) and 0.2 mM DTT (DS001A). 5 µL of enzyme were pre-incubated in a Corning (#3574) 384-well, white, non-binding surface microtiter plate (Corning, N.Y.) for 30 min at 27° C. with a 0.5 µL volume of 50% DMSO and serially diluted compounds prepared in 50% DMSO. Kinase reactions were started with the addition of 45 µL of the ATP/Y9 or Y12-Sox peptide substrate mix and monitored every 30-9 seconds for 60 minutes at $\lambda_{ex}360/\lambda_{em}485$ in a Synergy$^4$ plate reader from BioTek (Winooski, Vt.). At the conclusion of each assay, progress curves from each well were examined for linear reaction kinetics and fit statistics ($R^2$, 95% confidence interval, absolute sum of squares). Initial velocity (0 minutes to 20+ minutes) from each reaction was determined from the slope of a plot of relative fluorescence units vs time (minutes) and then plotted against inhibitor concentration to estimate IC$_{50}$ from log [Inhibitor] vs Response, Variable Slope model in GraphPad Prism from GraphPad Software (San Diego, Calif.). [PDGFRα]=2-5 nM, [ATP]=60 µM and [Y9-Sox peptide] =10 µM (ATP K$_{Mapp}$=61 µM)

PDGFR inhibition data for certain compounds of the present invention are set forth in Table 5, below.

TABLE 5

PDGFR Inhibition Data

| Compound # | % Inhibition | Conc. (µM) | IC$_{50}$ (nM) |
|---|---|---|---|
| II-1 | 76 | 1 | 172.94 |
| II-2 | 91 | 1 | 2.2 |
| II-4 | 28 | 1 | — |
| II-6 | — | — | 29.8 |
| II-8 | — | — | 10.69 |
| II-23 | — | — | 18.8 |
| II-45 | — | — | 7.9 |
| II-52 | — | — | 1017 |
| II-53 | — | — | 16.4 |
| II-54 | — | — | 184.8 |
| II-55 | — | — | 1.4 |
| III-6 | — | — | 5.90 |
| III-14 | — | — | 0.73 |

Example 24

PDGFR Mass Spectral Analysis of Compound I-1

Mass spectral analysis of PDGFR-α in the presence of test compound I-1 was performed. PDGFR-α protein (supplied from Invitrogen: PV3811) was incubated with 1 µM, 10 µM, and 100 µM test compound for 60 minutes. Specifically, 1 µL of 0.4 µg/µL PDGFR-α (Invitrogen PV3811) stock solution (50 mM Tris HCl ph 7.5, 150 mM NaCl, 0.5 mM EDTA, 0.02% Triton X-100, 2 mM DTT, 50% glycerol) was added to 9 µL of test compound in 10% DMSO (final concentration of 1 µM, 10 µM, and 100 µM). After 60 minutes, 9 µL of 50 mM ammonium bicarbonate, 3.3 µL of 6 mM iodoacetamide in 50 mM ammonium bicarbonate, and 1 µL of 35 ng/µL trypsin was added to stop the reaction.

The tryptic digest was analyzed by mass spectrometer (MALDI-TOF) at 10 µM. Of the five cysteine residues found in the PDGFR-α protein, four of the cysteine residues were identified as being modified by iodoacetamide, while the fifth cysteine residue was modified by the test compound. Mass spectral analysis of the tryptic digests was consistent with test compound being covalently bound to PDGFR-α protein at Cys814. MS/MS analysis of the tryptic digests confirmed presence of the test compound at Cys814.

Example 25

PDGFR Mass Spectral Analysis of Compound III-14

Mass spectral analysis of PDGFR-α in the presence of test III-14 was performed. PDGFR-α (43 pmols) was incubated with compound III-14 (434 pmols) for 3 hours at 10× access prior to tryptic digestion. Iodoacetamide was used as the alkylating agent after compound incubation. For tryptic digests a 5 µl aliquot (7 pmols) was diluted with 10 µl of 0.1% TFA prior to micro C18 Zip Tipping directly onto the MALDI target using alpha cyano-4-hydroxy cinnamic acid as the matrix (5 mg/ml in 0.1% TFA:Acetonitrile 50:50).

The tryptic digest was analyzed by mass spectrometer (MALDI-TOF). Mass spectral analysis of the tryptic digests was consistent with test compound being covalently bound to PDGFR-α protein at Cys814. MS/MS analysis of the tryptic digests confirmed presence of the test compound at Cys814.

Example 26

EOL-1 Cellular Proliferation Assay

EOL-1 cells purchased from DSMZ (ACC 386) were maintained in RPMI (Invitrogen #21870)+10% FBS+1% penicillin/streptomycin (Invitrogen #15140-122). For cell proliferation assays, cells in complete media were plated in 96 well plates at a density of $2 \times 10^4$ cells/well and incubated in duplicate with compound ranging from 500 nM to 10 pM for 72 hours. Cell proliferation was assayed by measuring metabolic activity with Alamar Blue reagent (Invitrogen cat #DAL1100). After 8 hours incubation with Alamar Blue at 37° C., absorbance was read at 590 nm and the $IC_{50}$ of cellular proliferation was calculated using GraphPad. Dose response inhibition of cell proliferation of EOL-1 cells with reference compound and compound II-2 is depicted in FIG. 1.

Example 27

EOL-1 Cell Washout Assay

Figure 2:
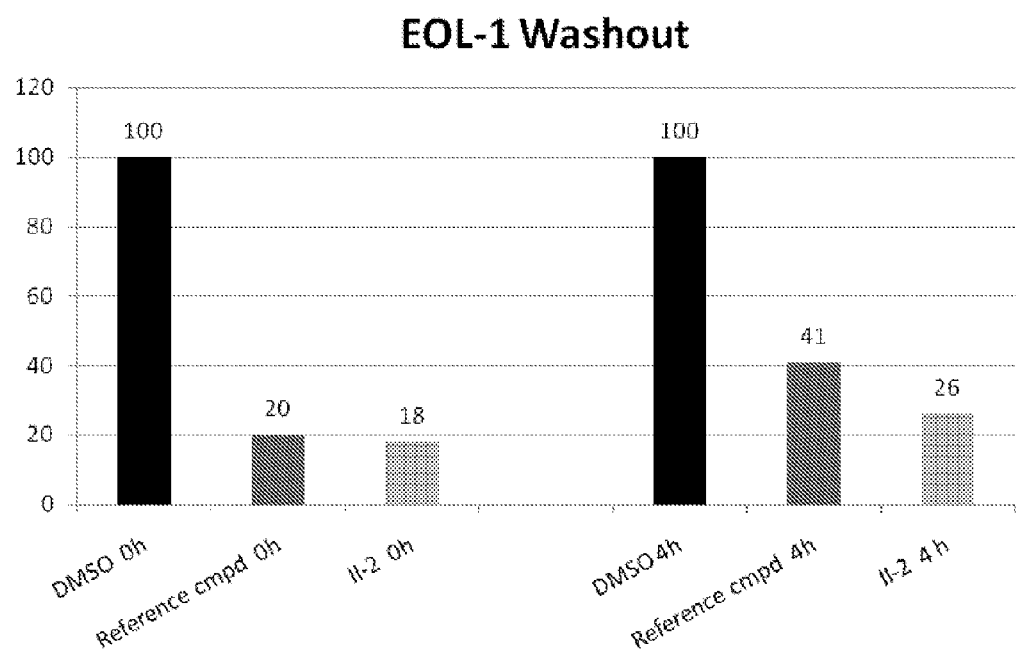
FIG. 2 depicts the inhibition of PDGFR with reference compound and compound II-2 in a "washout" experiment using EOL-1 cells.

EOL-1 cells were grown in suspension in complete media and compound was added to $2 \times 10^6$ cells per sample for 1 hour. After 1 hour, the cells were pelleted, the media was removed and replaced with compound-free media. Cells were washed every 2 hours and resuspended in fresh compound-free media. Cells were collected at specified timepoints, lysed in Cell Extraction Buffer and 15 µg total protein lysate was loaded in each lane. PDGFR phosphorylation was assay by western blot with Santa Cruz antibody sc-12910. The results of this experiment are depicted in FIG. 2 where it is shown that relative to DMSO control and to a reversible reference compound, compound II-2 maintained enzyme inhibition of PDGFR in EOL-1 cells after "washout" after 0 hours and 4 hours.

Example 28 cKit Inhibition Assay

Method A
Compounds may also be assayed as inhibitors of CKit in a manner substantially similar to the method described by Upstate (http://www.upstate.com/img/pdf/KP_Protocol_121506.pdf). In this assay, N-terminal GST tagged, recombinant, human Kit, amino acids 544-end, expressed by baculovirus, in Sf21 insect cells and purified using glutathione agarose is used. In a final reaction volume of 25 µL, c-kit (wild-type) (5-10 mU) is incubated with 8 mM MOPS pH 7.0, 0.2 mM EDTA, 10 mM $MnCl_2$, 0.1 mg/mL poly(Glu, Tyr) 4:1, 10 mM MgAcetate and [©-33P-ATP] (specific activity approx. 500 cpm/pmol, concentration as required). The reaction is initiated by the addition of the MgATP mix. After incubation for 40 minutes at room temperature, the reaction is stopped by the addition of 5 µL of a 3% phosphoric acid solution. 10 µL of the reaction is then spotted onto a Filtermat A and washed three times for 5 minutes in 75 mM phosphoric acid and once in methanol prior to drying and scintillation counting. The compound is dissolved to 50× final assay concentration in 100% DMSO, and assayed using 0.5 ul of this compound solution in a final reaction volume of 25 ul as above. DMSO only (0.5 ul) is tested in parallel as a control.
Method B
Compounds may also be assayed as inhibitors of cKit in a manner substantially similar to the method described by CellSignal (http://www.cellsignal.com/pdf/7755.pdf). The GST-c-Kit fusion protein is produced using a baculovirus expression system with a construct expressing a fragment of human c-Kit (Thr544-Val976) with an amino-terminal GST tag. The protein is purified by one-step affinity chromatography using glutathione-agarose. In this assay 10 µl 10 mM ATP is added to 1.25 ml 6 µM KDR (Tyr996) Biotinylated Peptide substrate peptide. The mixture is diluted with dH20 to 2.5 ml to make 2×ATP/substrate cocktail ([ATP]=40 µM, [substrate]=3 µm) The c-KIT enzyme is transferred immediately from −80° C. to ice. The enzyme is allowed to thaw on ice. The vial is microcentrifuged briefly at 4° C. to bring liquid to the bottom of the vial and it is then returned immediately to ice. 10 µl of DTT (1.25 M) is added to 2.5 ml of 4×HTScan™ Tyrosine Kinase Buffer (Cellsignal; 240 mM HEPES pH 7.5, 20 mM $MgCl_2$, 20 mM $MnCl_2$, 12 µM Na3VO4) to make DTT/Kinase buffer. 1.25 ml of DTT/Kinase buffer is transferred to enzyme tube to make 4× reaction cocktail ([enzyme]=4 ng/µL in 4× reaction cocktail). 12.5 µl of the 4× reaction cocktail is incubated with 12.5 µl/well of prediluted compound for 5 minutes at room temperature. 25 µl of 2×ATP/substrate cocktail is added to 25 µl/well preincubated reaction cocktail/compound. The reaction plate is incubated at room temperature for 30 minutes and 50 µl/well Stop Buffer (50 mM EDTA, pH 8) is added to stop the reaction. 25 µl of each reaction and 75 µl dH2O/well is transferred to a 96-well streptavidin coated plate and incubated at room temperature for 60 minutes. This is washed three times with 200 µl/well PBS/T. The primary antibody, Phospho-Tyrosine mAb (P-Tyr-100), is diluted 1:1000 in PBS/T with 1% BSA. 100 µl/well primary antibody is added and incubated at room temperature for 60 minutes. This is washed three times with 200 µl/well PBS/T. Europium labeled anti-mouse IgG 1:500 in PBS/T is diluted with 1% BSA. 100 µl/well diluted antibody is then added. This is then incubated at room temperature for 30 minutes and washed five times with 200 µl/well PBS/T. 100 µl/well DELFIA® Enhancement Solution is added and then incubated at room temperature for 5 minutes. A Time-Resolved Plate Reader is used to detect 615 nm fluorescence emission. Compounds showing greater than 50% inhibition versus standard wells containing the assay mixture and DMSO without test compound are titrated to determine $IC_{50}$ values.
Method C
Compounds of the invention were assayed as inhibitors of c-KIT using human recombinant c-KIT (obtained from Millipore, catalog number 14-559) and monitoring the phosphorylation of a fluorescein-labeled peptide substrate (1.5 µM). Reactions were carried out in 100 mM HEPES (pH 7.5), 10 mM $MnCl_2$, 1 mM DDT, 0.015% Brij-35, and 300 µM ATP, with and without test compound. The reaction was started by adding the ATP and incubating for 1 hour at room temperature. The reaction was terminated by the addition of stop buffer containing 100 mM HEPES (pH 7.5), 30 mM EDTA, 0.015% Brij-35, and 5% DMSO. Phosphorylated and unphosphorylated substrate was separated by charge using electrophoretic mobility shift. Product formed was compared to control wells to determine inhibition or enhancement of enzyme activity.

c-KIT inhibition data for certain compounds of the present invention are set forth in Table 6, below.

TABLE 6 c-KIT Inhibition Data

| Compound # | % Inhibition | Concentration (µM) |
|---|---|---|
| II-1 | 82 | 1 |
| II-2 | 88 | 1 |
| II-5 | 66 | 1 |
| II-6 | 91 | 1 |
| II-8 | 78 | 1 |

TABLE 6-continued c-KIT Inhibition Data

| Compound # | % Inhibition | Concentration (µM) |
|---|---|---|
| II-26 | 94 | 1 |
| II-44 | 95 | 1 |

Method D
c-Kit (V654A and T670I) Omnia Assays for Potency Assessment with Pre-Activated Enzyme:

Compounds were also tested as inhibitors of mutant c-KIT using the protocol below which describes a continuous-read kinase assay to measure inherent potency of compounds against pre-activated c-KIT (V654A) and c-KIT (T670I) enzymes.

Briefly, 10× stocks of c-KIT (V654A) from Millipore (14-733) or c-Kit (T670I) from Cell Signaling (7922) plus 1 mM ATP (AS001A) and 1.13×Y9-Sox or Y12-Sox peptide substrates (KCZ1001) were prepared in 1× kinase reaction buffer consisting of 20 mM Tris, pH 7.5, 5 mM $MgCl_2$, 1 mM EGTA, 5 mM β-glycerophosphate, 5% glycerol (10× stock, KB002A) and 0.2 mM DTT (DS001A). 10× enzyme/ATP stocks were pre-incubated for 30 min at room temperature to pre-activate each enzyme prior to compound exposure. 5 µL of each enzyme were then pre-incubated in a Corning (#3574) 384-well, white, non-binding surface microtiter plate (Corning, N.Y.) for 30 min at 27° C. with a 0.5 µL volume of 50% DMSO and serially diluted compounds prepared in 50% DMSO. Kinase reactions were started with the addition of 45 µL of the Y9 or Y12-Sox peptide substrate and monitored every 30-90 seconds for 60 minutes at $\lambda_{ex}360/\lambda_{em}485$ in a Synergy$^4$ plate reader from BioTek (Winooski, Vt.). At the conclusion of each assay, progress curves from each well were examined for linear reaction kinetics and fit statistics ($R^2$, 95% confidence interval, absolute sum of squares). Initial velocity (0 minutes to 20+ minutes) from each reaction was determined from the slope of a plot of relative fluorescence units vs time (minutes) and then plotted against inhibitor concentration to estimate $IC_{50}$ from log [Inhibitor] vs Response, Variable Slope model in GraphPad Prism from GraphPad Software (San Diego, Calif.).
[c-Kit V654A]=5 nM, [ATP]=100 µM and [Y9Sox]=10 µM (ATP $K_{Mapp}$=240 µM)
[c-Kit T670I]=5 nM, [ATP]=100 µM and [Y12-Sox]=10 µM (ATP $K_{Mapp}$=220 µM)
Method E
c-Kit (V654A and T670I) Omnia Assays for Potency Assessment:

Briefly, 10× stocks of c-Kit (V654A) from Millipore (14-733) or c-Kit (T670I) from Cell Signaling (7922), 1.13×ATP (AS001A) and Y9-Sox or Y12-Sox peptide substrates (KCZ1001) were prepared in 1× kinase reaction buffer consisting of 20 mM Tris, pH 7.5, 5 mM $MgCl_2$, 1 mM EGTA, 5 mM β-glycerophosphate, 5% glycerol (10× stock, KB002A) and 0.2 mM DTT (DS001A). 5 µL of each enzyme were pre-incubated in a Corning (#3574) 384-well, white, non-binding surface microtiter plate (Corning, N.Y.) for 30 min at 27° C. with a 0.5 µL volume of 50% DMSO and serially diluted compounds prepared in 50% DMSO. Kinase reactions were started with the addition of 45 µL of the Y9 or Y12-Sox peptide substrate and monitored every 30-90 seconds for 60 minutes at $\lambda_{ex}360/\lambda_{em}485$ in a Synergy$^4$ plate reader from BioTek (Winooski, Vt.). At the conclusion of each assay, progress curves from each well were examined for linear reaction kinetics and fit statistics ($R^2$, 95% confidence interval, absolute sum of squares). Initial velocity (0 minutes to 20+ minutes) from each reaction was determined from the slope of a plot of relative fluorescence units vs time (minutes) and then plotted against inhibitor concentration to estimate $IC_{50}$ from log [Inhibitor] vs Response, Variable Slope model in GraphPad Prism from GraphPad Software (San Diego, Calif.).
[c-Kit V654A]=5 nM, [ATP]=220 µM and [Y9-Sox]=10 µM (ATP $K_{Mapp}$=240 µM)
[c-Kit T670I]=5 nM, [ATP]=220 µM and [Y12-Sox]=10 µM (ATP $K_{Mapp}$=220 µM)

Mutant c-KIT (V654A) inhibition data for exemplary compounds are summarized in Table 7, below, where $IC_{50}$ values were obtained using the above-described assay protocol Method D and $IC_{50}$ Apparent values were obtained using the above-described assay protocol Method E.

TABLE 7

Mutant c-KIT (V654A) Inhibition Data

| Compound # | $IC_{50}$ (nM) | $IC_{50}$ Apparent (nM) |
|---|---|---|
| II-2 | — | 83 |
| II-40 | 10000 | — |
| II-41 | — | 173 |
| II-53 | 937 | 260 |
| II-54 | 10000 | — |
| II-55 | 9151 | — |
| III-6 | 3989 | 216 |
| III-14 | 2011 | 72 |

Mutant c-KIT (T670I) inhibition data for exemplary compounds are summarized in Table 8, below.

TABLE 8

Mutant c-KIT (T670I) Inhibition Data

| Compound # | $IC_{50}$ (nM) | $IC_{50}$ Apparent (nM) |
|---|---|---|
| III-6 | — | 1566 |
| III-14 | 72.4 | 205 |

Example 29 c-KIT Mass Spectral Analysis of Compound III-14

Mass spectral analysis of c-KIT in the presence of test compound III-14 was performed. Specifically, c-KIT kinase (86 pmols) was incubated with compound III-14 (863 pmols) for 3 hours at 10× access prior to tryptic digestion. Iodoacetamide was used as the alkylating agent after compound incubation. A newer sample was also prepared that used a higher grade of trypsin which eliminated the chymotryptic activity. For tryptic digests a 5 µl aliquot (14 pmols) was diluted with 10 ul of 0.1% TFA prior to micro C18 Zip Tipping directly onto the MALDI target using alpha cyano-4-hydroxy cinnamic acid as the matrix (5 mg/ml in 0.1% TFA:acetonitrile 50:50).

The tryptic digest was analyzed by mass spectrometer (MALDI-TOF). Mass spectral analysis of the tryptic digests was consistent with test compound being covalently bound to c-KIT protein at two target cystein residues: Cys808 (minor) and Cys788 (major).

Example 30 cKIT Washout Assay

Figure 3:
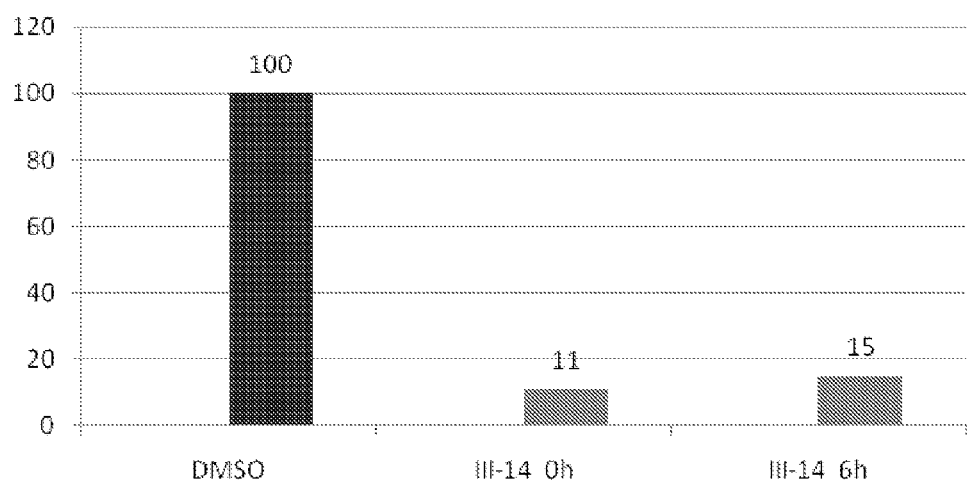
FIG. 3 depicts the inhibition of c-KIT with compound III-14 in a "washout" experiment using GIST430 cells.

GIST430 cells were seeded in a 6 well plate at a density of 8×10$^5$ cells/well and treated with 1 µM compound diluted in complete media for 90 minutes the next day. After 90 minutes, the media was removed and cells were washed with compound-free media. Cells were washed every 2 hours and resuspended in fresh compound-free media. Cells were collected at specified time-points, lysed in Cell Extraction Buffer (Invitrogen FNN0011) supplemented with Roche complete protease inhibitor tablets (Roche 11697498001) and phosphatase inhibitors (Roche 04 906 837 001) and 10 µg total protein lysate was loaded in each lane. c-KIT phosphorylation was assayed by western blot with pTyr (4G10) antibody and total kit antibody from Cell Signaling Technology. The results of this experiment are depicted in FIG. 3 where it is shown that compound III-14 maintains c-KIT enzyme inhibition in GIST430 cells after "washout" at 0 hours and 6 hours.

Example 31 cFMS Inhibition Assay

Compounds may also be assayed as inhibitors of cFMS (h) in a manner substantially similar to the method described by Upstate (http://www.upstate.com/img/pdf/KP_Protocol_121506.pdf). The protein is expressed as a N-terminal His-tagged, recombinant, human cFms, amino acids 538-end, in baculovirus in Sf21 insect cells and purified using Ni2+/NTA-agarose. In a final reaction volume of 25 µL, Fms (h) (5-10 mU) is incubated with 8 mM MOPS pH 7.0, 0.2 mM EDTA, 250 µM KKKSPGEYVNIEFG, 10 mM MgAcetate and [γ-33P-ATP] (specific activity approx. 500 cpm/pmol, concentration as required). The reaction is initiated by the addition of the MgATP mix. After incubation for 40 minutes at room temperature, the reaction is stopped by the addition of 5 µL of a 3% phosphoric acid solution. 10 µL of the reaction is then spotted onto a P30 filtermat and washed three times for 5 minutes in 75 mM phosphoric acid and once in methanol prior to drying and scintillation counting. The compound is dissolved to 50× final assay concentration in 100% DMSO, and assayed using 0.5 µl of this compound solution in a final reaction volume of 25 ul as above. DMSO only (0.5 µl) is tested in parallel as a control Example 32

KDR Inhibition Assay

Method A

Compounds may be screened for their ability to inhibit KDR using a standard coupled enzyme assay (Fox et al., Protein Sci., (1998) 7, 2249). Assays are carried out in a mixture of 200 mM HEPES 7.5, 10 mM $MgCl_2$, 25 mM NaCl, 1 mM DTT and 1.5% DMSO. Final substrate concentrations in the assay are 300 µM ATP (Sigma Chemicals) and 10 µM poly E4Y (Sigma). Assays are carried out at 37° C. and 30 nM KDR. Final concentrations of the components of the coupled enzyme system are 2.5 mM phosphoenolpyruvate, 200 µM NADH, 30 µg/ML pyruvate kinase and 10 µg/ml lactate dehydrogenase.

An assay stock buffer solution is prepared containing all of the reagents listed above, with the exception of ATP and the test compound of interest. 177 µl of the stock solution is placed in a 96 well plate followed by addition of 3 µl of 2 mM DMSO stock containing the test compound (final compound concentration 30 µM). The plate is preincubated for about 10 minutes at 37° C. and the reaction initiated by addition of 20 µA of ATP (final concentration 300 µM). Rates of reaction are obtained using a Molecular Devices plate reader (Sunnyvale, Calif.) over a 5 minute read time at 37° C. Compounds showing greater than 50% inhibition versus standard wells containing the assay mixture and DMSO without test compound are titrated to determine $IC_{50}$ values determined.

Method B

Compounds may also be assayed as inhibitors of KDR (h) in a manner substantially similar to the method described by Upstate (http://www.upstate.com/img/pdf/KP_Protocol_121506.pdf). The protein is expressed as a N-terminal 6His-tagged, recombinant, human KDR amino acids 790-end, expressed by baculovirus in Sf21 insect cells and purified using $Ni^{2+}$/NTA agarose. In a final reaction volume of 25 µL, KDR (h) (5-10 mU) is incubated with 8 mM MOPS pH 7.0, 0.2 mM EDTA, 250 µM KKKSPGEYVNIEFG, 10 mM MgAcetate and [γ-33P-ATP] (specific activity approx. 500 cpm/pmol, concentration as required). The reaction is initiated by the addition of the MgATP mix. After incubation for 40 minutes at room temperature, the reaction is stopped by the addition of 5 µL of a 3% phosphoric acid solution. 10 µL of the reaction is then spotted onto a P30 filtermat and washed three times for 5 minutes in 75 mM phosphoric acid and once in methanol prior to drying and scintillation counting. The compound is dissolved to 50× final assay concentration in 100% DMSO, and assayed using 0.5 µl of this compound solution in a final reaction volume of 25 ul as above. DMSO only (0.5 ul) is tested in parallel as a control.

Method C

Compounds were assayed as inhibitors of KDR in a manner substantially similar to the method described by Invitrogen. A kinase reaction buffer was prepared by dilution of the 5× Kinase Buffer stock solution (available from Invitrogen, item number PV3189) by adding 4 mL of 5× stock to 16 mL $H_2O$ to make 20 mL of 1× kinase reaction buffer.

Kinase reactions were performed in a 10 µL volume in low-volume 384-well plates. Typically, Corning model 3676 (black) or 3673 (white) plates are used. The concentration of substrate (Fluorescein-Poly GAT or Fluorescein-Poly GT, available from Invitrogen) in the assay was 200 nM, and the 1× kinase reaction buffer consists of 50 mM HEPES pH 7.5, 0.01% BRIJ-35, 10 mM $MgCl_2$, and 1 mM EGTA. The 2×KDR (VEGFR2)/Tyr 01 Peptide Mixture was prepared in 50 mM HEPES pH 7.5, 0.01% BRIJ-35, 10 mM $MgCl_2$, 1 mM EGTA. The final 10 µL Kinase Reaction consisted of 0.5-11.7 ng KDR (VEGFR2) and 2 µM Tyr 01 Peptide in 50 mM HEPES pH 7.5, 0.01% BRIJ-35, 10 mM $MgCl_2$, 1 mM EGTA. The kinase reaction was allowed to proceed for 1 hour at room temperature before a 5 µL of a 1:128 dilution of Development Reagent B was added.

Compound II-2 was tested as an inhibitor of KDR using the above assay protocol (Method C) resulting in 7% inhibition of the KDR enzyme at a concentration of 10 µM of test compound.

Method D

Briefly, 10× stocks of KDR from Invitrogen or BPS Bioscience (PV3660 or 40301), 1.13×ATP (AS001A) and Y9-Sox peptide substrate (KCZ1001) were prepared in 1× kinase reaction buffer consisting of 20 mM Tris, pH 7.5, 5 mM $MgCl_2$, 1 mM EGTA, 5 mM β-glycerophosphate, 5% glycerol (10× stock, KB002A) and 0.2 mM DTT (DS001A). 5 µL of enzyme were pre-incubated in a Corning (#3574) 384-well, white, non-binding surface microtiter plate (Corning, N.Y.) for 30 min at 27° C. with a 0.5 µL volume of 50% DMSO and serially diluted compounds prepared in 50% DMSO. Kinase reactions were started with the addition of 45 µL of the ATP/Y9 or Y12-Sox peptide substrate mix and monitored every 30-9 seconds for 60 minutes at $\lambda_{ex}360/\lambda_{em}485$ in a Synergy$^4$ plate reader from BioTek (Winooski, Vt.). At the conclusion of each assay, progress curves from each well were examined for linear reaction kinetics and fit statistics ($R^2$, 95% confidence interval, absolute sum of squares). Initial velocity (0 minutes to 20+ minutes) from each reaction was determined from the slope of a plot of relative fluorescence units vs time (minutes) and then plotted against inhibitor concentration to estimate $IC_{50}$ from log [Inhibitor] vs Response, Variable Slope model in GraphPad Prism from GraphPad Software (San Diego, Calif.).

[KDR]=2.5 nM, [ATP]=75 µM and [Y12-Sox peptide]=5 µM (ATP $K_{Mapp}$=75 µM)

KDR inhibition data, obtained using above assay protocol Method D, for exemplary compounds are summarized in Table 9, below.

TABLE 9

KDR Inhibition Data

| Compound # | $IC_{50}$ (µM) |
|---|---|
| II-2 | 3.0 |
| II-6 | 10.0 |
| II-23 | 2.2 |
| II-45 | 10.0 |
| II-52 | 3.0 |
| II-55 | 4.5 |
| III-6 | 8.1 |
| III-14 | 2.1 |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A method for treating a PDGFR-, c-KIT-, KDR, or cFMS-mediated disorder in a patient in need thereof, comprising the step of administering to said patient compound of formula I:

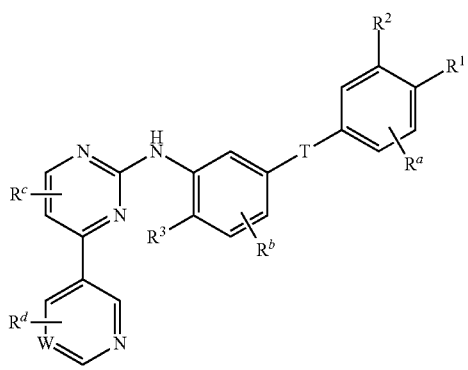

I or a pharmaceutically acceptable salt thereof, wherein:

T is —NHC(O)— or —C(O)NH—;

W is CH or N;

each of $R^a$, $R^b$, $R^c$, and $R^d$ is independently selected from R, OR, or halogen;

each R is independently hydrogen, lower alkyl, or lower haloalkyl;

$R^1$ is -L-Y, wherein:

L is a bivalent $C_{2-8}$ straight or branched, hydrocarbon chain wherein L has at least one double bond and at least one methylene unit of L is replaced by cyclopropylene, —NRC(O)—, —C(O)NR—, —S—, —S(O)—, —SO$_2$—, —C(=S)—, —C(=NR)—, —N=N—, or —C(=N$_2$)—; and one or two additional methylene units of L are optionally and independently replaced by —O—, —N(R)—, or —C(O)—; or L is a bivalent $C_{2-8}$ straight or branched, hydrocarbon chain wherein L has at least one triple bond and one or two additional methylene units of L are optionally and independently replaced by —NRC(O)—, —C(O)NR—, —S—, —S(O)—, —SO$_2$—, —C(=S)—, —C(=NR)—, —O—, —N(R)—, or —C(O)—; or L is a bivalent $C_{2-8}$ straight or branched, hydrocarbon chain wherein one methylene unit of L is replaced by cyclopropylene and one or two additional methylene units of L are independently replaced by —C(O)—, —NRC(O)—, —C(O)NR—, —N(R)SO$_2$—, or —SO$_2$N(R)—; or L is a bivalent $C_{1-8}$, straight or branched, alkylene chain, wherein at least one methylene unit of L is replaced by —C(=N$_2$)—, and one or two additional methylene units of L are optionally and independently replaced by —NRC(O)—, —C(O)NR—, —S—, —S(O)—, —SO$_2$—, —C(=S)—, —C(=NR)—, —O—, —N(R)—, or —C(O)—; and Y is hydrogen, $C_{1-6}$ aliphatic optionally substituted with oxo, halogen, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 groups independently selected from -Q-Z, oxo, halogen, CN, or $C_{1-6}$ aliphatic, wherein:

Q is a covalent bond or a bivalent $C_{1-6}$ saturated or unsaturated, straight or branched, hydrocarbon chain, wherein one or two methylene units of Q are optionally and independently replaced by —NR—, —NRC(O)—, —C(O)NR—, —S—, —O—, —C(O)—, —SO—, or —SO$_2$—; and Z is hydrogen or $C_{1-6}$ aliphatic optionally substituted with oxo, halogen, or CN; or L is a covalent bond or a bivalent $C_{1-8}$ saturated or unsaturated, straight or branched, hydrocarbon chain, wherein one, two, or three methylene units of L are optionally and independently replaced by —NR—, —N(R)C(O)—, —C(O)N(R)—, —O—, —C(O)—, —OC(O)—, —C(O)O—, —S—, —SO—, —SO$_2$—, or —C(=S)—; and Y is selected from:

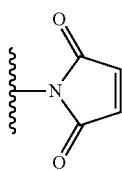

i

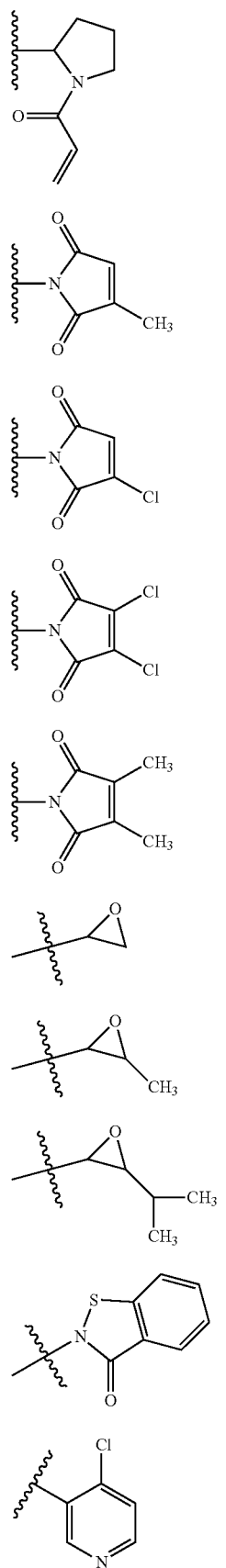
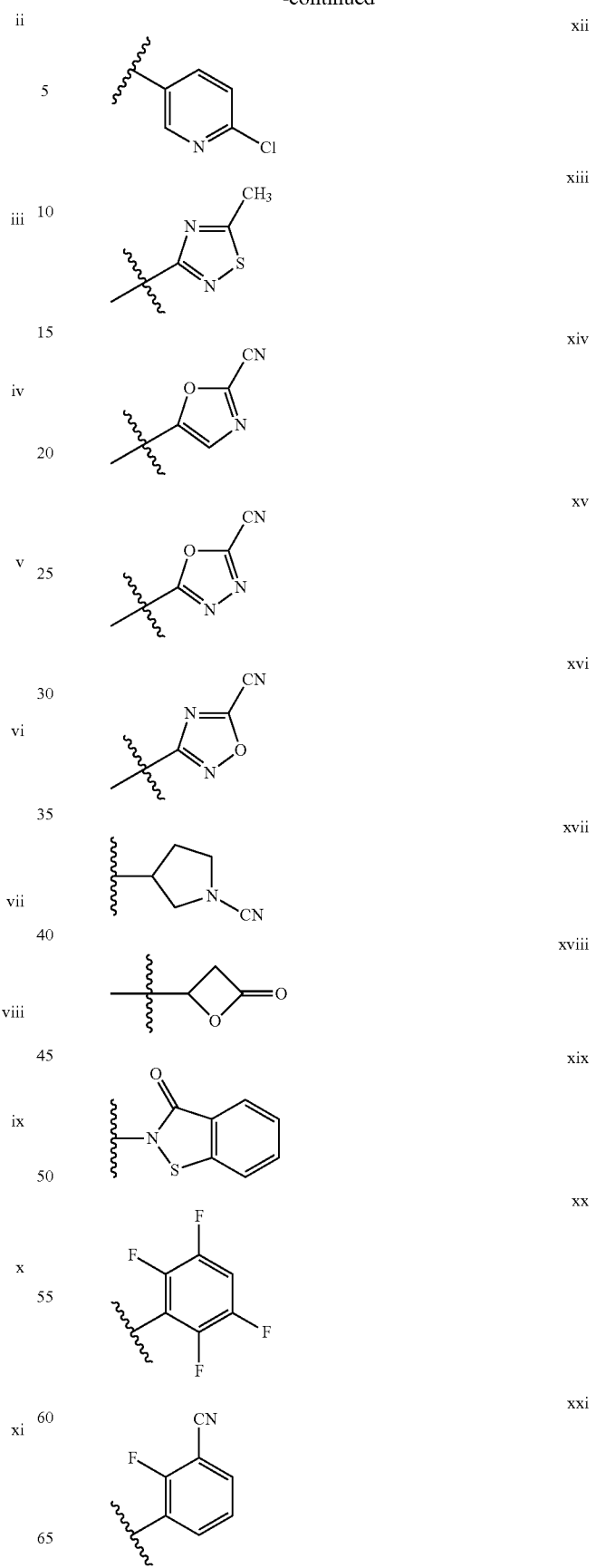

129
-continued
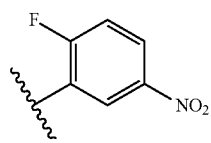
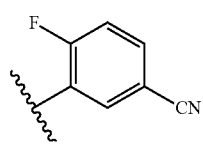
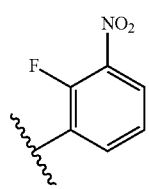
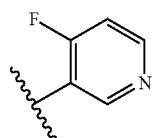
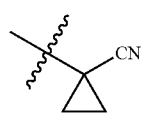
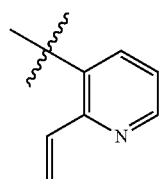
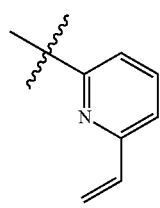
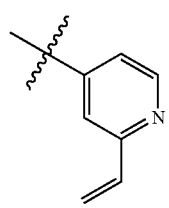
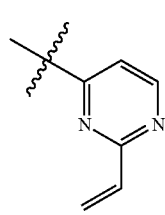
130
-continued
xxii
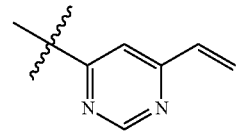
xxiii
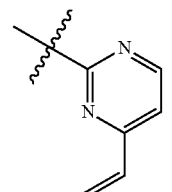
xxiv
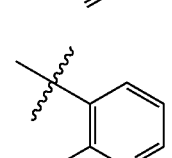
xxv
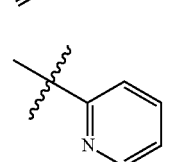
xxvi
xxvii
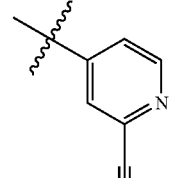
xxviii
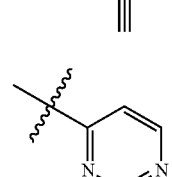
xxix
xxx
xxxi
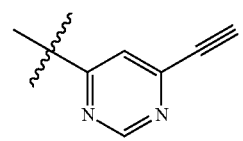
xxxii
xxxiii
xxxiv
xxxv
xxxvi
xxxvii
xxxviii
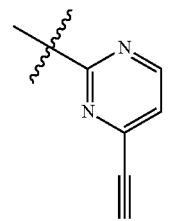

-continued
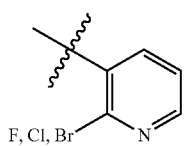
xxxix
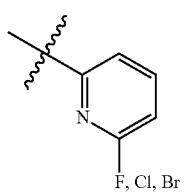
xl
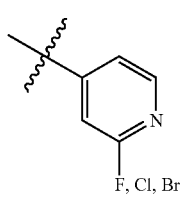
xli
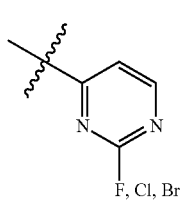
xlii
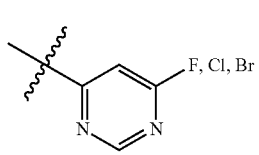
xliii
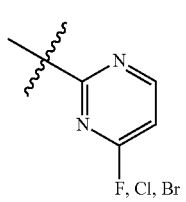
xliv
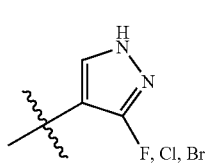
xlv
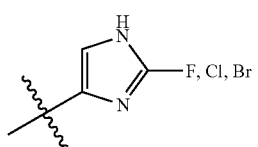
xlvi
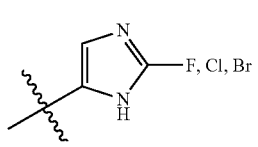
xlvii
-continued
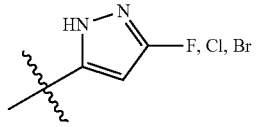
xlviii
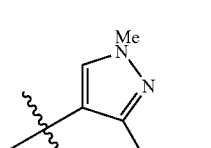
xlix
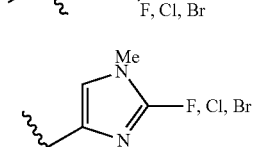
l
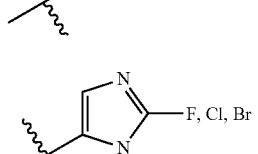
li
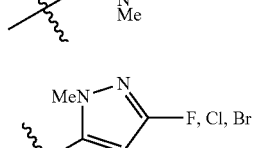
lii
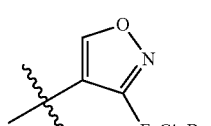
liii
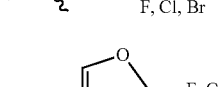
liv
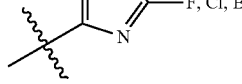
lv
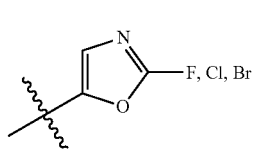
lvi
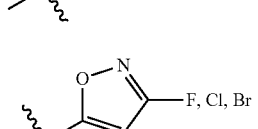
lvii
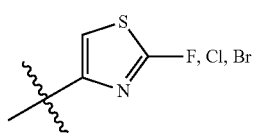
lviii

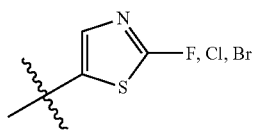 lix
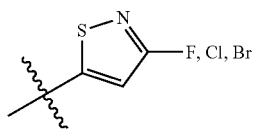 lx
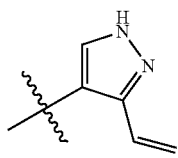 lxi
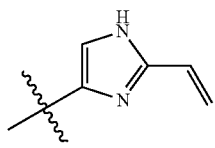 lxii
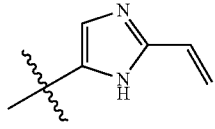 lxiii
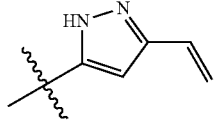 lxiv
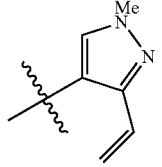 lxv
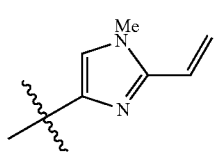 lxvi
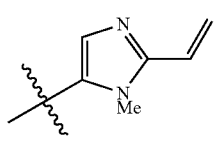 lxvii
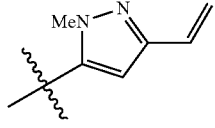 lxviii
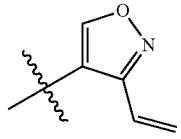 lxix
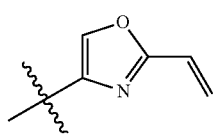 lxx
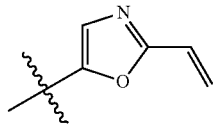 lxxi
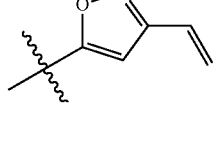 lxxii
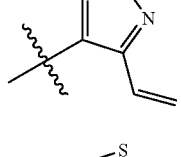 lxxiii
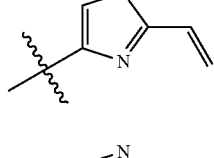 lxxiv
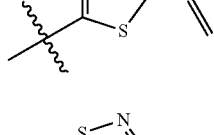 lxxv
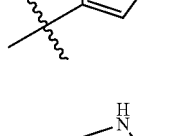 lxxvi
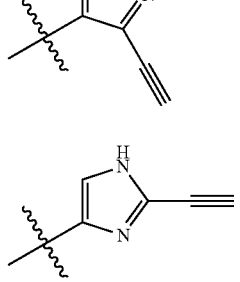 lxxvii
lxxviii

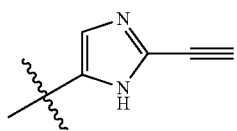 lxxix
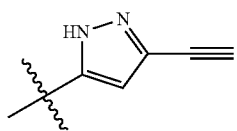 lxxx
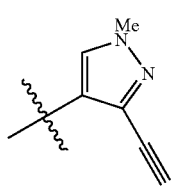 lxxxi
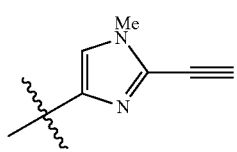 lxxxii
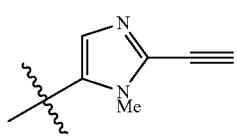 lxxxiii
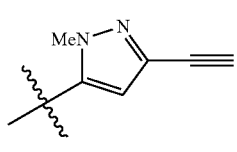 lxxxiv
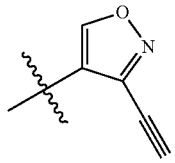 lxxxv
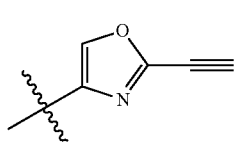 lxxxvi
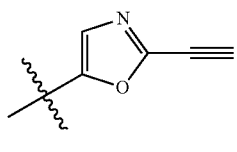 lxxxvii
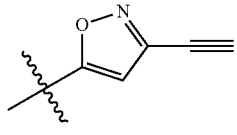 lxxxviii
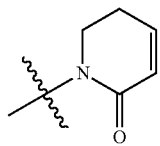 lxxxix
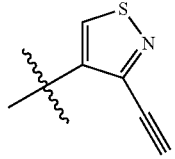 xc
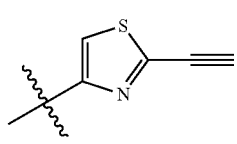 xci
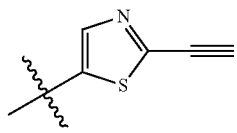 xcii
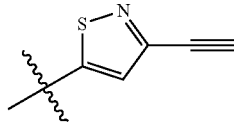 xciii
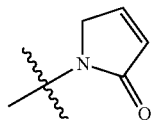 xciv
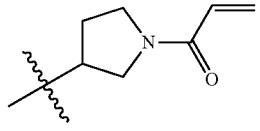 xcv
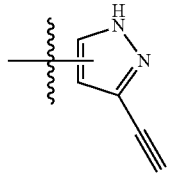 xcvi
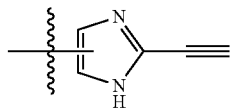 xcvii
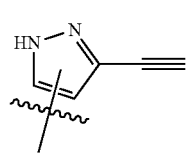 xcviii

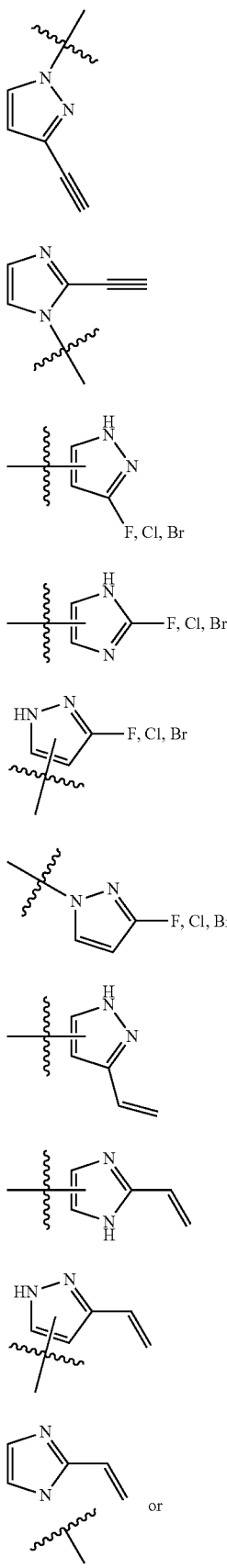

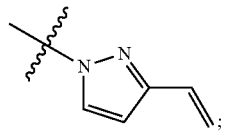

R² is selected from R, halogen, —N(R)C(O)OR, or 1-imidazoyl substituted with R, or:

R¹ and R² are taken together with their intervening atoms to form a 5-7 membered saturated, partially unsaturated, or aryl ring having 0-3 heteroatoms independently selected from nitrogen, oxygen, or sulfur, wherein said ring is substituted with -L-Y and 0-3 groups independently selected from oxo, halogen, CN, or $C_{1-6}$ aliphatic; and R³ is selected from hydrogen, lower alkyl, or halogen, or a composition thereof, wherein the PDGFR-, c-KIT-, KDR, or cFMS-mediated disorder is selected from breast cancer and rheumatoid arthritis.

2. The method according to claim 1, wherein the compound of formula I irreversibly inhibits PDGFR, c-KIT, KDR, or cFMS, by covalently modifying Cys814 of PDGFR-α, Cys822 of PDGFR-β, Cys1024 of KDR, Cys788 of c-KIT, or Cys774 of cFMS.

3. The method according to claim 1, wherein the disorder is breast cancer.

4. The method according to claim 1, wherein the disorder is rheumatoid arthritis.

5. The method according to claim 1, wherein said compound is of formula II-a or III-a:

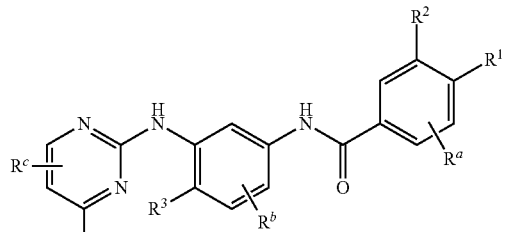

II-a

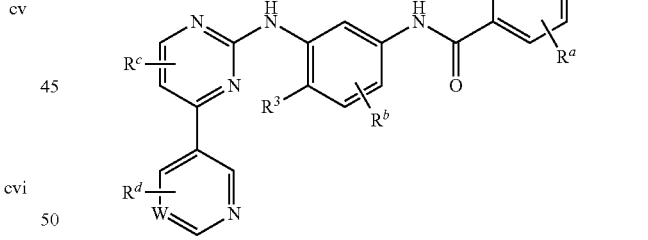

III-a

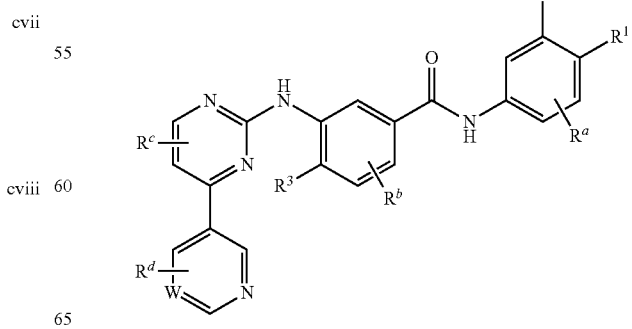

or a pharmaceutically acceptable salt thereof, wherein:

L is a bivalent $C_{2-8}$ straight or branched, hydrocarbon chain wherein L has at least one double bond and at least one methylene unit of L is replaced by cyclopropylene, —NRC(O)—, —C(O)NR—, —S—, —S(O)—, —SO$_2$—, —C(=S)—, —C(=NR)—, —N=N—, or —C(=N$_2$)—, and one or two additional methylene units of L are optionally and independently replaced by —O—, —N(R)—, or —C(O)—; and $R^2$ is selected from R, halogen, —N(R)C(O)OR, or 1-imidazoyl substituted with R.

6. The method according to claim 5, wherein:

Y is hydrogen or $C_{1-6}$ aliphatic optionally substituted with oxo, halogen, or CN; and $R^3$ is lower alkyl.

7. The method according to claim 6, wherein L is —NHC(O)CH=CH—, —NHC(O)CH=CHCH$_2$N(CH$_3$)—, —NHC(O)CH=CHCH$_2$O—, —CH$_2$NHC(O)CH=CH—, —NHSO$_2$CH=CH—, —NHSO$_2$CH=CHCH$_2$—, —NHC(O)(C=N$_2$)—, —NHC(O)(C=N$_2$)C(O)—, or —NHC(O)C(=CH$_2$)CH$_2$—.

8. The method according to claim 1, wherein:

L is a bivalent $C_{2-8}$ straight or branched, hydrocarbon chain wherein L has at least one triple bond and one or two additional methylene units of L are optionally and independently replaced by —NRC(O)—, —C(O)NR—, —S—, —S(O)—, —SO$_2$—, —C(=S)—, —C(=NR)—, —O—, —N(R)—, or —C(O)—; and Y is hydrogen, $C_{1-6}$ aliphatic optionally substituted with oxo, halogen, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with at 1-4 groups independently selected from -Q-Z, oxo, halogen, CN, or $C_{1-6}$ aliphatic.

9. The method according to claim 8, wherein:

L is —C≡C—, —C≡CCH$_2$N(isopropyl)-, —NHC(O)C≡CCH$_2$CH$_2$—, —CH$_2$—C≡C—CH$_2$—, or —C≡CCH$_2$O—; and Y is hydrogen, $C_{1-6}$ aliphatic optionally substituted with oxo, halogen, or CN, phenyl, pyridyl, or an optionally substituted saturated 3-6 membered monocyclic ring having 1-3 heteroatoms independently selected from nitrogen, oxygen, or sulfur, and wherein said ring is substituted with at 1-4 groups independently selected from -Q-Z, oxo, halogen, CN, or $C_{1-6}$ aliphatic.

10. The method according to claim 1, wherein: L is a covalent bond, —CH$_2$—, —NH—, —CH$_2$NH—, —NHCH$_2$—, —NHC(O)—, —NHC(O)CH$_2$OC(O)—, —CH$_2$NHC(O)—, —NHSO$_2$—, —NHSO$_2$CH$_2$—, —NHC(O)CH$_2$OC(O)—, or —SO$_2$NH— and Y is selected from:

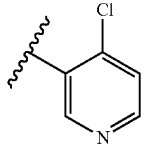

i

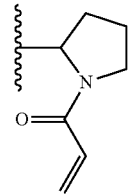

ii

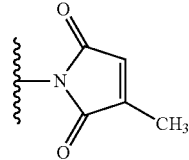

iii

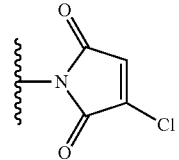

iv

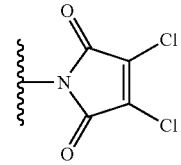

v

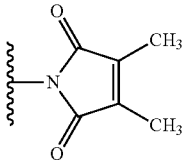

vi

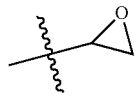

vii

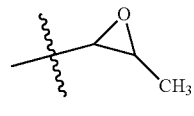

viii

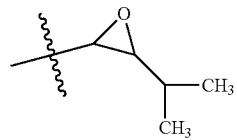

ix

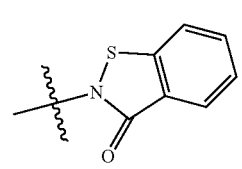

x

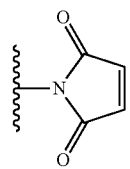

xi

-continued
xii
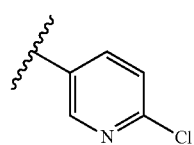
xiii
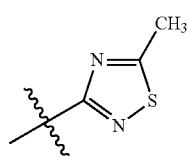
xiv
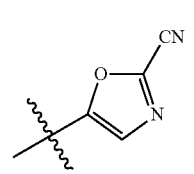
xv
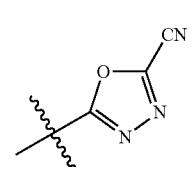
xvi
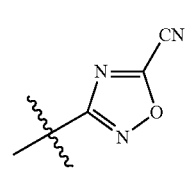
xvii
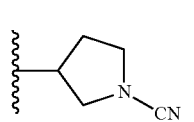
xviii
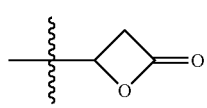
xix
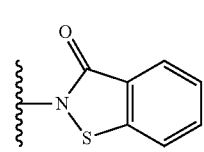
xx
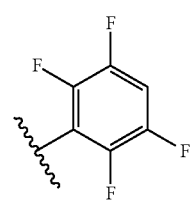
xxi
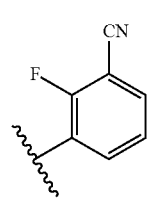
-continued
xxii
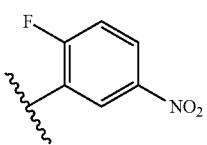
xxiii
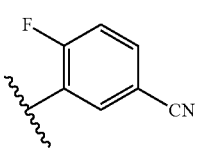
xxiv
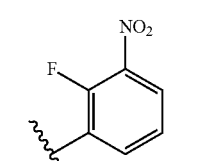
xxv
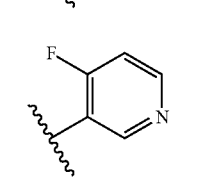
xxvi
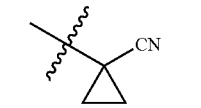
xxvii
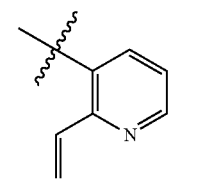
xxviii
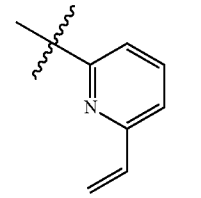
xxix
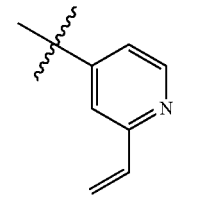
xxx
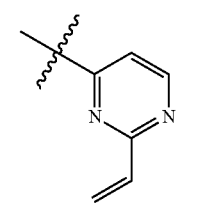

-continued
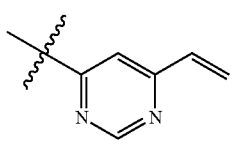
xxxi
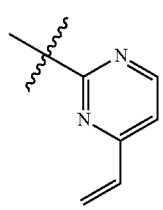
xxxii
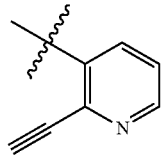
xxxiii
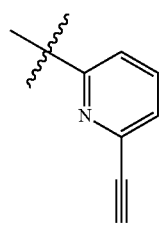
xxxiv
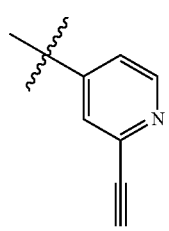
xxxv
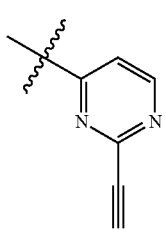
xxxvi
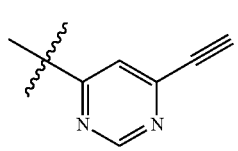
xxxvii
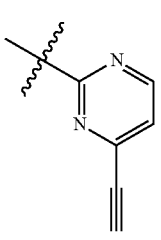
xxxviii
-continued
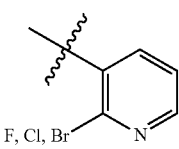
xxxix
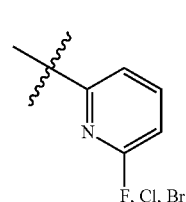
xl
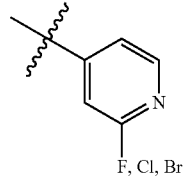
xli
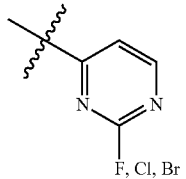
xlii
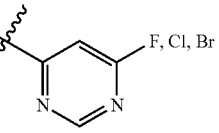
xliii
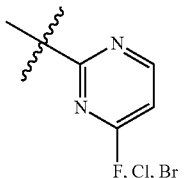
xliv
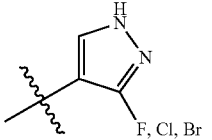
xlv
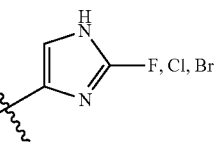
xlvi
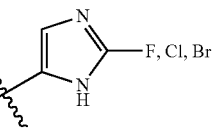
xlvii

| | | |
|---|---|---|
| 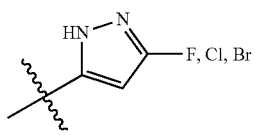 | xlviii | 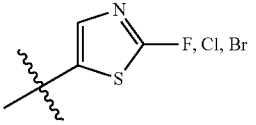 lix |
| 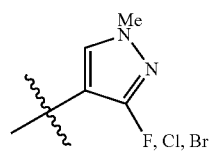 | xlix | 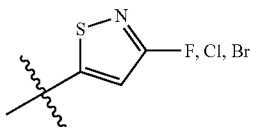 lx |
| 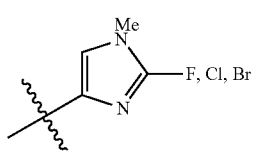 | l | 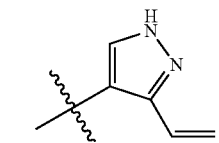 lxi |
| 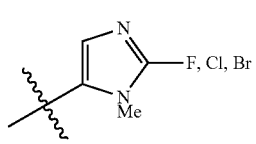 | li | 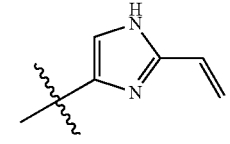 lxii |
| 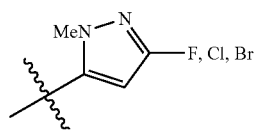 | lii | 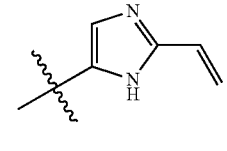 lxiii |
| 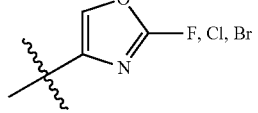 | liii | 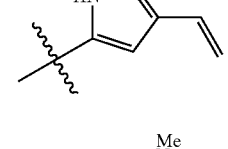 lxiv |
| 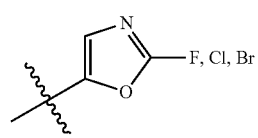 | liv | 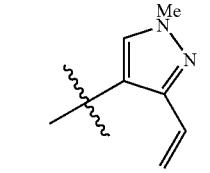 lxv |
| 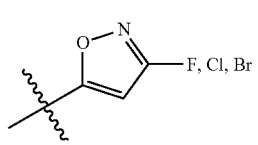 | lv | 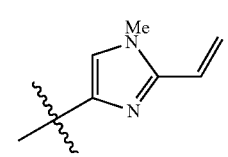 lxvi |
| 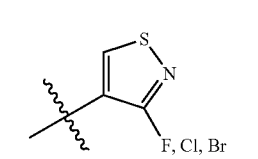 | lvi | 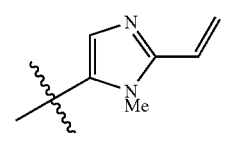 lxvii |
| 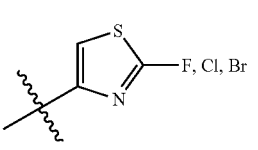 | lvii | 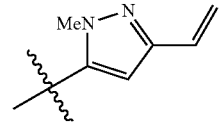 lxviii |
| | lviii | |

| | |
|---|---|
| 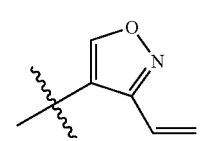 lxix | 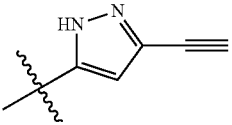 lxxx |
| 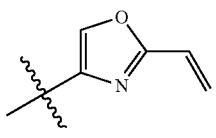 lxx | 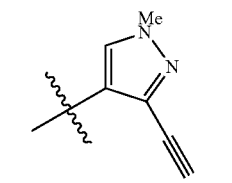 lxxxi |
| 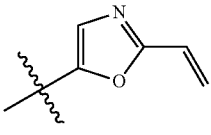 lxxi | 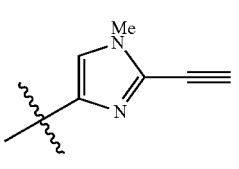 lxxxii |
| 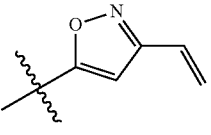 lxxii | 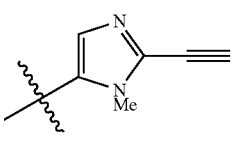 lxxxiii |
| 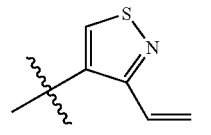 lxxiii | 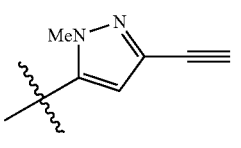 lxxxiv |
| 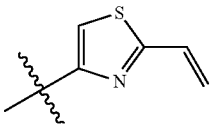 lxxiv | 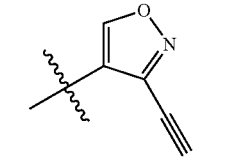 lxxxv |
| 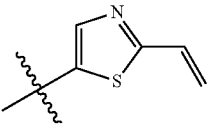 lxxv | 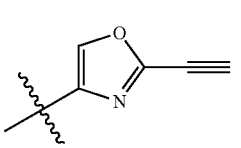 lxxxvi |
| 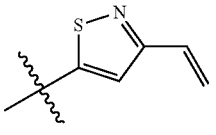 lxxvi | 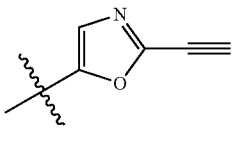 lxxxvii |
| 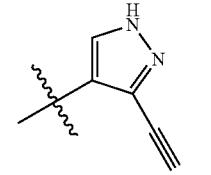 lxxvii | 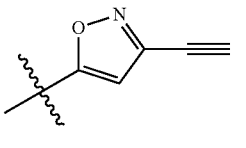 lxxxviii |
| 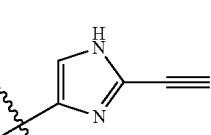 lxxviii | 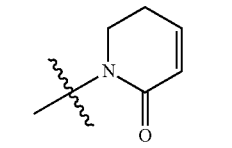 lxxxix |
| 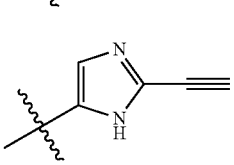 lxxix | |

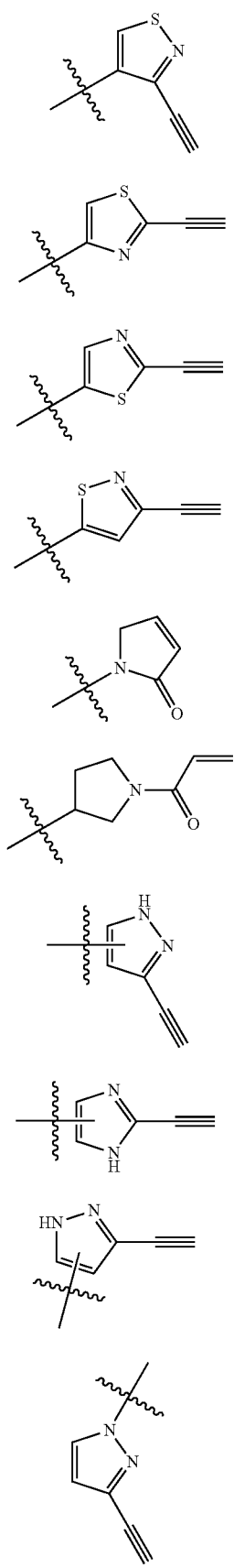
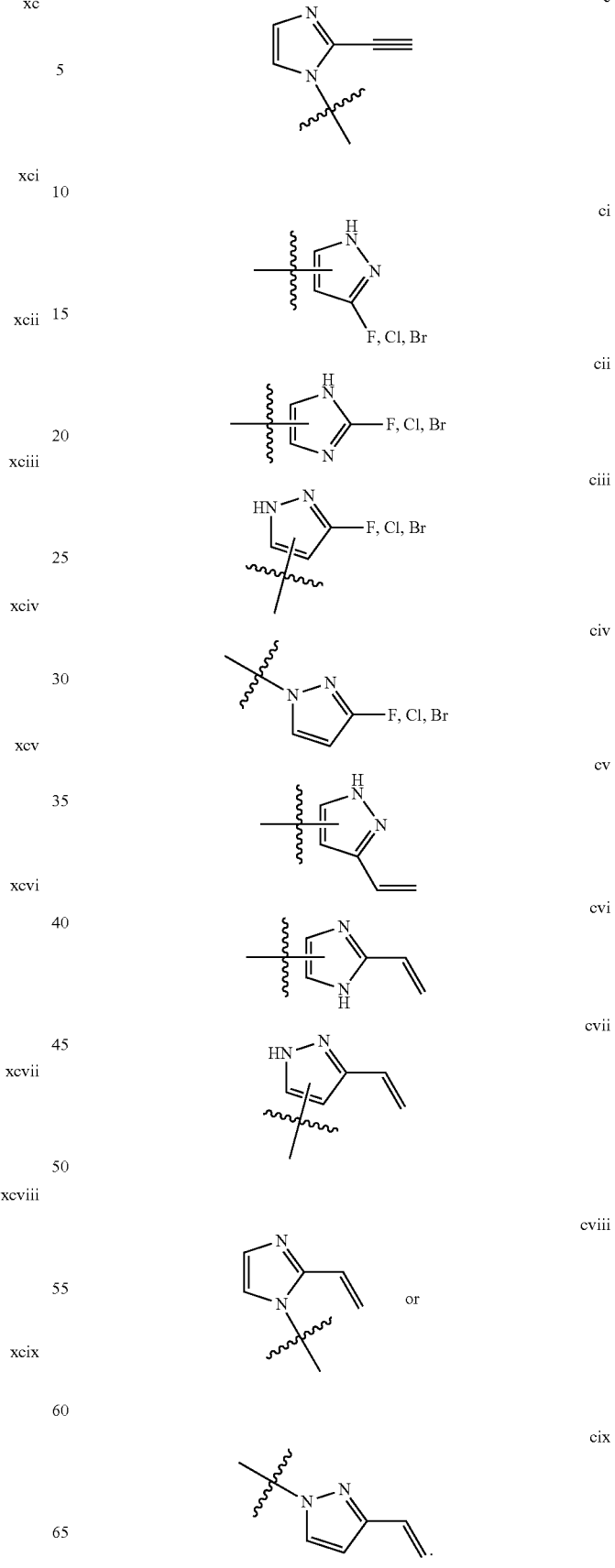

11. The method according to claim 1, wherein said compound is selected from the group consisting of:
II-1
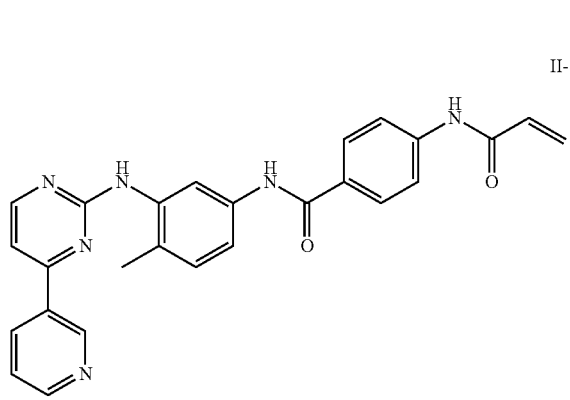
II-2
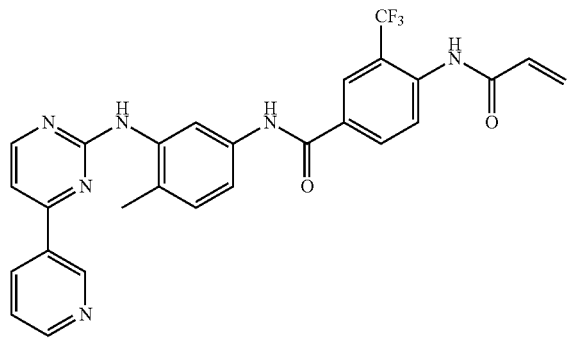
II-3
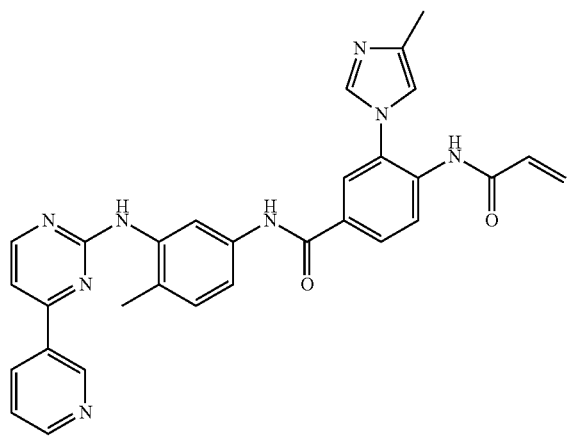
II-4
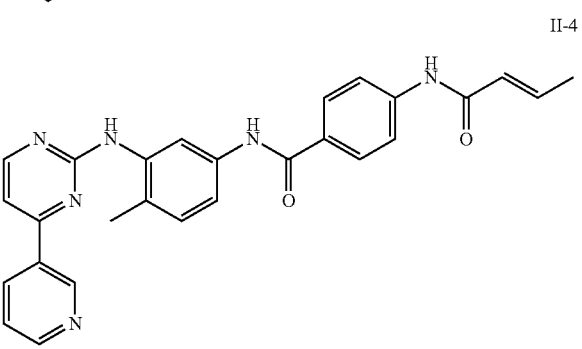
-continued
II-5
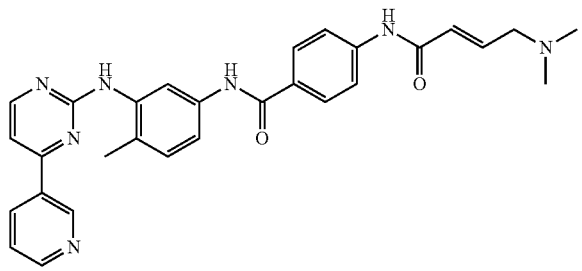
II-6
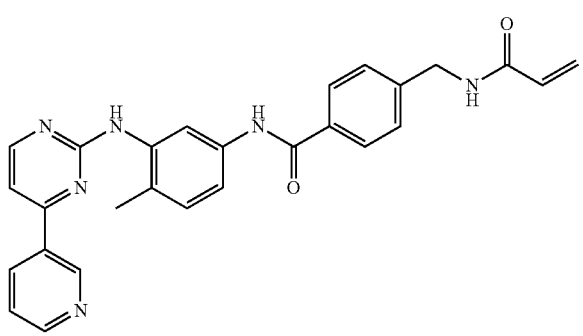
II-7
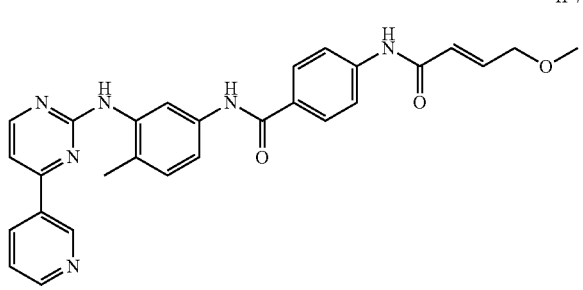
II-8
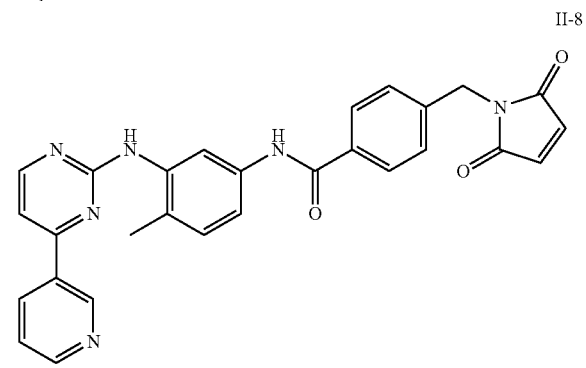
II-9
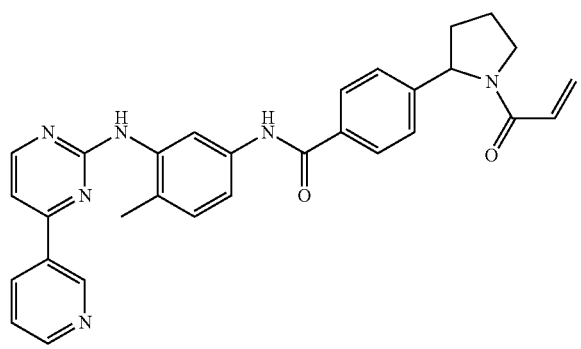

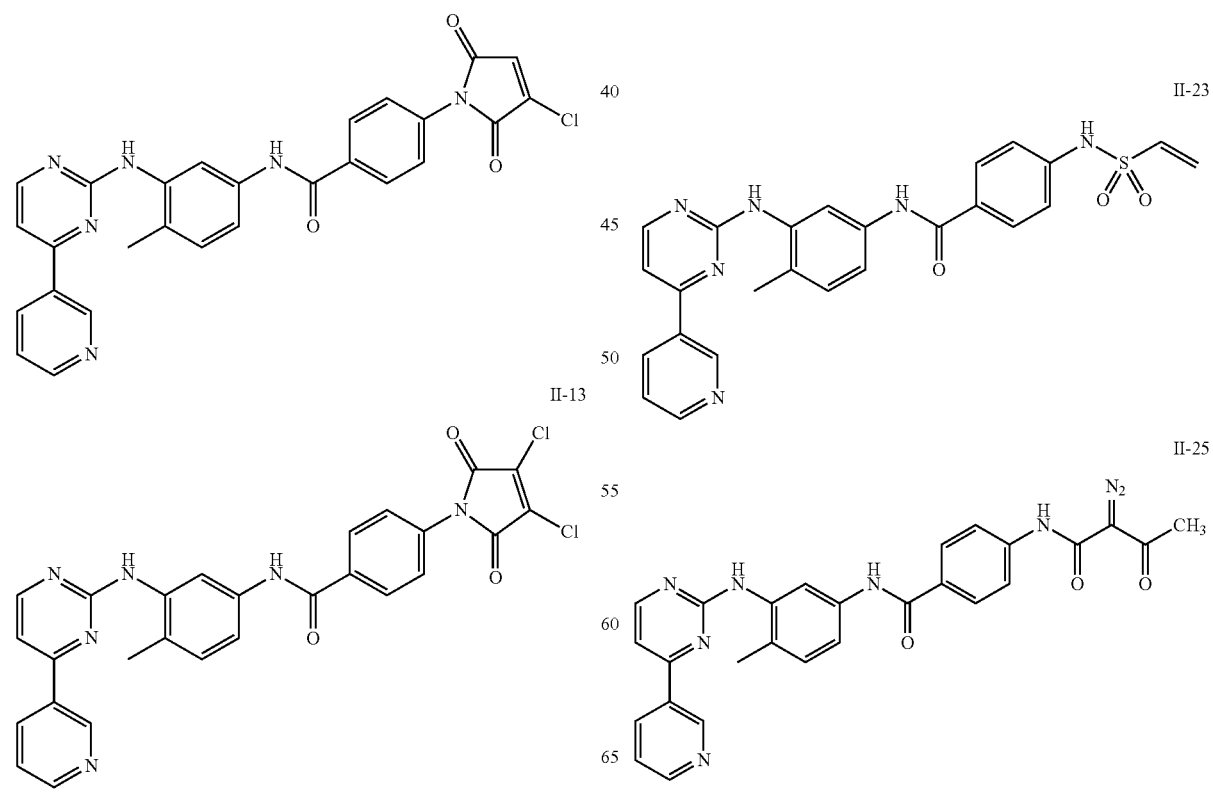

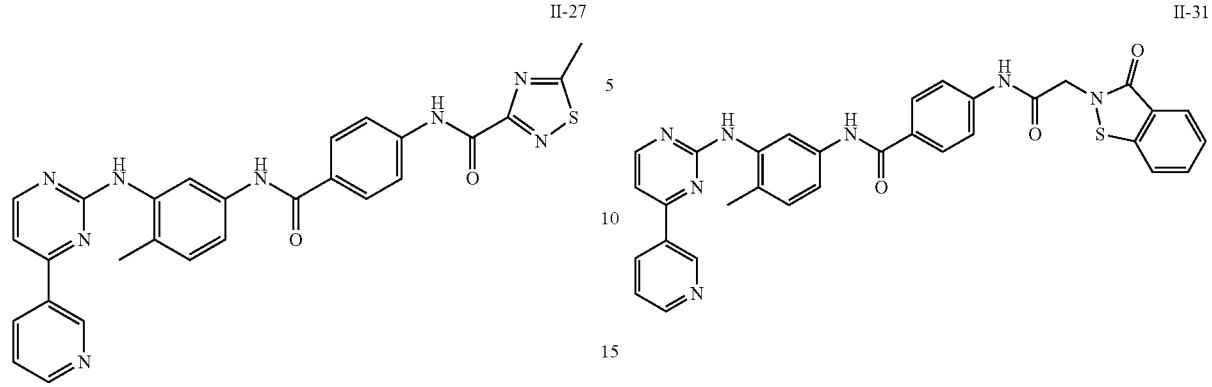
II-27
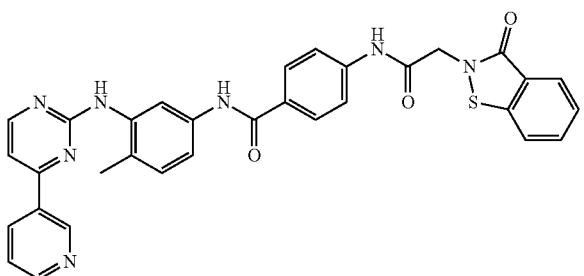
II-31
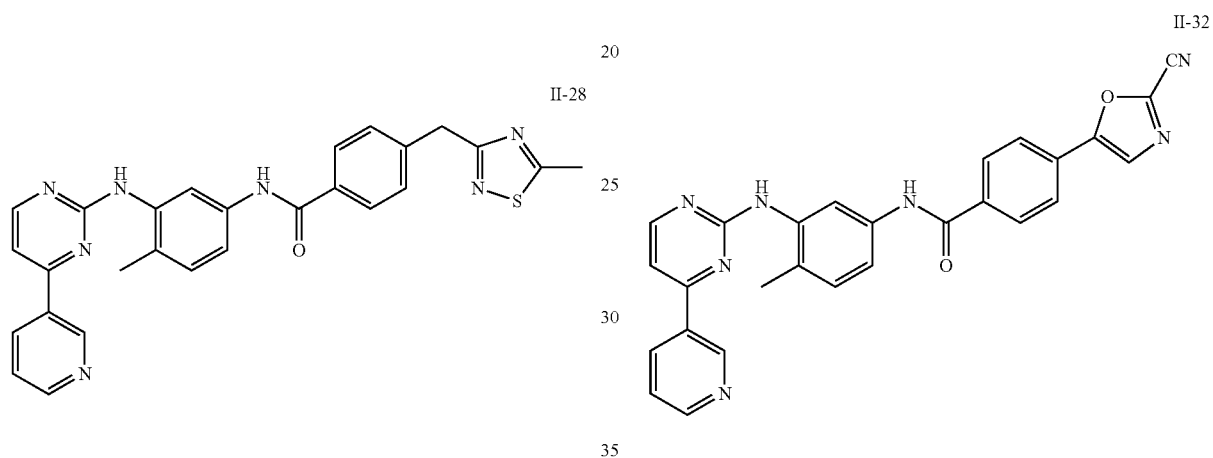
II-28
II-32
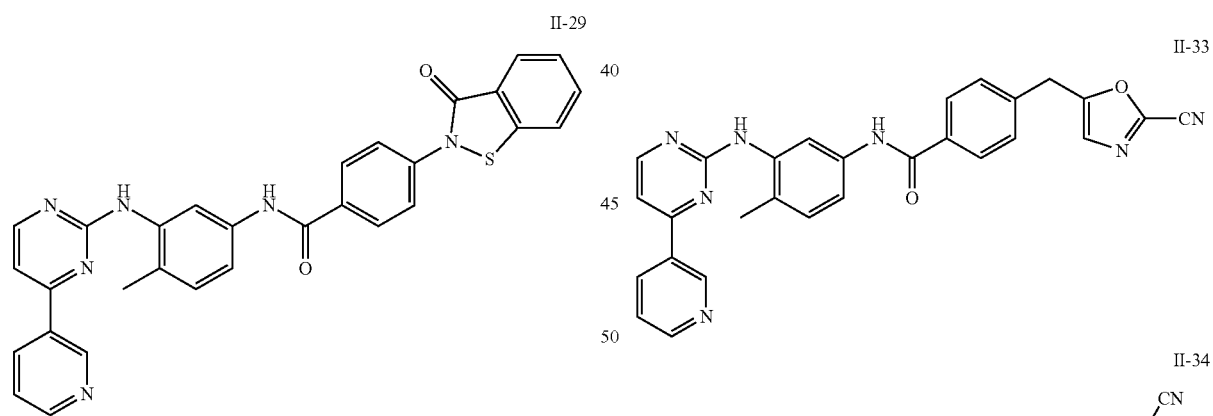
II-29
II-33
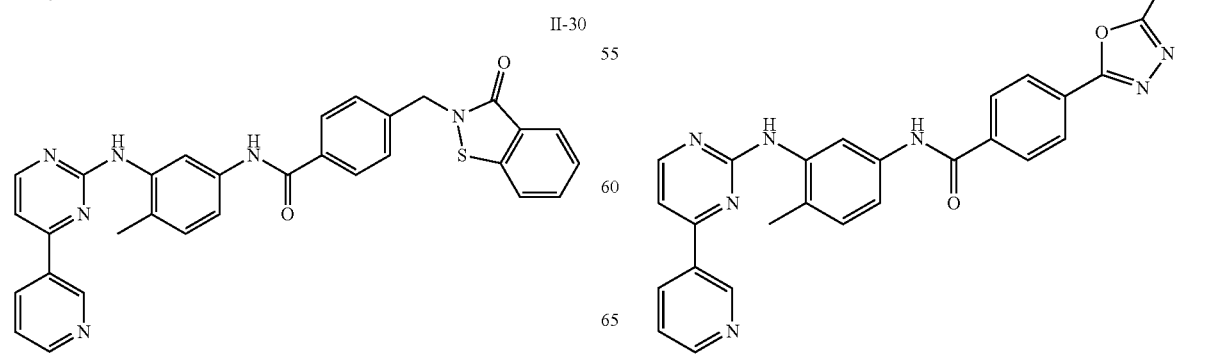
II-30
II-34

II-35
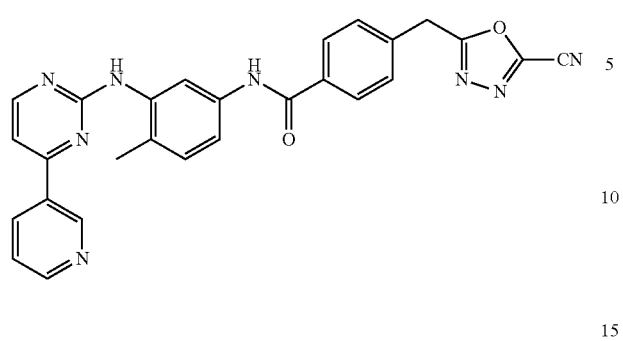
II-36
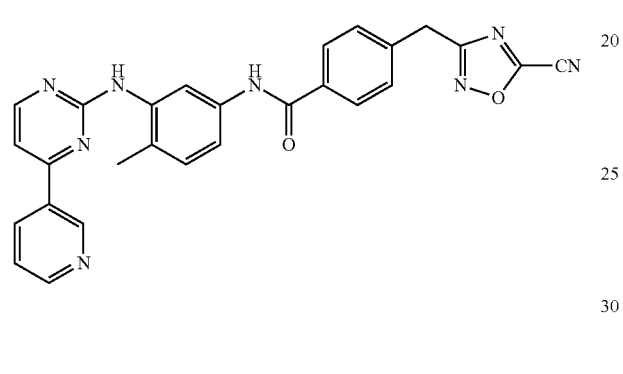
II-37
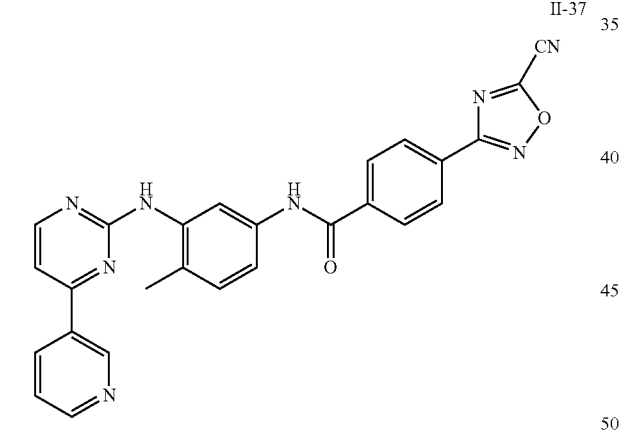
II-38
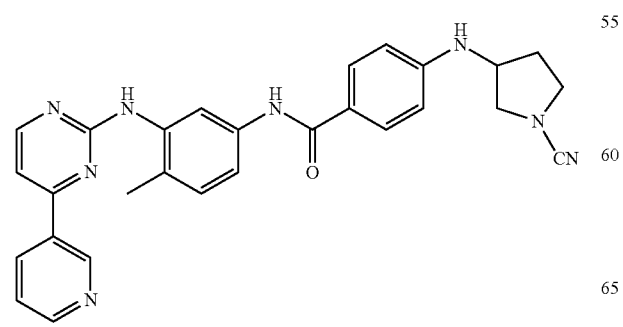
II-39
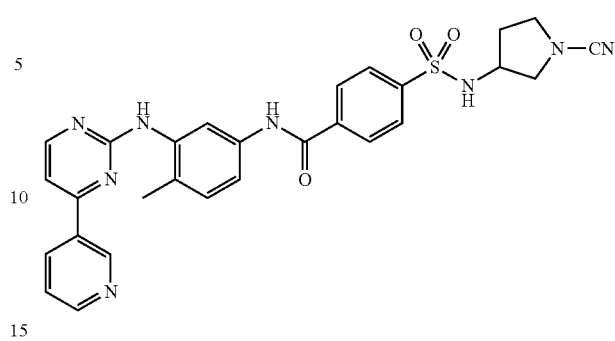
II-40
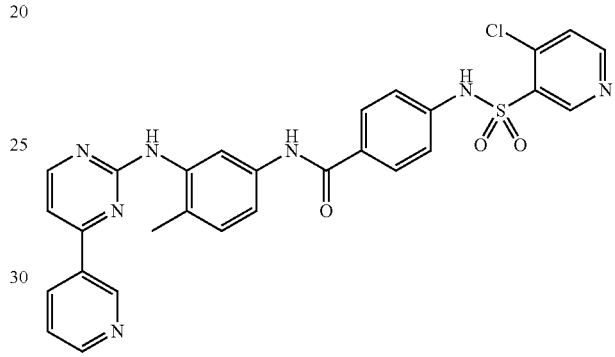
II-41
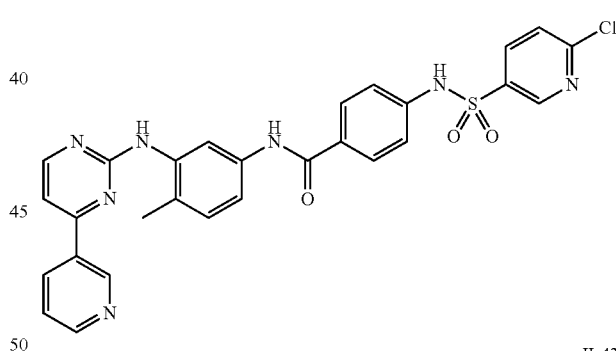
II-43
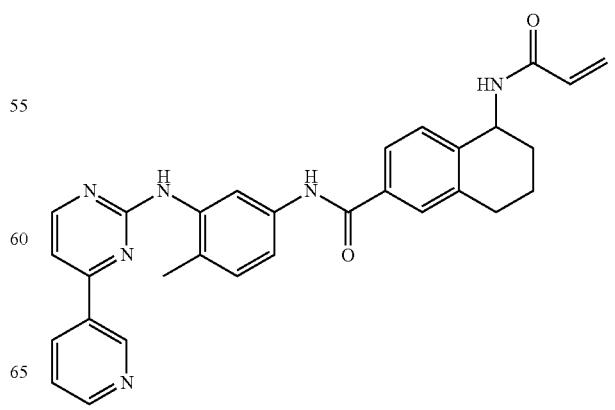

-continued
II-44
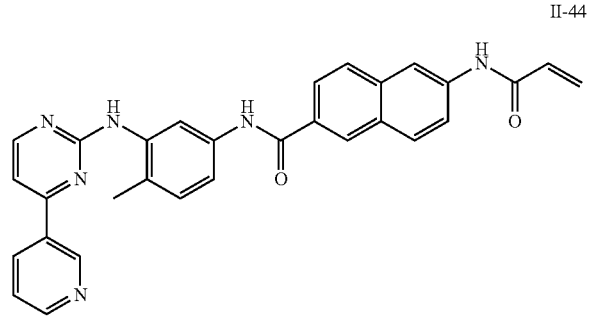
II-45
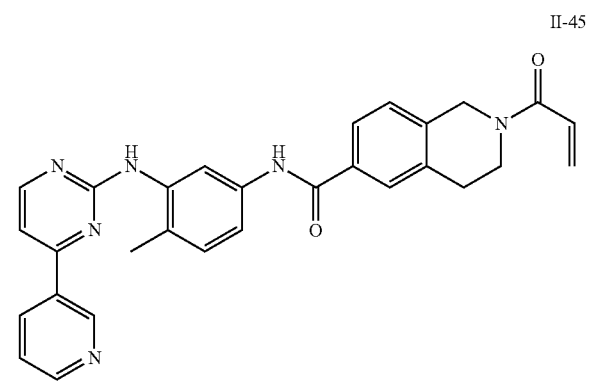
II-46
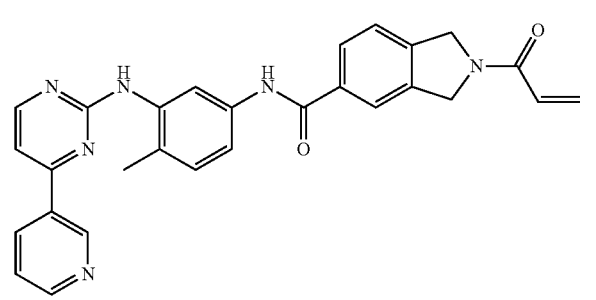
II-47
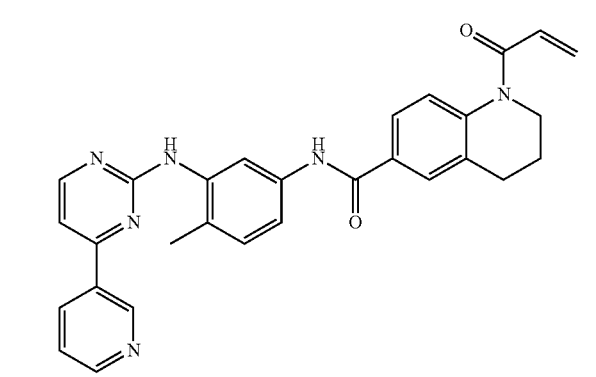
-continued
II-48
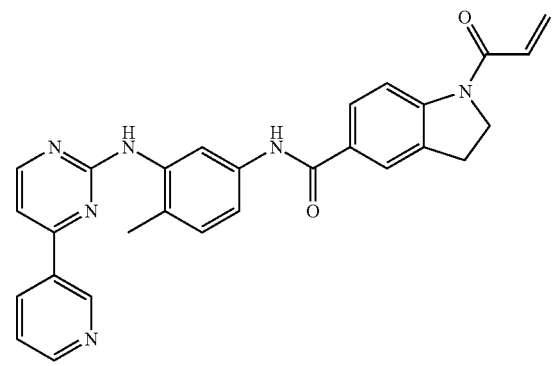
II-50
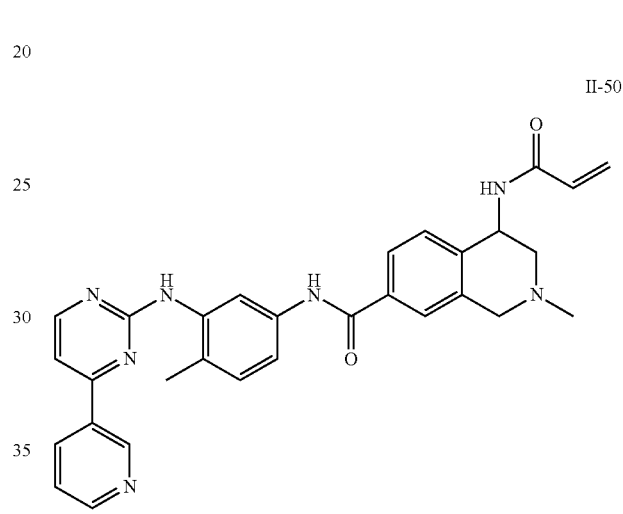
II-51
II-52
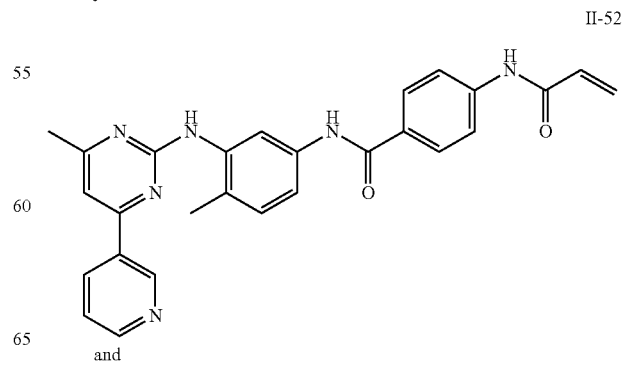
and

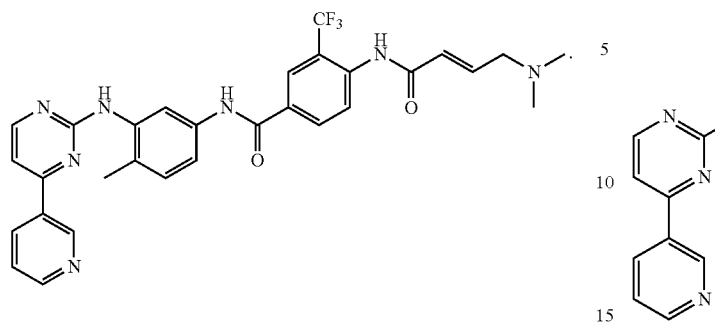
12. The method according to claim 1 wherein said compound is selected from the group consisting of:
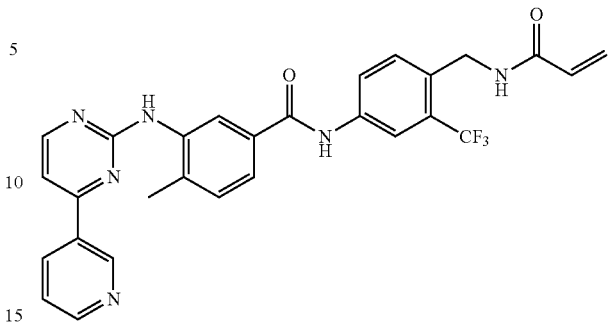
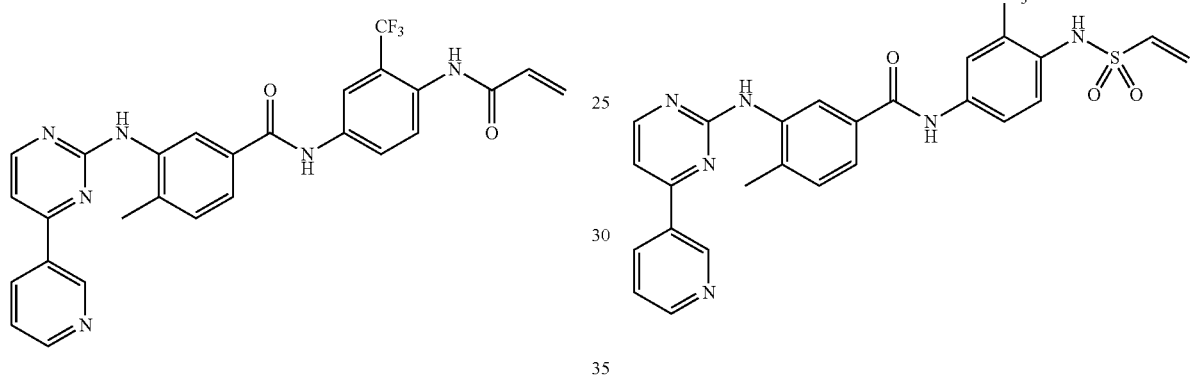
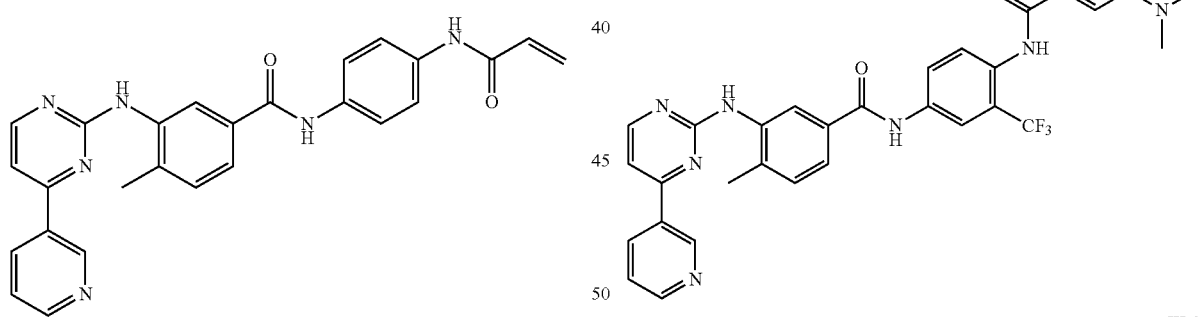
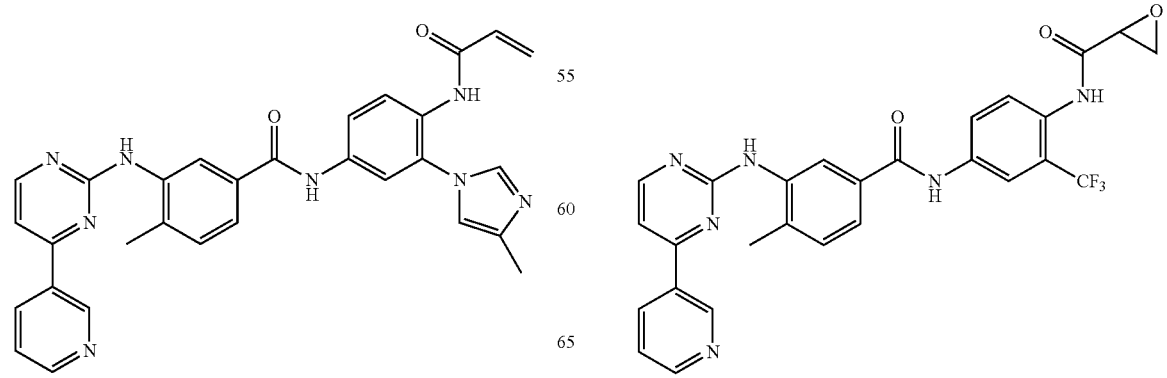

-continued
III-9
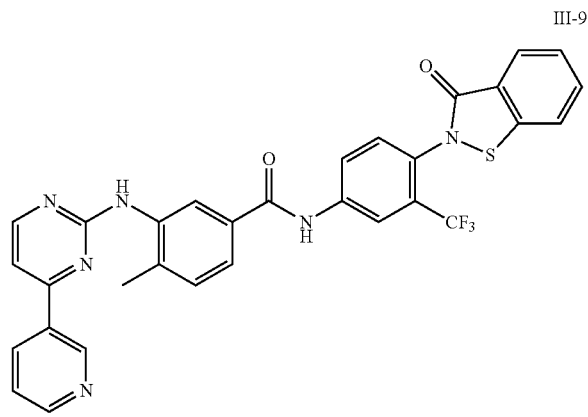
III-10
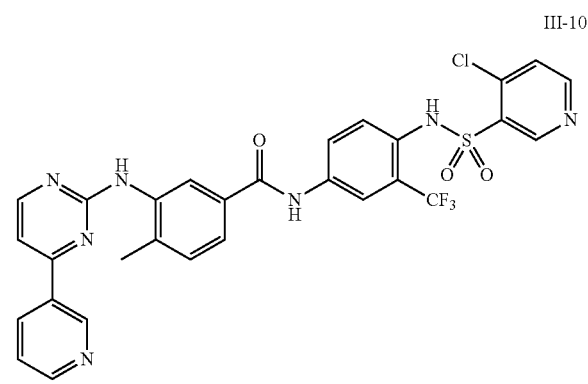 [SMILES: Cc1ccc(NC(=O)c2ccc(NS(=O)(=O)c3cnccc3Cl)cc2)cc1Nc1nccc(-c2cccnc2)n1]
III-11
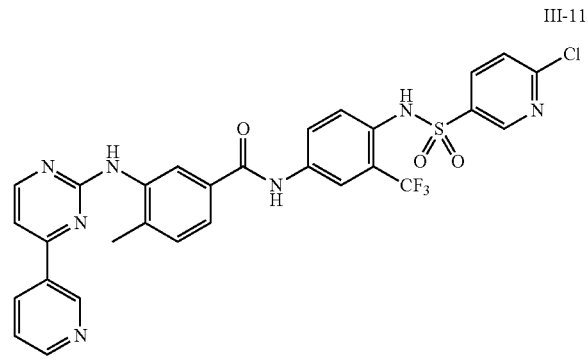 [SMILES: Cc1ccc(NC(=O)c2ccc(NS(=O)(=O)c3ccc(Cl)nc3)cc2)cc1Nc1nccc(-c2cccnc2)n1]
-continued
III-12
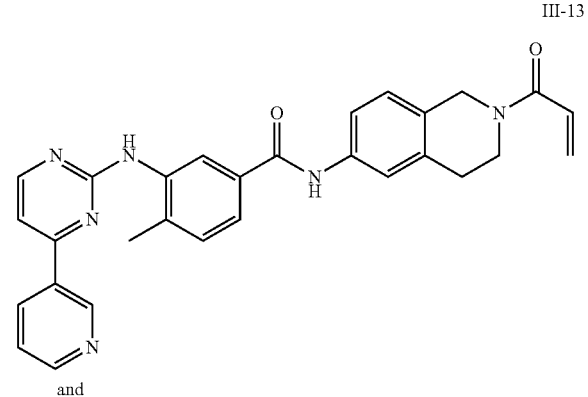
III-13
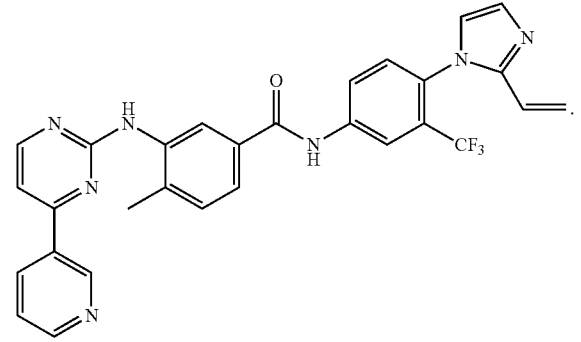
and
III-19
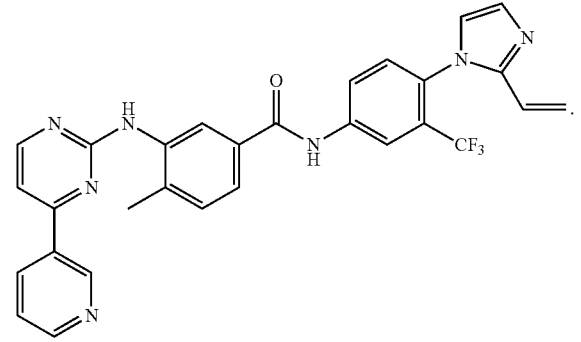
* * * * *